US010820728B1

(12) United States Patent
Rao

(10) Patent No.: US 10,820,728 B1
(45) Date of Patent: Nov. 3, 2020

(54) ELECTRONICALLY CONTROLLABLE PILLOW

(71) Applicant: Raj Rao, Newport Coast, CA (US)

(72) Inventor: Raj Rao, Newport Coast, CA (US)

(*) Notice: Subject to any disclaimer, the term of this patent is extended or adjusted under 35 U.S.C. 154(b) by 0 days.

(21) Appl. No.: 16/364,842

(22) Filed: Mar. 26, 2019

Related U.S. Application Data

(63) Continuation of application No. 14/846,765, filed on Sep. 5, 2015, now Pat. No. 10,238,222.
(Continued)

(51) Int. Cl.
*A47C 27/10* (2006.01)
*A47G 9/10* (2006.01)
(Continued)

(52) U.S. Cl.
CPC ............ *A47G 9/1036* (2013.01); *A47G 9/10* (2013.01); *A47G 9/1027* (2013.01); *A61B 5/01* (2013.01); *A61B 5/4815* (2013.01); *A61B 5/6814* (2013.01); *A61B 5/6892* (2013.01); *A61F 7/0085* (2013.01); *A61F 7/02* (2013.01); *A61M 21/02* (2013.01); *A61B 5/1036* (2013.01); *A61B 2562/0219* (2013.01); *A61B 2562/0247* (2013.01); *A61B 2562/0257* (2013.01); *A61F 2007/0002* (2013.01); *A61F 2007/006* (2013.01); *A61F 2007/0055* (2013.01); *A61F 2007/0057* (2013.01); *A61F 2007/0059* (2013.01); *A61F 2007/0064* (2013.01); *A61F 2007/0093* (2013.01); *A61F 2007/0094* (2013.01); *A61F 2007/0095* (2013.01); *A61F 2007/0246* (2013.01); *A61F 2007/0258* (2013.01); *A61M 2021/0027* (2013.01); *A61M 2021/0066* (2013.01);
(Continued)

(58) Field of Classification Search
CPC .................. A47C 27/10; A47G 9/10
USPC ............ 5/721, 726–727, 421, 657, 636, 630
See application file for complete search history.

(56) References Cited

U.S. PATENT DOCUMENTS 4,884,304 A  12/1989  Elkins
4,896,388 A  1/1990  Bard
(Continued)

FOREIGN PATENT DOCUMENTS

WO  2011/161571 A1  12/2011

OTHER PUBLICATIONS

"The Digital Pillow," www.thedigitalpillow.com (published Jan. 2014, Apr. 2014, Jun. 2014, Jul. 2014, Nov. 2014, Aug. 2015).

*Primary Examiner* — Fredrick C Conley
(74) *Attorney, Agent, or Firm* — Rosenberg, Klein & Lee

(57) ABSTRACT

An electronically controllable pillow is thermally regulated. At least one temperature sensor is configured to communicate temperature measurements. Temperature measurements comprise the internal temperature of a pillow. Temperature measurements are communicated to a processing unit. At least one presence sensor is configured to communicate presence measurements. Presence measurements are configured to indicate the presence of a user employing a pillow. Presence measurements are communicated to a processing unit. At least one transceiver is connected to a processing unit. A transceiver is configured to communicate with at least one remote device. At least one thermal element is activated, based at least in part on, temperature measurements and presence measurements over at least one period of time.

20 Claims, 34 Drawing Sheets

Related U.S. Application Data

(60) Provisional application No. 62/046,304, filed on Sep. 5, 2014.

(51) Int. Cl.

| | |
|---|---|
| *A61M 21/02* | (2006.01) |
| *A61B 5/00* | (2006.01) |
| *A61F 7/02* | (2006.01) |
| *A61F 7/00* | (2006.01) |
| *A61B 5/01* | (2006.01) |
| *A61M 21/00* | (2006.01) |
| *A61B 5/103* | (2006.01) |

(52) U.S. Cl.
CPC ............ *A61M 2205/0294* (2013.01); *A61M 2205/3303* (2013.01); *A61M 2205/3355* (2013.01); *A61M 2205/3372* (2013.01); *A61M 2205/3375* (2013.01); *A61M 2205/3561* (2013.01); *A61M 2205/3584* (2013.01); *A61M 2205/42* (2013.01); *A61M 2205/50* (2013.01); *A61M 2205/502* (2013.01); *A61M 2205/52* (2013.01); *A61M 2205/8206* (2013.01); *A61M 2230/06* (2013.01); *A61M 2230/40* (2013.01); *A61M 2230/50* (2013.01); *A61M 2230/63* (2013.01)

(56) References Cited

U.S. PATENT DOCUMENTS

| | | |
|---|---|---|
| 4,989,283 A | 2/1991 | Krouskop |
| 5,429,762 A | 7/1995 | Kitahara et al. |
| 6,253,818 B1 | 7/2001 | Hughes |
| 8,170,685 B2 | 5/2012 | Docherty et al. |
| 8,316,649 B2 | 11/2012 | Wolske |
| 2003/0047301 A1 | 3/2003 | Ichigaya |
| 2003/0159219 A1 | 8/2003 | Harrison et al. |
| 2004/0177449 A1* | 9/2004 | Wong .................. A47C 27/082 5/713 |
| 2007/0261414 A1 | 11/2007 | Polder |
| 2008/0083721 A1 | 4/2008 | Kaiserman et al. |
| 2010/0018684 A1 | 1/2010 | Tani |
| 2010/0170043 A1* | 7/2010 | Young .................. A47C 27/082 5/706 |
| 2011/0302720 A1 | 12/2011 | Yakam et al. |
| 2012/0198616 A1 | 8/2012 | Makansi et al. |
| 2013/0008181 A1 | 1/2013 | Makansi et al. |
| 2013/0035541 A1 | 2/2013 | Kashima et al. |
| 2013/0218244 A1 | 8/2013 | Iwanami et al. |
| 2014/0008036 A1 | 1/2014 | Segal |
| 2014/0109318 A1 | 4/2014 | Loos |
| 2015/0033474 A1* | 2/2015 | Mikkelsen ........... A47G 9/1036 5/421 |
| 2015/0366365 A1 | 12/2015 | Golin et al. |
| 2016/0015183 A1* | 1/2016 | Stjerna ................ A47C 23/0435 5/727 |

\* cited by examiner

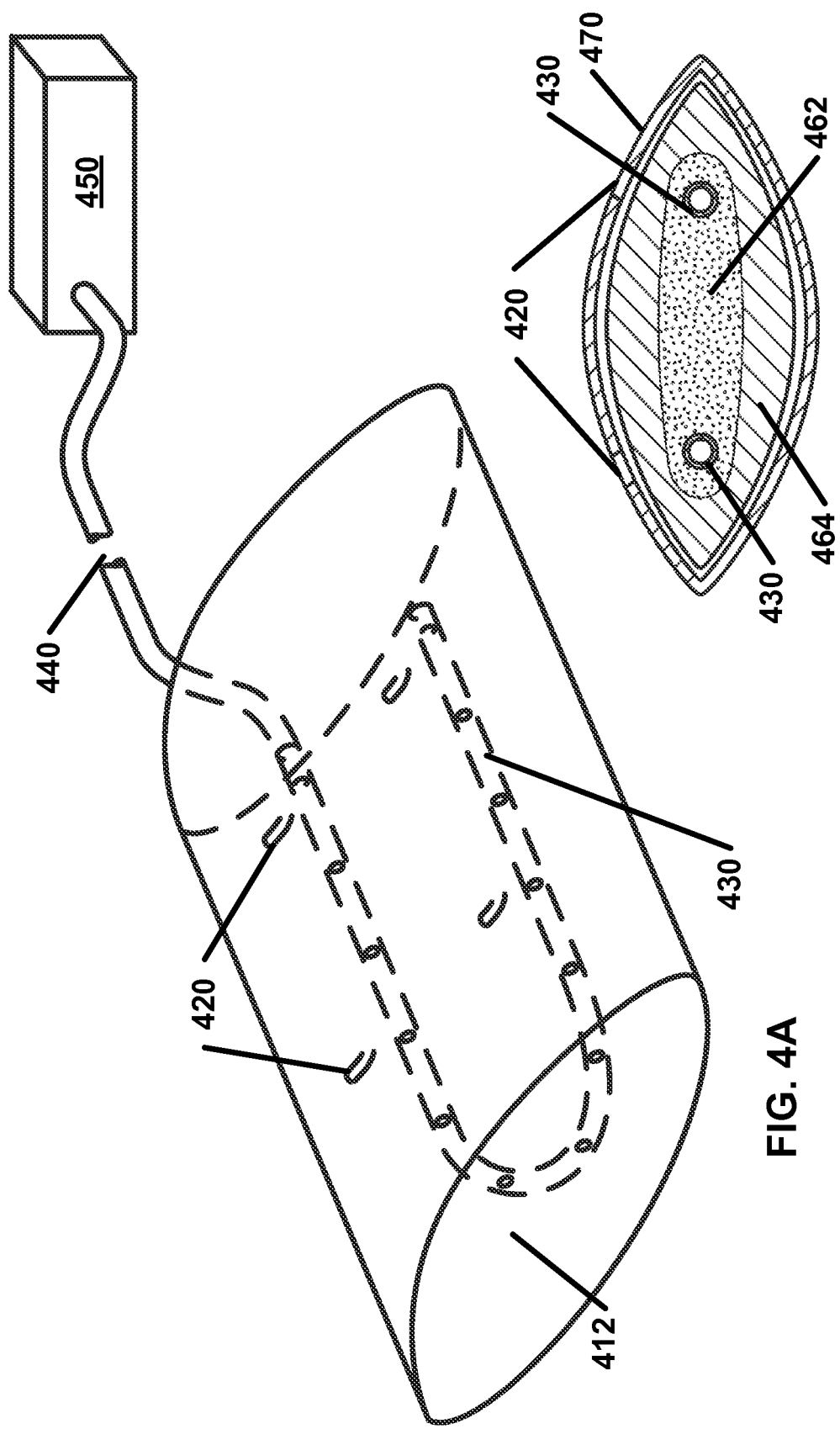

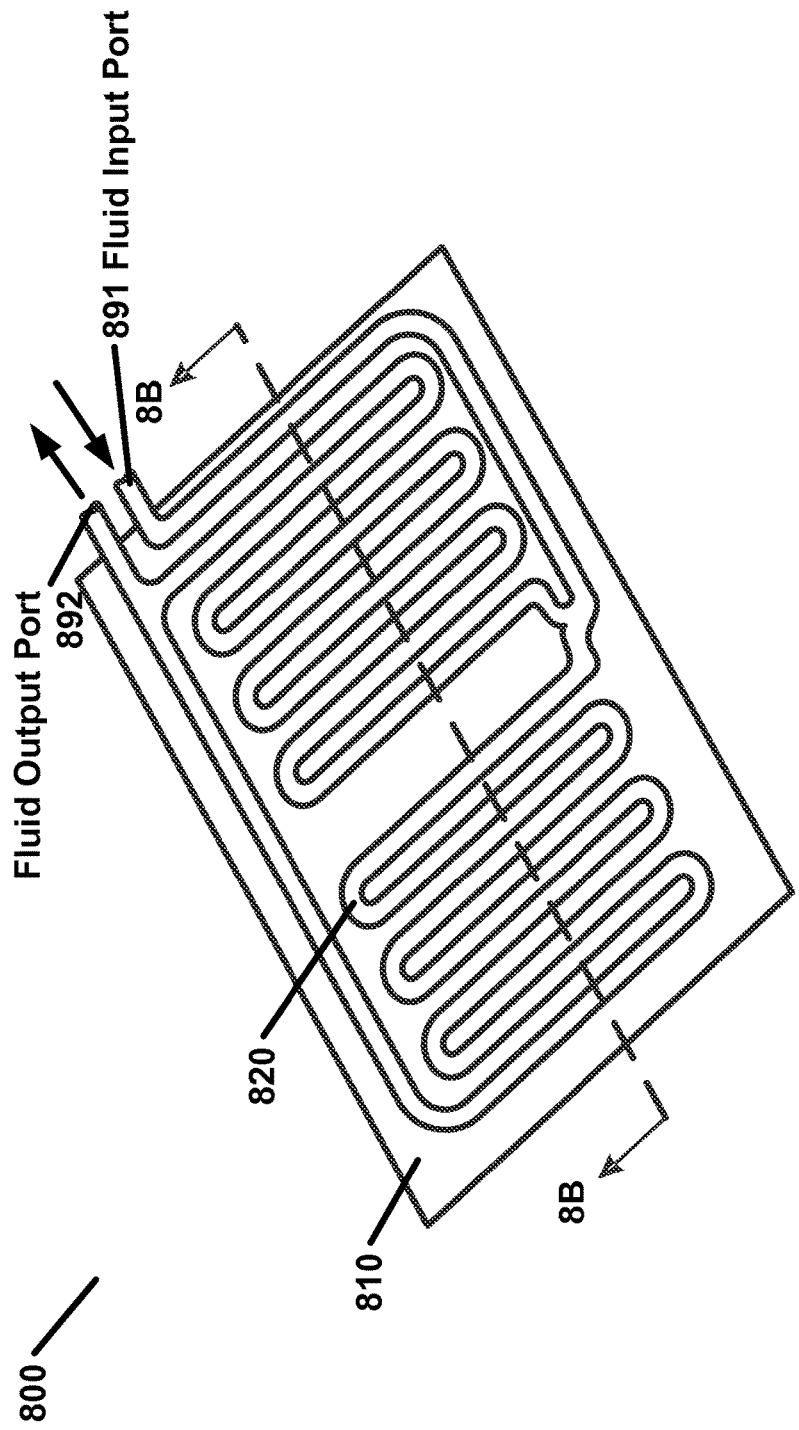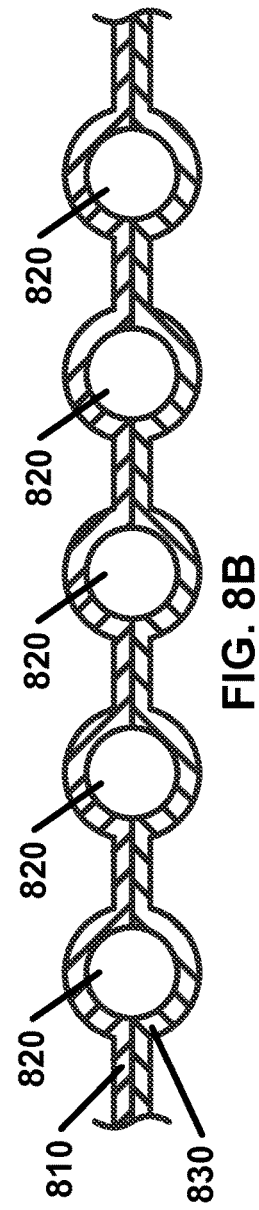

US 10,820,728 B1

ELECTRONICALLY CONTROLLABLE PILLOW

RELATED PATENT APPLICATION DATA

This is a Continuation of U.S. patent application Ser. No. 14/846,765, entitled "ELECTRONICALLY CONTROLLABLE PILLOW," filed 5 Sep. 2015, currently pending.

BACKGROUND

Sleeping conditions that are too hot or too cold may lead to a restless night. Memory foam materials have become popular in the art for support and comfort. However, memory foam may trap additional heat over more traditional materials. More advanced memory foam pillows comprising a cooling mat or microfiber beads may dissipate heat more efficiently, however, these solutions may only be limited in the length of time that they stay cool (e.g. up to approximately 4 hours). A restful night may require 6-9 hours of undisturbed sleep. Alternatively, memory foam materials may not trap enough heat consistently throughout a sleeping session in cold environments for some users.

A pillow that is not set to a comfortable height for a user may lead to a restless night. Some of the advanced memory foam pillows that have been developed in the art provide for additional layers that are inserted into or below the pillow for additional height. Other advanced memory foam pillows that have been developed in the art provide for interchangeable cores of various heights. However, the layers and cores only provide a small number of fixed heights. These pillows are unable to achieve a comfortable height for many users.

BRIEF DESCRIPTION OF THE SEVERAL VIEWS OF THE DRAWINGS

FIGS. 4A and 4B are illustrations of an example electronically controllable pillow with at least one porous material as per an aspect of various embodiments

FIGS. 8A and 8B are illustrations of an example thermal element according to an aspect of various embodiments.

DETAILED DESCRIPTION OF EMBODIMENTS

At least some of the various embodiments thermally regulate at least one electronically controllable pillow. Different people may require different amounts of cooling or heating to attain restful sleep. Therefore, feedback on how the temperature is affecting the user may provide more restful sleep.

At least some of the various embodiments regulate the height of at least one electronically controllable pillow. Different people may require different pillow heights to attain restful sleep. Therefore, feedback on how the height of a pillow is affecting the user may provide more restful sleep.

Figure 1:
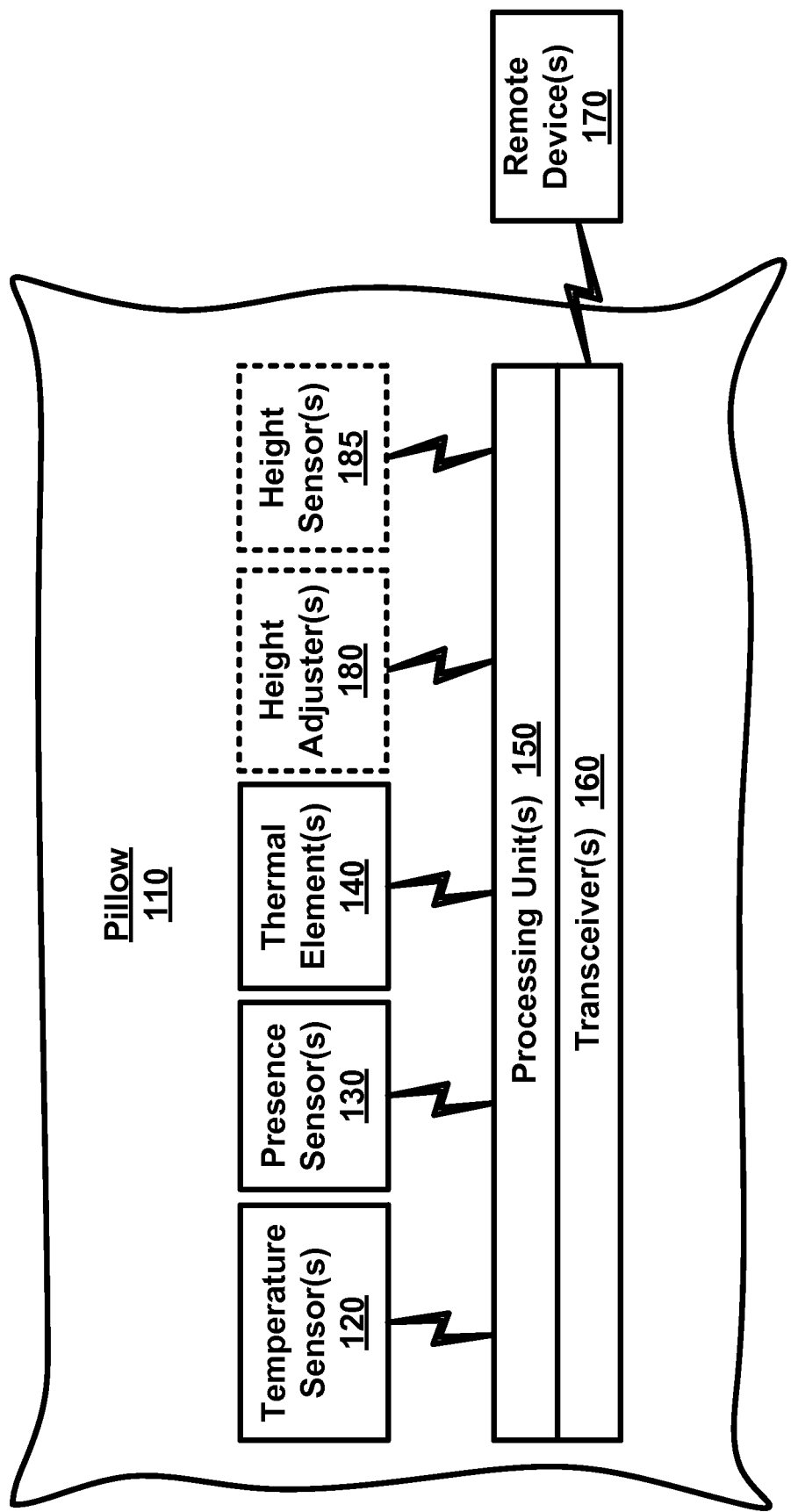
FIG. 1 is an example block diagram showing elements of an electronically controllable pillow as per an aspect of various embodiments.

FIG. 1 is an example block diagram showing elements of an electronically controllable pillow comprising a pillow 110 as per an aspect of an embodiment. The electronically controllable pillow may further comprise one or more temperature sensors 120, one or more presence sensors 130, and one or more thermal elements 140 according to some of the various embodiments. The electronically controllable pillow may, for example, further comprise one or more pillow height adjusters 180 and one or more pillow height sensors 185. According to some of the various embodiments, the electronically controllable pillow may comprise one or more processing units 150 and one or more transceivers 160. The one or more processing units 150 may, for example, be configured to communicate with one or more temperature sensors 120, one or more presence sensors 130, and one or more thermal elements 140. The one or more processing units 150 may, for example, be further configured to communicate with one or more pillow height adjusters 180 and one or more pillow height sensors 185. The one or more transceivers 160 may, for example, be configured to communicate with one or more remote devices 170.

By way of example and not limitation, the electronically controllable pillow may comprise one or more presence sensors 130, one or more pillow height adjusters 180, one or more pillow height sensors 185, one or more processing units 150, and one or more transceivers 160. The one or more transceivers 160 may, for example, be configured to communicate with one or more remote devices 170. This example embodiment illustrates an electronically controllable pillow configured to adjust the height of the pillow 110.

Figure 2:
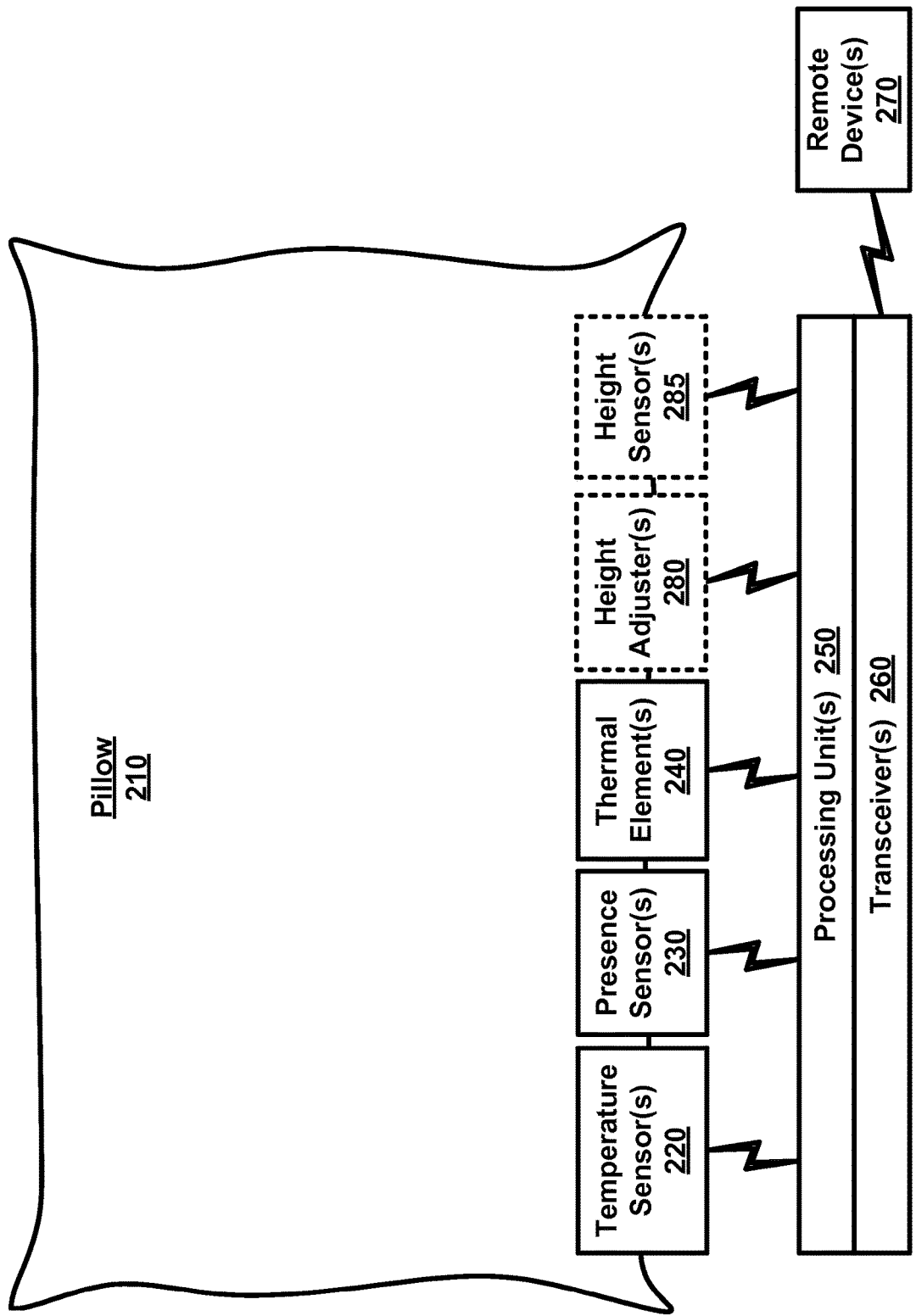
FIG. 2 is an example block diagram showing elements of an electronically controllable pillow as per an aspect of various embodiments.

The example shown in FIG. 1 comprises elements disposed internal to the pillow 110. FIG. 2 is an example block diagram showing similar elements of the electronically controllable pillow illustrated in FIG. 1. The elements in FIG. 2 correspond in number to the similar elements in FIG. 1. In the example shown in FIG. 2, one or more of the following elements may be disposed external to the pillow 210: the one or more temperature sensors 220, the one or more presence sensors 230, the one or more thermal elements 240, the one or more pillow height adjusters 280, and the one or more pillow height sensors 285. In this example, the one or more processing units 250 and the one or more transceivers 260 may be externally disposed to the pillow 210. The transceivers 260 may be configured to communicate with one or more external devices 270. External devices 270 may comprise a monitoring and/or controlling device.

Figure 3:
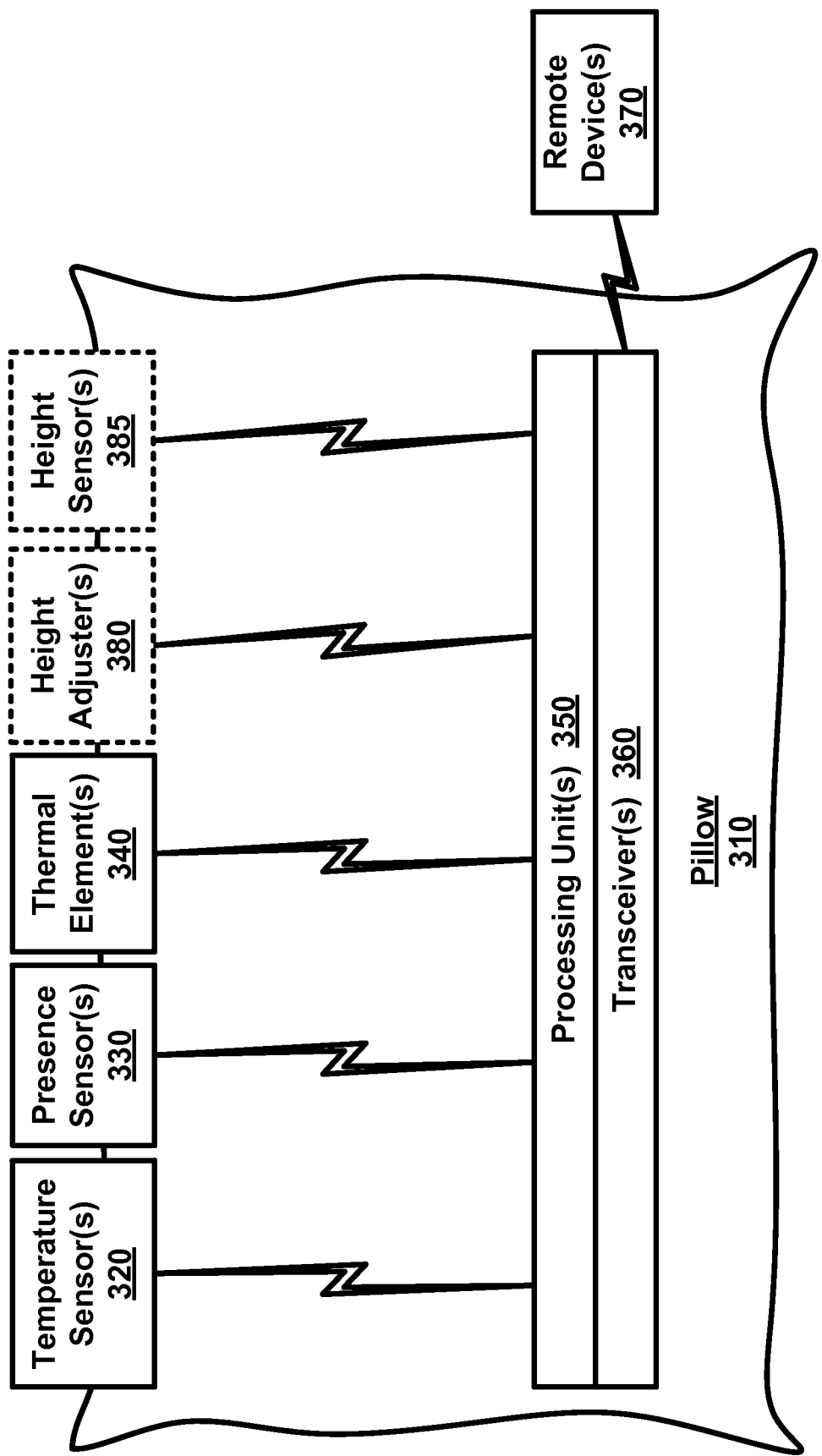
FIG. 3 is an example block diagram showing elements of an electronically controllable pillow as per an aspect of various embodiments.

Similarly, FIG. 3 is an example block diagram showing similar elements of the electronically controllable pillow in FIG. 1 and in FIG. 2. The elements in FIG. 3 correspond in number to the similar elements in FIG. 1 and in FIG. 2. In the example shown in FIG. 3, one or more of the following elements may be disposed external to the pillow 310: one or more temperature sensors 320, one or more presence sensors 330, one or more thermal elements 340, one or more pillow height adjusters 380, and one or more pillow height sensors 385. In this example, the one or more processing units 350 and the one or more transceivers 360 may be internally disposed to the pillow 310. The transceivers 360 may be configured to communicate with one or more external devices 370. External devices 370 may comprise a monitoring and/or controlling device.

Some of the various embodiments may include an apparatus comprising a pillow. The pillow may comprise materials. The materials may, for example, comprise memory foam, high density foam, open cell foam, reticulated foam, natural fabric, synthetic fabric, insulation, a combination thereof, and/or the like. At least one of the materials may be treated to be hydrophobic. At least one of the materials may comprise anti-microbial additives. Treated materials may be configured to prevent growth of harmful microorganisms (e.g. mold or mildew). At least one of the materials may be porous to allow for exchange of air, water vapor, gas(es), combinations thereof, and/or the like. Air, water vapor, and/or gas(es) may be distributed throughout at least a portion of the pillow. For example, the pillow may be configured to accept dehumidified air. The dehumidified air may be employed to remove moisture, facilitate heat transfer, provide at least part of some convection, combinations thereof, and/or the like. According to some of the various embodiments, the air, water vapor, and/or gas(es) may be accepted at a low flow rate.

FIGS. 4A and 4B illustrate an example electronically controllable pillow 412 with at least one porous material as per an aspect of various embodiments. Air, water vapor, and/or gas(es) may be distributed throughout at least a portion (e.g. 462,464) of the pillow 412 via at least one perforated tubing 430. The at least one perforated tubing 430 may be flexible, semi-rigid, rigid, combinations thereof, and/or the like. According to some of the various embodiments, at least one of the materials (e.g. 464 or 470) may be non-permeable. The non-permeable material may, for example, comprise at least one defined exit (e.g. 420) for accepted air, water vapor and/or gas(es). At least part of the at least one defined exit (e.g. 420) may, for example, be configured to direct air, water vapor and/or gas(es) through an outer surface 470 of the pillow. The at least one defined exit (e.g. 420) may be configured to direct air, water vapor and/or gas(es) towards and/or away from an intended user. The air, water vapor, and/or gas(es) may be accepted via at least one tube (e.g. 440) from a remote enclosure 450. The remote enclosure 450 may be configured with air quality and movement devices to vary the moisture content, pressure, and/or flow rate of the air, water vapor, and/or gas(es). The air quality and movement devices may comprise without limitation: pumps, control electronics, filters, air dryers, combinations thereof, and/or the like. The air, water vapor, and/or gas(es) may comprise at least one substance intended for aromatherapy. The at least one substance may be delivered to the pillow 412 based at least in part on the presence of a user, a user input (i.e. preference), at least one sleeping session, at least one interruption event, at least one sleep cycle phase, at least one sleep cycle number, combinations thereof, and/or the like.

Figure 5A:
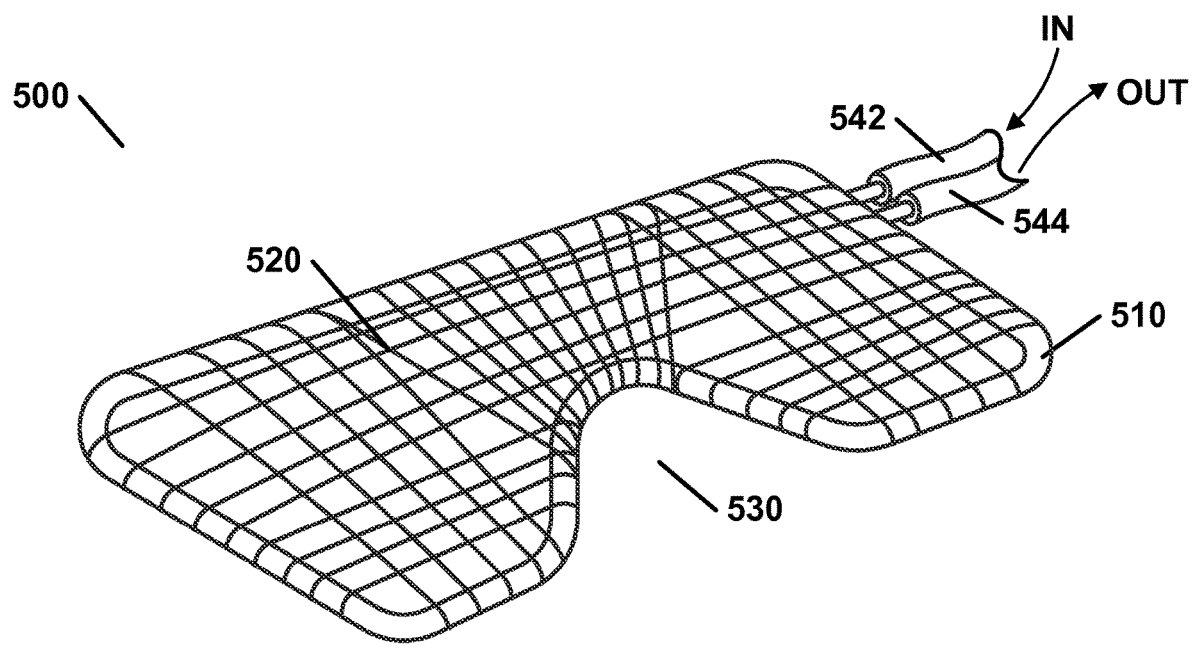
FIGS. 5A and 5B are illustrations of an example support structure for an electronically controllable pillow.
Figure 5B:
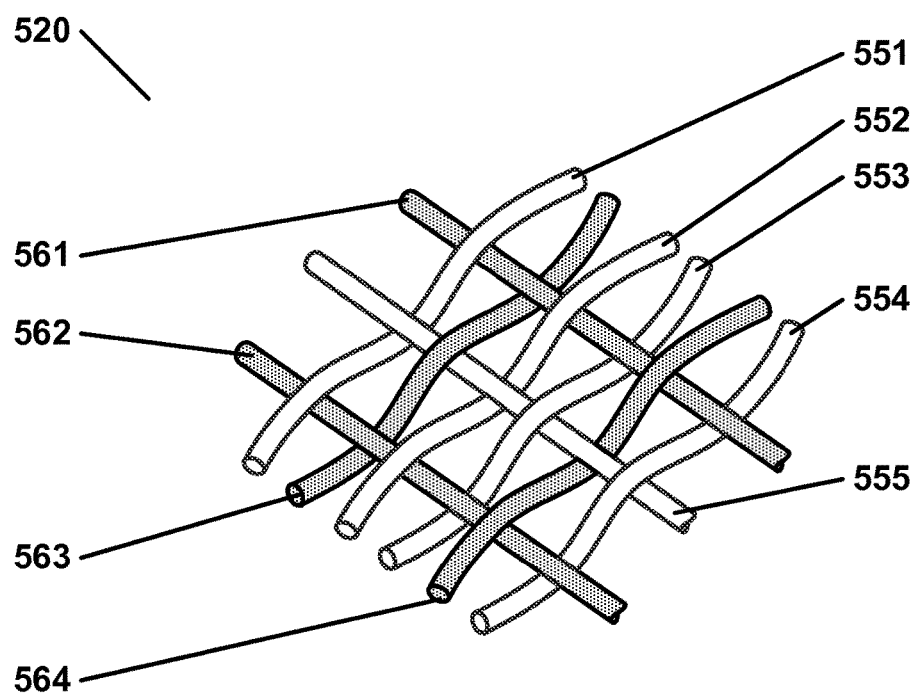

FIGS. 5A and 5B illustrate an example support structure 500 for an electronically controllable pillow. The support structure 510 may comprise a rigid structural tube element 510. The rigid structural tube element 510 may be formed to follow at least a portion of a perimeter of the pillow. The rigid structural tube element 510 may comprise a highly thermally conductive material. The rigid structural tube element 510 may be configured to carry liquids, gels, air, and/or gases. At least one material (e.g. 520) may be suspended from the rigid structural tube element 510. The support structure 500 may comprise a relief section 530 at a center portion along one side of the support structure 500. The relief section 530 may be configured to accommodate a shoulder of a user. Alternatively, the support structure 500 may comprise a plurality of tube elements. At least one of the plurality of tube elements may be configured to support a head of a user. At least one of the plurality of tube elements may be configured to support a neck of a user. At least one tube element may comprise at least one quick disconnect fitting. The at least one quick disconnect fitting may be located along a left edge of the pillow (e.g. 210, 310), along a right edge of the pillow (e.g. 210, 310), along a top edge of the pillow (e.g. 210, 310), combinations thereof, and/or the like. Each of the at least one quick disconnect fitting may be configured to accept a tube (e.g. 542, 544) from the remote enclosure. The at least one material (e.g. 520) may comprise a plurality of materials. At least one first material (e.g., 561, 562, 563, and/or 564) of the plurality of materials may, for example, comprise a resilient strand and/or an elastic member configured to support an object (e.g. a head of a user) while providing some suspension. At least one second material (e.g. 551, 552, 553, 554, and/or 555) of the plurality of materials may, for example, comprise a thermally conductive material configured to add and/or remove heat from an object (e.g. a head of a user).

Figure 6:
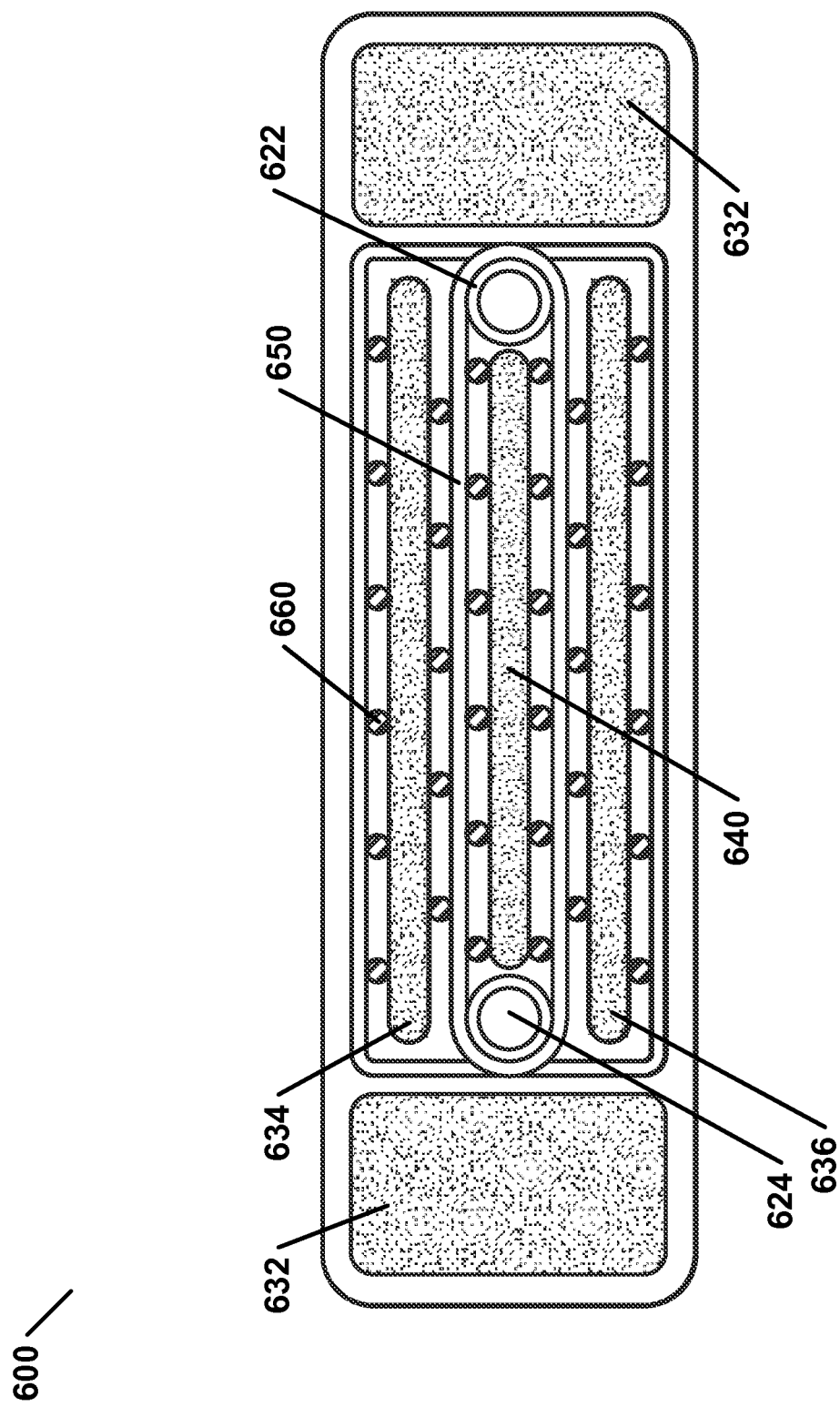
FIG. 6 is an illustration of a cross-section of an example of an electronically controllable pillow.

FIG. 6 illustrates a cross-section 600 of an example of an electronically controllable pillow. The cross-section of pillow 600 may comprise a tube element 624. The tube element 624 may comprise a highly thermally conductive material(s) 622. The tube element 624 may be configured to suspend at least one first material(s) 650. The at least one first material(s) 650 may be separated and/or partially supported by at least one second material(s) 640. Cross-sections of at least part of woven material(s) 660 may comprise the at least one first material(s) 650. Although only one example woven material(s) 660 is labeled for clarity sake, all similar graphical items in FIG. 6 also illustrate example woven material(s) 660. Cross-sections of at least part of woven material(s) 660 may comprise a thermally conductive material(s) as described previously. The cross-sections of woven material(s) 660 may be separated and/or partially supported by at least one third material(s) 634 and/or one at least one fourth material(s) 636. Pillow 600 may further comprise at least one fifth material(s) 632. Any of the at least one second material(s) 640, the at least one third material(s) 634, the at least one fourth material(s) 636, and/or the at least one fifth material(s) 632 may comprise the same material(s).

The pillow may, for example, further comprise at least one chamber. As described by various embodiments, the chamber may be insulated. Furthermore, the pillow may, for example, comprise a plurality of chambers. At least two of the plurality of chambers may, for example, be superimposed on each other, adjacent to each other, structurally independent, a combination thereof, and/or the like. According to some of the various embodiments, some chambers may be internal to the pillow. In yet other embodiments, some chambers may be external to the pillow. An external chamber may be disposed along one or more sides of the pillow. For example, an external chamber may be disposed on the underside of a pillow.

According to some of the various embodiments, an apparatus may, for example, be configured to transfer warm liquid, gel, air, gas, a combination thereof, and/or the like between a pillow and an external enclosure via at least one chamber. An apparatus may, for example, be configured to transfer cold liquid, gel, air, gas, a combination thereof, and/or the like between a pillow and an external enclosure via at least one chamber. The pillow may, for example comprise at least one chamber filled with at least one liquid, gel, air, gas, a combination thereof, and/or the like. The pillow may, for example, further comprise at least one chamber filled with a viscoelastic gel.

According to some of the various embodiments, an apparatus may comprise a power source. By way of example and not limitation, the power source may comprise at least one of the following: an electric outlet providing alternating current, at least one battery providing direct current, a solar panel configured to charge at least one battery, a generator providing at least one of alternating and direct current, a combination thereof, and/or the like. One or more of the various embodiments may, for example, further comprise a power switch. The power switch may, for example, be configured to provide at least one of the following modes: power off, heating only, cooling only, thermal regulation, a combination thereof, and/or the like. The thermal regulation mode may, for example, comprise heating and cooling functions. The apparatus may, for example, further comprise a converter of at least one of voltage and current.

According to some of the various embodiments, an apparatus may comprise a processing unit 150. The at least one processing unit 150 may, for example, comprise a computing device, a smart device, a microcontroller, a microprocessor system, a combination thereof, and/or the like. A processing unit 150 may include hardware configured to execute the instructions of a computer program by performing the basic arithmetical, logical, and input/output operations within a system. In some embodiments, a processing unit 150 may comprise a central processing unit (CPU) with associated hardware (e.g. power, input/output, data bus interface, display, etc.). In other embodiments, a processing unit 150 may comprise a microcontroller.

A microcontroller (sometimes abbreviated μC, uC or MCU) may comprise a small computer on a single integrated circuit containing a processor core, memory, and programmable input/output peripherals. Example microcontrollers comprise, but are not limited to: an Intel 8051 family microcontroller, a Freescale 6811 family microcontroller, an ARM Cortex-M family core processor, an Atmel AVR family microcontroller, a STMicroelectronics STM32 microcontroller, and/or the like.

Some of the various embodiments may include at least one temperature sensor 120. At least one temperature sensor 120 may comprise a converter device configured to measure a physical temperature quantity and convert it into a representation that may be read by an observer or by an observer device. For example, a thermocouple may convert temperature to an output voltage. Alternatively, a thermistor may, for example, convert changes in temperature to changes in resistance in an electrical circuit. The electrical circuit may be configured to convert changes in resistance to an output voltage or an output current. The output voltage and/or the output current may be converted by an analog to digital converter into a digital representation of the temperature. The digital representation may be read and/or processed by a device such as, for example, processing unit 150. For accuracy, some temperature sensors may be calibrated. At least one of the at least one temperature sensor 120 may be configured to measure at least one temperature of at least one thermal element 140. At least one of the at least one temperature sensor 120 may be configured to estimate at least one temperature of a user of the pillow 110. The at least one temperature sensor may be configured to communicate temperature measurements. At least one of the at least one temperature sensor 120 may be configured to detect the presence of the user. A plurality of temperature sensors 120 may be employed to detect the presence of the user in at least one of a plurality of defined zones of the pillow 110. The at least one temperature sensor 120 may be configured to communicate presence measurements.

According to some of the various embodiments, the temperature measurements may be communicated according to a clock, at intervals required by a processing unit, at intervals required by a transceiver (e.g. 160), at intervals specified by a remote device, at intervals specified by a second apparatus, at intervals selected by the user, a combination thereof, and/or the like. The temperature measurements may, for example, comprise the internal temperature of the pillow. The at least one temperature sensor 120 may, for example, communicate temperature measurements to the at least one processing unit 150. According to some of the various embodiments, at least one of the at least one temperature sensor 120 may, for example, be disposed inside the pillow. Alternatively, at least one of the at least one temperature sensor 120 may, for example, be disposed outside the pillow. In this example, the temperature sensor 120 may be configured to communicate temperature measurements of the external temperature of the pillow 110. According to some of the various embodiments, the temperature measurements may comprise differential temperature measurements, relative temperature measurements, absolute temperature measurements, a combination thereof, and/or the like. The absolute temperature measurements may comprise degrees Celsius, degrees Fahrenheit, a combination thereof, and/or the like.

Some of the various embodiments may include at least one presence sensor 130. A presence sensor 130 is a device configured to detect the absence or presence of an object (e.g. a head of a user). A presence sensor 130 may need to be strategically located to identify the presence (or lack thereof) of an object in a particular location. Examples of presence sensor 130 include, but are not limited to: weight sensors, temperature sensors, inductive proximity sensors, capacitive proximity sensors, ultrasonic sensors, photoelectric sensors, thermal imaging sensors, motion sensors, combinations thereof, and/or the like. According to some of the various embodiments, at least one presence sensor 130 may be communicatively coupled to at least one wearable. For example, pillow 110 may be configured to warn a user wearing at least one wrist wearable when the at least one wrist wearable contacts the pillow 110.

Figure 7:
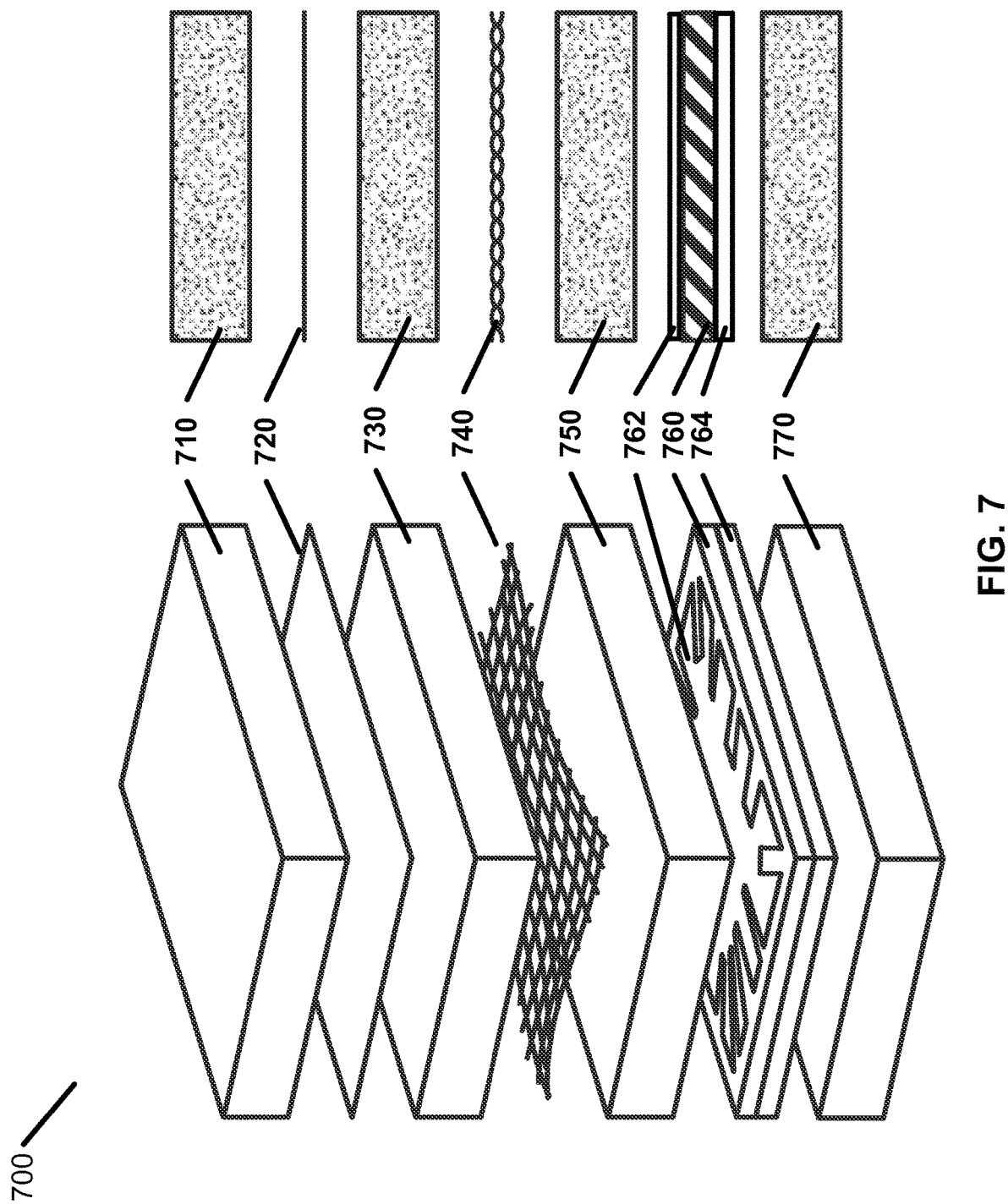
FIG. 7 is an illustration of an example capacitive proximity sensor according to an aspect of various embodiments.

FIG. 7 illustrates an example capacitive proximity sensor 700 according to an aspect of various embodiments. The capacitive proximity sensor 700 may comprise a layer of woven fiber mesh 740. The woven fiber mesh 740 may be electrically conductive and configured to provide a grounding plane. The woven fiber mesh 740 may be surrounded by at least one material (e.g. 730, 750). The capacitive proximity sensor 700 may further comprise at least one antenna 762. The at least one antenna 762 may comprise a layer of antenna elements. The capacitive proximity sensor 700 may further comprise at least one shielding layer 764. The at least one antenna 762 may be separated from the at least one shielding layer 764 by at least one substrate 760. Shielding layer 764 may be disposed adjacent to an outer material 770. The at least one substrate may comprise at least one material. The capacitive proximity sensor 700 may further comprise at least capacitive circuit. The at least one antenna 762 may be electrically coupled to the woven fiber mesh 740 via the at least one capacitive circuit. The woven fiber mesh 740 may be isolated from the at least one antenna 762 by at least one non-conductive compressible material (e.g. 750) located in between the woven fiber mesh 740 and the at least one antenna 762. In this example, the presence of an object (e.g. head of a user) may be detected when the distance between the woven fiber mesh 740 and the at least one antenna 762 is reduced. The distance may be reduced when the weight of the object compresses the at least one non-conductive compressible material (e.g. 750). The capacitive proximity sensor may further comprise at least one shielding layer 720. The at least one shielding layer 720 may be surrounded by at least one material (e.g. 710, 730). The at least one shielding layer 720 may be employed to shield the capacitive proximity sensor from electrical signals that may be emitted from devices including but not limited to: temperature sensors 120, processing units 150, transceivers 160, remote devices 170, combinations thereof, and/or the like.

According to some of the various embodiments, the presence sensor 130 may be configured to communicate presence measurements. The measurements may be communicated according to a clock, at intervals compatible with a processing unit (e.g. 150), at intervals compatible with by a transceiver (e.g. 160), at intervals compatible with a remote device (e.g. 170), at intervals specified by a second apparatus, at intervals selected by the user, a combination thereof, and/or the like. The presence measurements may, for example, indicate the presence of a user employing the pillow. The presence sensor 130 may also, for example, communicate presence measurements to the at least one processing unit 150.

According to some of the various embodiments, the capacitive proximity sensor may be configured to produce presence measurements comprising surface area measurements. The surface area measurements may comprise an estimated amount of a surface area of the pillow 700 in contact with a user. Furthermore, a plurality of antennas 762 and a plurality of capacitive circuits may be employed to detect presence in each of a plurality of pillow zones. Each of the plurality of antennas 762 may be electrically coupled to the woven fiber mesh 740 via one of the plurality of capacitive circuits. Presence on at least one of a plurality of pillow zones may be employed to estimate a position of a user (e.g. lying supine, lying prone, lying on side, lying on right side, lying on left side). Alternatively, the capacitive proximity sensor may comprise a vertical layer of woven fiber mesh configured to provide a vertical grounding plane near the bottom edge (i.e. towards a user) of the pillow. The vertical woven fiber mesh may be electrically coupled to a plurality of vertical antennas via a plurality of capacitive circuits. The vertical woven fiber mesh and the plurality of vertical antennas may be employed to estimate a position of a user (e.g. lying supine, lying prone, or lying on side). Estimating the position of a user may require user calibration. Persons skilled in the art will recognize that a capacitive proximity sensor may be constructed in a variety of ways with a variety of grounding planes, a variety of antennas, and a variety of circuit elements.

According to some of the various embodiments, at least one presence sensor (e.g. 130) may, for example, comprise at least one piezoelectric element, at least one strain gauge, at least one optical fiber, at least one micro camera, a combination thereof, and/or the like. The at least one presence sensor (e.g. 130) may, for example, comprise a plurality of strain gauges, each of the plurality of strain gauges in a distinct location. The plurality of strain gauges may be collectively configured to detect deflection in a plurality of directions. Detection in a plurality of directions may enable detection of user presence or absence as well as an estimation of a position of a user (e.g. lying supine, lying prone, or lying on side). Estimating the position of a user may require user calibration. The presence sensor (e.g. 130) may, for example, comprise at least one pressure sensor, at least one motion sensor, at least one location sensor, at least one accelerometer, a combination thereof, and/or the like.

According to some of the various embodiments, a pressure sensor may, for example, be configured to detect presence by sensing backpressure in a tube or line configured to deliver liquids, gels, air, gas, a combination thereof, and/or the like to the pillow. For example, when a human head contacts the pillow, the at least one pressure sensor may be configured to determine a change in flow rate or line pressure beyond a predetermined threshold. The change in flow rate or line pressure beyond a predetermined threshold may be utilized to determine the presence or absence of an object (e.g. a head of a user) on the pillow. The pressure sensor may require calibration configured to determine a pressure baseline. The processing unit (e.g. 150, 250, 350) may be configured to run a calibration process on a specific time interval, during presence of a user on the pillow (e.g. 110, 210, 320), during absence of a user on the pillow, combinations thereof, and/or the like. The at least one processing unit (e.g. 150, 250, 350) may be configured to remove noise signals in the measurements produced by the pressure sensor during movement of the user. For example, the at least one processing unit (e.g. 150, 250, 350) may be configured to discard presence measurements prior to a specific amount of time and/or a specific amount of measurements after changes in pressure are determined. Alternatively, the at least one processing unit (e.g. 150, 250, 350) may, for example, be configured to take an average of pressure measurements and/or a weighted average of measurements. The predetermined threshold may be based at least in part on at least one user calibration routine.

According to some of the various embodiments, the location sensor may, for example, employ Wi-Fi, GPS, differential GPS, at least one cellular data channel, a combination thereof, and/or the like. The presence sensor may, for example, be configured to detect shoulder blade movement in the user. Shoulder blade movement may, for example, be used to detect breathing patterns of the user. The breathing patterns of the user may, for example, be utilized in determining a recommended temperature, height, number of sleep cycles, wake time, a combination thereof, and/or the like. Breathing patterns may be detected at least in part through employment of at least one wearable sensor. The at least one wearable sensor may be configured to measure heart rate, heart rate variability, sympathetic tone, movement, location, airflow, combinations thereof, and/or the like.

Some of the various embodiments may include at least one transceiver 160. A transceiver 160 may comprise a device that includes both a transmitter and a receiver. The transmitter and receiver may be combined, may share common circuitry, may share a single housing, combinations thereof, and/or the like. When no circuitry is common between transmit and receive functions, a transceiver 160 may be referred to as a transmitter-receiver.

The at least one transceiver 160 may, for example, connect to the at least one processing unit 150. The transceiver 160 may also, for example, be configured to communicate with at least one remote device 170. According to some of the various embodiments, the transceiver 160 may employ at least one of the following communication mechanisms: a wired communications mechanism, a wireless communications mechanism, Ethernet, Wi-Fi, Bluetooth, ZigBee, a Wireless Personal Area Network (WPAN), Near Field Communications (NFC), an infrared connection, a combination thereof, and/or the like. The wired communications mechanism may comprise an external connector. The remote device 170 may, for example, comprise a computing device, a server, a SaaS, a mobile device, a remote control, a wearable device, another apparatus, a combination thereof, and/or the like. A mobile device may comprise, for example, a phone, a tablet, a notebook, and combination thereof, and/or the like.

Some of various embodiments may include at least one thermal element 140. A thermal element 140 may comprise a device that is configured to change temperature. Some thermal elements 140 may be configured to change temperature by moving and/or transferring heat towards or away from a location. An example of such a device is a heat pump which may transfer heat from one side of a device to the other side of a device. Some thermal elements 140 may generate heat by, for example, converting electricity into heat through the process of resistive or Joule heating in which electric current passing through the element encounters resistance, resulting in heating of the element. Other thermal elements 140 may cool a location employing, for example, a thermoelectric cooling device, a fan, a combination thereof, and/or the like.

The at least one thermal element 140 may, for example, be activated based, at least in part, on measurements comprising temperature, presence, combinations thereof, and/or the like. The at least one thermal element 140 may, for example, electrically couple to processing unit 150. According to some of the various embodiments, the at least one thermal element 140 may employ at least one of the following to modify the temperature of the pillow: direct heat, at least one warm gas (e.g. air), at least one warm liquid, at least one warming gel, at least one cold gas (e.g. air), at least one cool liquid, at least one cooling gel, a combination thereof, and/or the like. According to some of the various embodiments, the thermal element may comprise at least one of the following: at least one coil configured to circulate liquid or gel, at least one coil configured to circulate gas, at least one tube configured to circulate liquid or gel, at least one tube configured to circulate gas, at least one chemical cell, at least one metal wire, at least one metal sheet, at least one metal rod, a combination thereof, and/or the like. The at least thermal element may be located in the pillow, in a remote enclosure, coupled to the pillow and remote enclosure, combinations thereof, and/or the like. The at least one coil and/or at least one tube may, for example, be configured to deliver warm and/or cold gas to a porous membrane. The porous membrane may be configured to enable warm and/or cold gas to propagate through at least a portion of the pillow via at least one porous material. The at least one coil and/or at least one tube may, for example, be perforated.

FIGS. 8A and 8B illustrate an example of a thermal element 800 according to an aspect of various embodiments. Thermal element 800 may comprise at least one tube 820. The at least one tube 820 may be employed to circulate at least one liquid, gel, air, and/or gas through at least a portion of a pillow. Thermal element 800 may comprise flexible and/or resilient properties. Thermal element 800 may, for example, comprise a blow molded or twin sheet formed part comprising hollow conduits 820. Sheets 810 and 830 may be bonded together to form the thermal element 800. The hollow conduits 820 may, for example, be arranged in a series of parallel runs in a planar fashion. Thermal element 800 may further comprise input port 891 to accept at least one liquid, gel, air, and/or gas and output port 892 configured to return at least one liquid, gel, air, and/or gas.

Figure 9A:
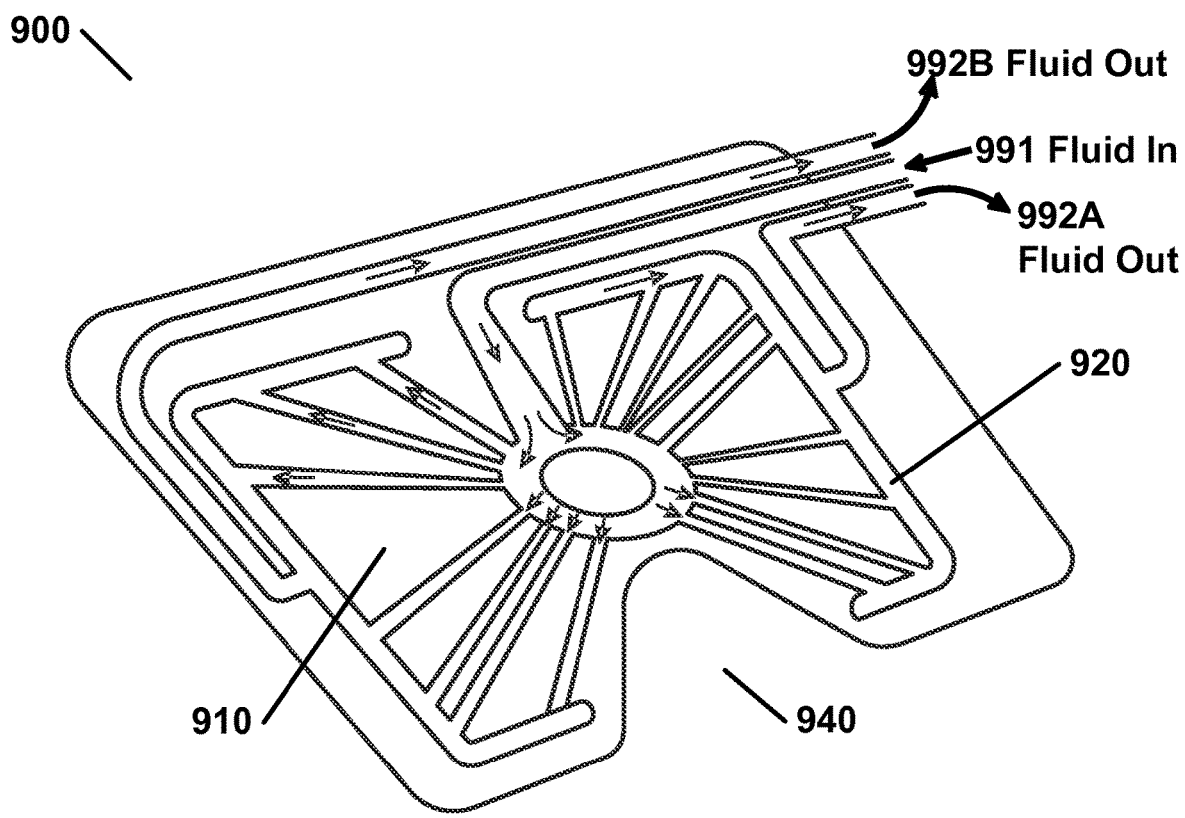
FIGS. 9A and 9B are illustrations of an example thermal element according to an aspect of various embodiments.
Figure 9B:
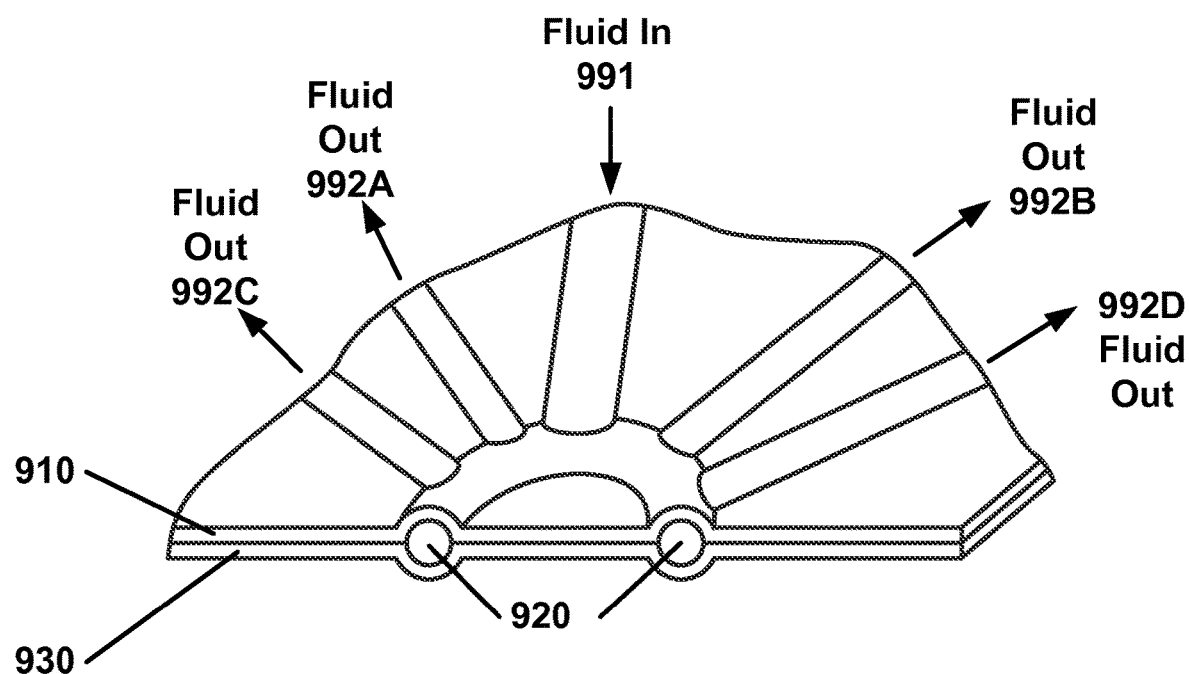

FIGS. 9A and 9B illustrate an example of a thermal element 900 according to an aspect of various embodiments. FIGS. 9A and 9B illustrate an alternative embodiment to FIGS. 8A and 8B. Thermal element 900 may comprise at least one tube 920. The at least one tube 920 may be employed to circulate at least one liquid, gel, air, and/or gas through at least a portion of a pillow. Thermal element 900 may comprise flexible and/or resilient properties. Thermal element 900 may comprise a relief section 940 configured to accommodate a shoulder of a user. Thermal element 900 may, for example, comprise a blow molded or twin sheet formed part comprising hollow conduits 920. Sheets 910 and 930 may be bonded together to form the thermal element 900. The hollow conduits may, for example, be arranged in at least one radial pattern configured to deliver at least one liquid, gel, air, and/or gas to the center of the radial pattern (e.g. 991) and extract the at least one liquid, gel, air, and/or gas from at least part of a perimeter of the radial pattern (e.g. 992A, 992B, 992C, 992D).

According to some of the various embodiments, a temperature of at least one liquid, gel, air, and/or gas may be increased or decreased through employment of a thermoelectric device. The thermoelectric device may be located in the pillow (e.g. as thermal element 140) or in a remote enclosure (e.g. 240, 340). The at least one metal wire, the at least one metal sheet, and/or the at least one metal rod may be configured as a heat sink. The heat sink may be connected to at least one additional thermal element. The at least one metal wire may, for example, be configured as a woven wire mesh. The woven wire mesh may comprise a highly thermally conductive material. The woven wire mesh may, for example, be woven into at least one material suspended from a support structure. Alternatively, the woven wire mesh may, for example, be a distinct layer from the at least one material suspended from a support structure. Distinct layers may be separated by at least one material. Furthermore, the woven wire mesh may, for example, be a distinct layer from the woven fiber mesh of a capacitive proximity sensor According to some of the various embodiments, the at least one thermal element 140 may, for example, comprise at least one external thermal element. The at least one external element may, for example, be at least partially located in a remote enclosure. The remote enclosure may comprise a heat exchange unit configured to increase or decrease a temperature of the at least one liquid, gel, air, and/or gas configured for delivery to the pillow 110.

According to some of the various embodiments, a temperature sensor or thermocouple may, for example, be employed to monitor the temperature of the at least one liquid, gel, air, and/or gas in the at least one thermal element 140. Alternatively, the remote enclosure may, for example, be configured to mix at least one additional liquid, gel, air, and/or gas to affect the temperature of the at least one liquid, gel, air, and/or gas present in the at least one thermal element 140. The thermal element 140 may couple to at least one valve and/or at least one pump. The at least one thermal element 140 may, for example, be activated to stay at a user specified temperature, within a user specified temperature range, and/or other defined temperature range. The activation of a thermal element may, for example, depend upon a period of time, multiple periods of time, the time of day, a combination thereof, and/or the like. The activation of a thermal element may, for example, comprise adjusting a flow rate of at least one liquid, gel, air, and/or gas.

According to some of the various embodiments, measurements may, for example, be taken over at least one period of time. The period of time may, for example, comprise a time between 30 and 120 minutes, a time related to at least one sleep cycle, a time between 3 and 9 hours, a time related to at least one sleeping session, a time over a plurality of days, a time related to a plurality of sleeping sessions, combinations thereof, and/or the like.

Some of the various embodiments may include at least one wearable device. The wearable device may, for example, include a temperature sensor 120. The wearable device may, for example, be configured to communicate temperature measurements to at least one of a processing unit 150, another apparatus, a remote device 170, a combination thereof, and/or the like. Wearable devices may, for example, be configured to measure sympathetic tone. At least one wearable device may, for example, be configured to communicate sympathetic tone measurements to at least one of: a processing unit 150, another apparatus, a remote device 170, a combination thereof, and/or the like. The wearable device may, for example, comprise at least one of the following: a display, a microprocessor, a memory, a user interface, a temperature sensor 120, a presence sensor 130, a heart rate sensor, a transceiver 160, computer instructions, a combination thereof, and/or the like. The heart rate sensor may, for example, be located remotely from the wearable device. The wearable device may, for example, be located on the user in at least one of the following locations: on at least one wrist, on at least one ankle, on a chest, on a head, on at least one finger, on at least one toe, on at least one fingertip, on at least one ear lobe, on at least one temple, on or around at least one hand, on at least one foot, on at least one arm, on at least one leg, a combination thereof, and/or the like. The wearable device may also, for example, be located on the user in at least one of the following locations: around at least one wrist, around at least one ankle, around a chest, around a head, around at least one finger, around at least one toe, around at least one fingertip, around at least one ear lobe, around at least one temple, around at least one hand, around at least one foot, around at least one arm, around at least one leg, a combination thereof, and/or the like. Alternatively, the wearable device may, for example, be embedded in an article of clothing.

According to some of the various embodiments, an apparatus may comprise a thermostat. An apparatus may, for example, comprise at least one fan to circulate air and/or at least one gas, a compressor to circulate and/or pressurize air and/or at least one gas, at least one pump to circulate at least one liquid, gel, air, and/or gas, a combination thereof, and/or the like.

Figure 10:
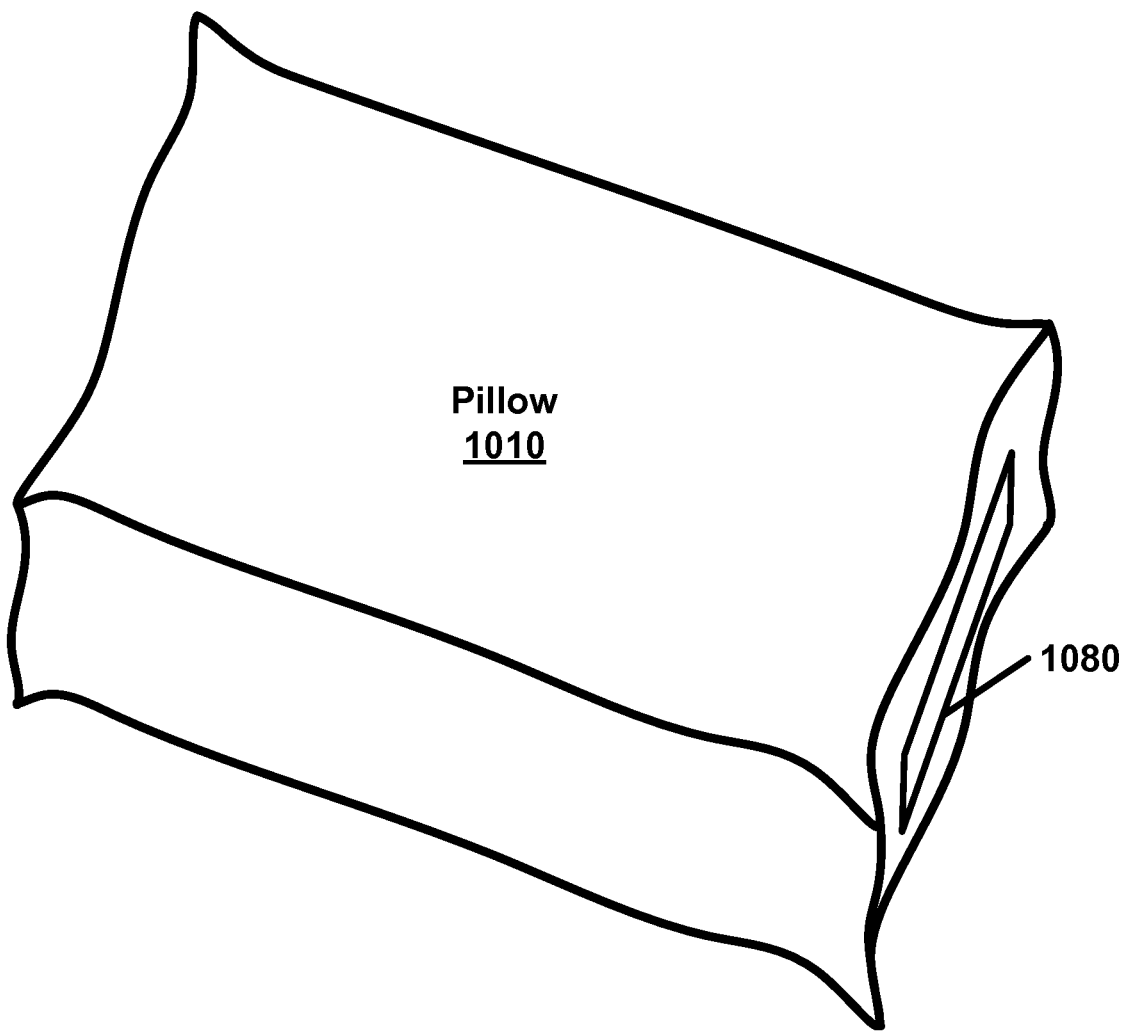
FIG. 10 is an illustration of an example electronically controllable pillow with a display as per an aspect of various embodiments.

FIG. 10 shows an aspect of an embodiment comprising a pillow 1010 and a display/input device 1080. The display/input device 1080 may be employed to allow a user of pillow 1010 to interact with the control functions of pillow 1010. Display 1080 may comprise an output device for presentation of information in visual or tactile form. When the input information is supplied as an electrical signal, the display may be referred to as an electronic display. The display 1080 may be configured to receive and/or display at least a portion of a display message. The display 1080 may be configured to receive and/or display at least a portion of a report message. The display may, for example, be configured to present information to a user. The information may, for example, associate presence measurements or the lack of presence measurements with a time of day, an interruption event, a sleep cycle phase, a sleep cycle number, a sleeping session, a sleep quality, a recommendation, a combination thereof, and/or the like.

Some of the various embodiments may include at least one user interface. A user interface may comprise components and/or systems employed to effectuate human and machine interactions. The interaction communicates operation and control desires of a user, and/or feedback from a machine. The user interface may comprise a graphical user interface, at least one switch, at least one indicator, at least one display (e.g. 1080), at least one touch screen, at least one projector, a combination thereof, and/or the like. The user interface may, for example, be configured via an external device or a remote device. The user interface may also, for example, be configured to receive at least one of the following: profile information associated with at least one user, preference information associated with at least one user, a combination thereof, and/or the like. Information sent to and/or from the display and/or user interface may be encrypted. Furthermore, additional spurious information may be sent to and/or from the display and/or user interface to hinder side channel attacks. The dummy information may be configured for transmission on a schedule that is consistent, random, based at least in part on information sent to or from the display, based at least in part on information sent to and/or from the user interface, based at least in part on information transmitted and/or received by the at least one transceivers, combinations thereof, and/or the like.

Some of the various embodiments may include at least one noise source. The at least one noise source may comprise at least one speaker, noise cancellation circuitry, at least one sound attenuation layer, a combination thereof, and/or the like. The noise source may generate background noise such as, for example, white noise, sounds from nature (e.g. waves, wind, rain, a beach, a forest, a waterfall, etc.), music, tones (e.g. biofeedback tones, binaural tones, tonal frequencies, etc.) combinations thereof, and/or the like. The noise source may be configured to accept noise source messages. The noise source may be configured to respond to at least one user input, at least one user setting, at least one user supplied audio file, combinations thereof, and/or the like.

According to some of the various embodiments, external thermal elements and associated equipment such as at least one fan, compressor, pump, power source, and/or thermostat, for example, may be associated with at least one sound reducing container. The sound reducing container may, for example, comprise at least one of the following sound reducing materials: at least one sound reducing mat, at least one sound reducing panel, sound reducing insulation, at least one liquid configured to attenuate sound, a combination thereof, and/or the like. Associated equipment such as the at least one fan, compressor, pump, and/or power source, for example, may be located remotely from other elements of the apparatus. Remote locations may, for example, comprise one or more separate containers, installations enclosed in one or more walls, centrally located equipment supporting a plurality of pillows, centrally located equipment supporting a plurality of rooms, a combination thereof, and/or the like. The remote location may comprise at least one sound reducing container. For example, a remote location may comprise at least one remote enclosure.

Some of the various embodiments may include a pillow height adjuster (e.g. 180, 280, 380). The pillow height adjuster (e.g. 180, 280, 380) may, for example, be electronically controllable. The pillow height adjuster (e.g. 180, 280, 380) may, for example, comprise at least one of the following: at least one hinged lever, an accordion support structure, at least one spring, at least one retractable column, an expandable bladder, a combination thereof, and/or the like. By way of example and not limitation, the accordion support structure may comprise a multi-hinged support structure, a folded wood fiber support structure, an inflatable lift bag, a combination thereof, and/or the like. A folded wood fiber support structure may, for example, comprise wood fibers, paper fibers, cardboard fibers, a combination thereof, and/or the like. The pillow height adjuster (e.g. 180, 280, 380) may, for example, further comprise at least one rod. According to some of the various embodiments, the rod may, for example, comprise at least one of the following materials: plastic, acrylic, wood, a combination thereof, and/or the like. The pillow height adjuster (e.g. 180, 280, 380) may, for example, be activated to stay at a user specified height, within a user specified height range, at a determined height, within a determined height range, combinations thereof, and/or the like. The activation of the pillow height adjuster (e.g. 180, 280, 380) may, for example, depend upon a period of time, multiple periods of time, the time of day, at least one sleeping session, at least one interruption event, at least one sleep cycle phase, at least one sleep cycle number, combinations thereof, and/or the like. The pillow (e.g. 110, 210, 310) may, for example, further comprise a foundation configured to reduce or eliminate expansion of the pillow into a bed or other compressible sleeping surface. Alternatively, the pillow (e.g. 210, 310) may, for example, further comprise a foundation in a separate container to be located under the pillow (e.g. 210, 310). The separate container may comprise at least one pillow height adjuster.

According to some of the various embodiments, the pillow height adjuster (e.g. 180, 280, 380) may comprise at least one of the following spring types: flat spring, tension spring, constant-force spring, gas spring, cantilever spring, a combination thereof, and/or the like. The at least one spring may, for example, comprise at least one of the following non-permeable materials: plastic, acrylic, rubber, wood, silicon, a chamber filled with at least one compressible gas (e.g. air), a chamber filled with at least one liquid, a chamber filled with at least one gel, a chamber configured to accept at least one compressible gas, a chamber configured to accept at least one liquid, a chamber configured to accept at least one gel, combinations thereof, and/or the like. The chamber may be collapsible. The chamber may, for example, comprise bellows. According to some of the various embodiments, the at least one chamber may be activated by at least one of the following: heat, electrical current, an additional gas, an additional liquid, an additional gel, a combination thereof, and/or the like. The at least one chamber may, for example, comprise at least part of at least one thermal element.

Figure 11A:
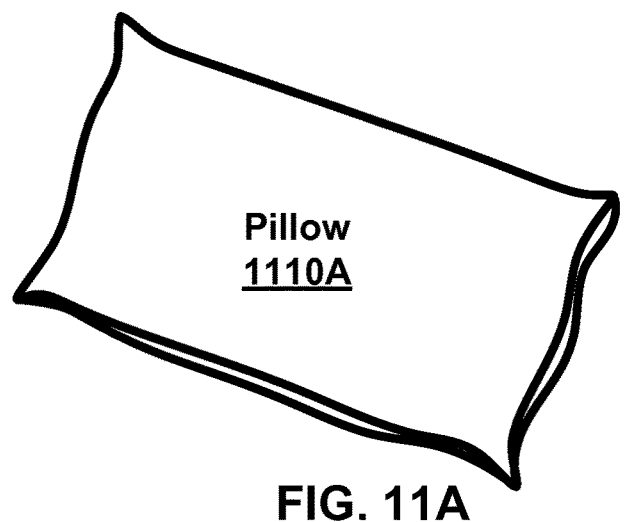
FIGS. 11A through 11C are illustrations of an example of an electronically controllable pillow adjusted to different heights as per aspects of various embodiments.
Figure 11B:
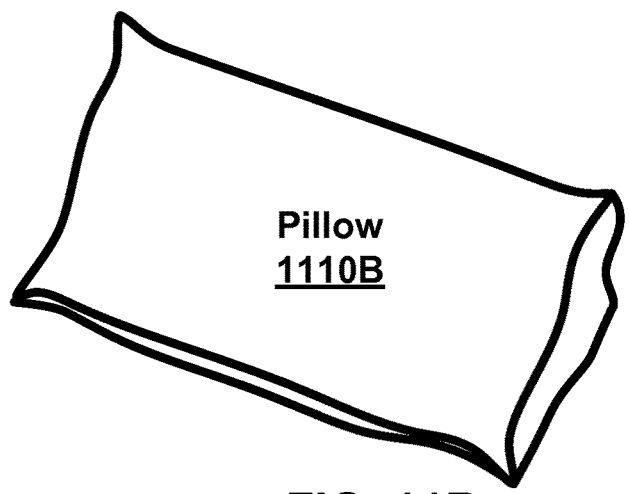
Figure 11C:
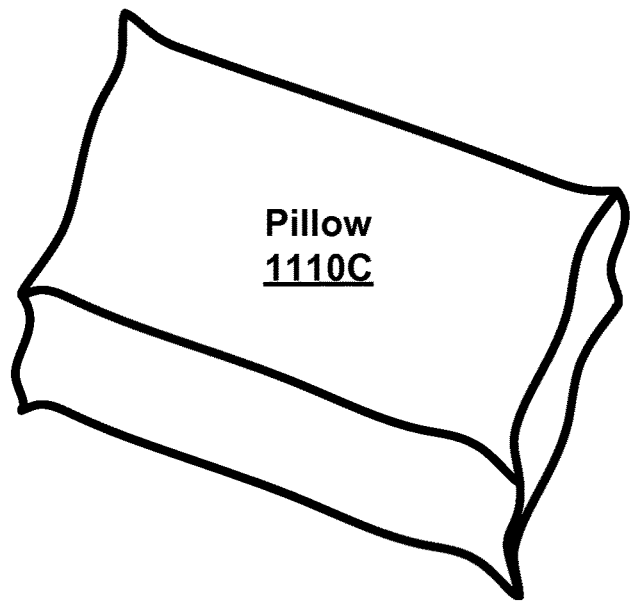

FIGS. 11A through 11C illustrate an example of an electronically controllable pillow adjusted to different heights as per aspects of various embodiments. According to some of the various embodiments, height adjuster(s) 180 may be employed, via processing unit 150, to adjust the height of the pillow. For example, a minimum height for height adjuster(s) 180 may correspond to a pillow with minimum thickness 1010A. A maximum height for height adjuster(s) 180 may correspond to a pillow with maximum thickness 1010C. An intermediate height for height adjuster (s) 180 may correspond to a pillow with an intermediate thickness 1010B.

Figure 12:
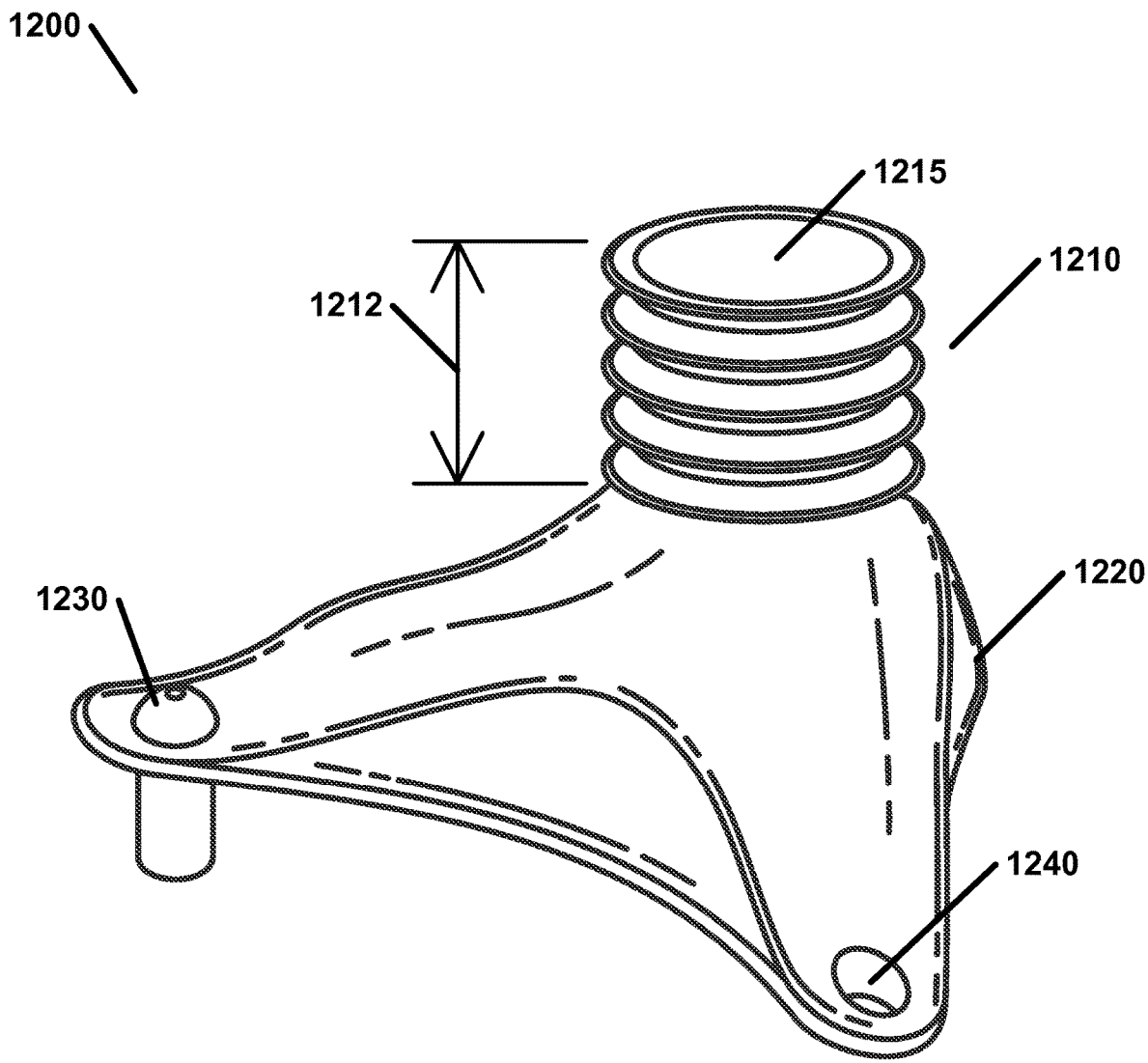
FIG. 12 is an illustration of an example of a pillow height adjuster according to an aspect of various embodiments.

FIG. 12 illustrates an example of a pillow height adjuster 1200 according to an aspect of various embodiments. The pillow height adjuster 1200 may comprise at least one chamber 1210 collectively comprising, for example, bellows. The at least one chamber 1210 may be configured to operate within a height range 1212. The at least one chamber 1210 may be supported by a hollow formed support 1220. The hollow formed support 1220 may be molded. The hollow formed support 1220 may be configured with at least one male plug 1230 and/or at least one female socket 1240. The at least one male plug 1230 and/or at least one female socket 1240 may be configured to link a plurality of hollow formed supports together. The top 1215 of the at least one chamber 1210 may be configured to support at least one support structure (e.g. 510).

Figure 13:
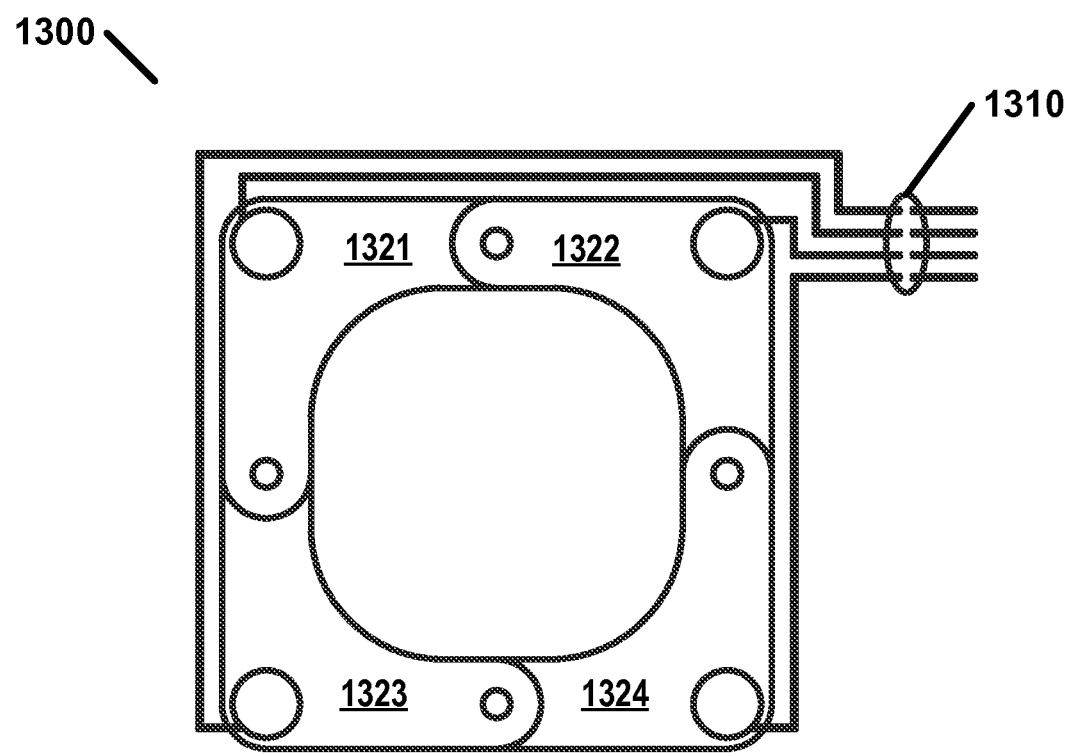
FIG. 13 is an illustration of an example of a plurality of pillow height adjusters according to an aspect of various embodiments.

FIG. 13 illustrates an example of a plurality of pillow height adjusters 1300 according to an aspect of various embodiments. Each of the plurality of pillow height adjusters 1300 may comprise a hollow formed support 1220. The plurality of hollow formed supports (1321, 1322, 1323, 1324) may be configured to link together to form a base structure. Each of the plurality of hollow formed supports (1321, 1322, 1323, 1324) may comprise at least one chamber 1210. The base structure may be configured to reduce or eliminate movement outside of a plurality of chambers. The plurality of chambers in the base structure may enable independent height adjustment on the left and right sides of a pillow, on the top edge and bottom edge of a pillow, on each corner of a pillow, a combination thereof, and/or the like. At least some of the plurality of chambers may, for example, be coupled to at least one tube 1310 configured to transport liquid(s), gel(s), air, and/or gas(es) to or from the at least some of the plurality of chambers. The liquid(s), gel(s), air, and/or gas(es) may be employed to raise or lower at least one of the plurality of chambers through vertical expansion or contraction within at least one vertical adjustment range. The plurality of chambers may be coupled to a support structure comprising, for example, the rigid structural tube element (e.g. 510).

Figure 14A:
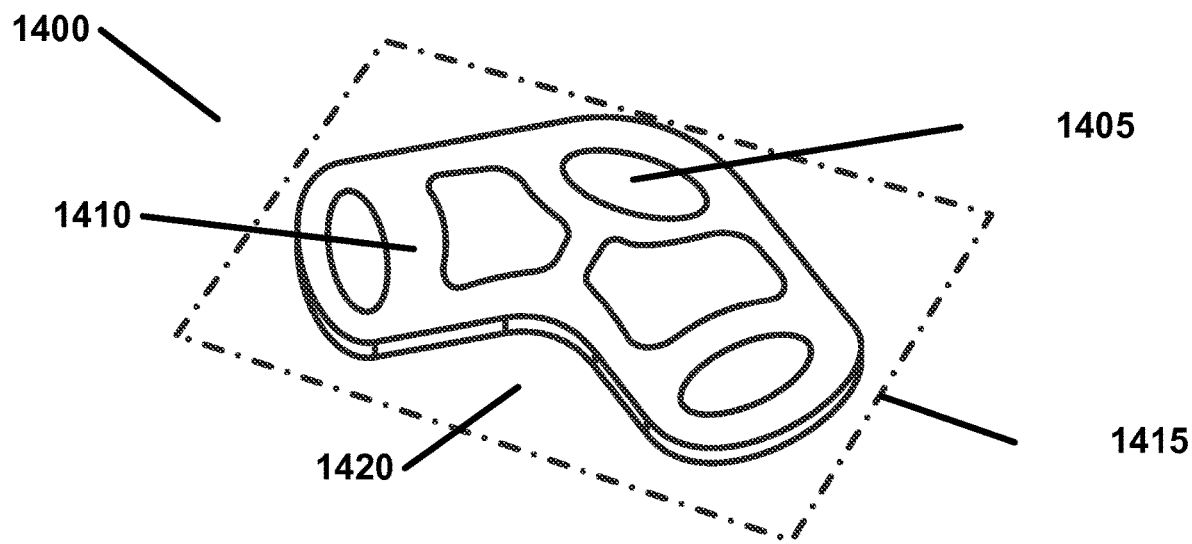
FIGS. 14A-14C are illustrations of an example pillow height adjuster according to an aspect of various embodiments.
Figure 14B:
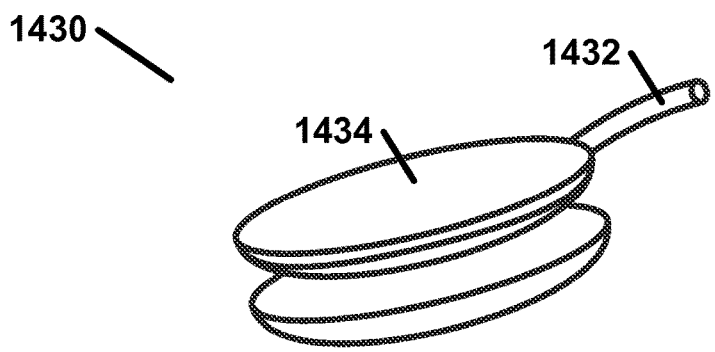
Figure 14C:
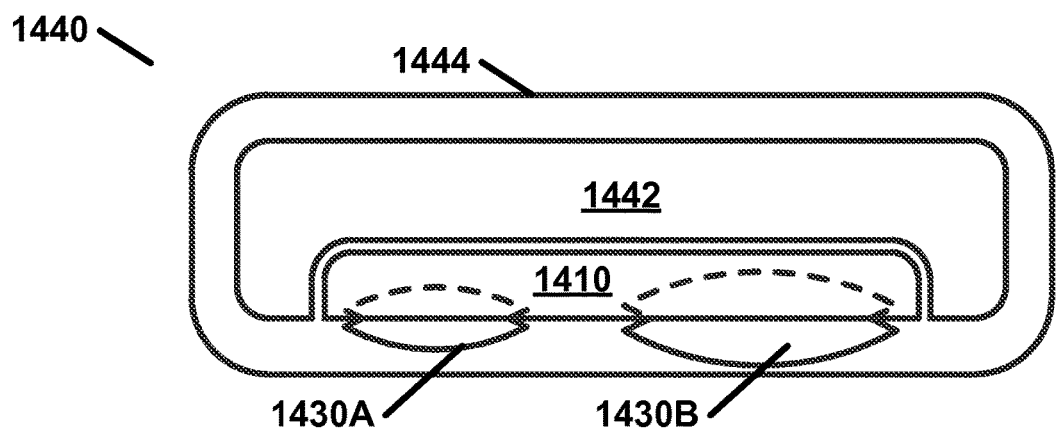

FIGS. 14A-14C collectively illustrate an example of a pillow height adjuster 1400 according to an aspect of various embodiments. The pillow height adjuster 1400 may comprise at least one support frame 1410. The at least one support frame 1410 may be rigid and/or semi-rigid. The at least one support frame 1410 may be configured to connect to the top surface 1434 of at least one expandable lift bag (1430A, 1430B) through at least one relief pocket 1405. Each of the at least one expandable lift bag (1430A, 1430B) may comprise a plurality of adjacent chambers. For example, a first chamber of the plurality of adjacent chambers may be filled with liquid(s), gel(s), air, and/or gas(es) configured to expand with heat. A second chamber of the plurality of adjacent chambers may be coupled to at least one tube 1432 configured to transport liquid(s), gel(s), air, and/or gas(es) to or from the second chamber. According to some of the various embodiments, the at least one support frame 1410 may be configured to reduce or eliminate movement outside of the at least one expandable lift bag 1430. The pillow height adjuster 1400 may comprise at least one foundation 1415 configured to minimize expansion pillow 1440 below the bottom surface of the pillow. The at least one support frame 1410 may have at least one relief area 1420 configured to accommodate a shoulder of a user. A plurality of expandable lift bags (e.g. 1430A, 1430B) may enable independent height adjustment on the left and right sides of a pillow and/or on the top edge and bottom edge of a pillow. At least some of the plurality of chambers residing inside the at least one expandable lift bag 1430 may, for example, be coupled to at least one tube 1432 configured to comprise pressurized liquid(s), gel(s), air, and/or gas(es). The liquid(s), gel(s), air, and/or gas(es) may be pressurized to raise or lower at least one of the plurality of chambers through vertical expansion or contraction within at least one vertical adjustment range. Pillow 1440 may further comprise at least one first material 1442 configured to cushion the pillow height adjuster 1400 from a user of a pillow 1440. The pillow 1440 may further comprise at least one second material 1444 to enclose the at least one first material 1442.

Figure 15A:
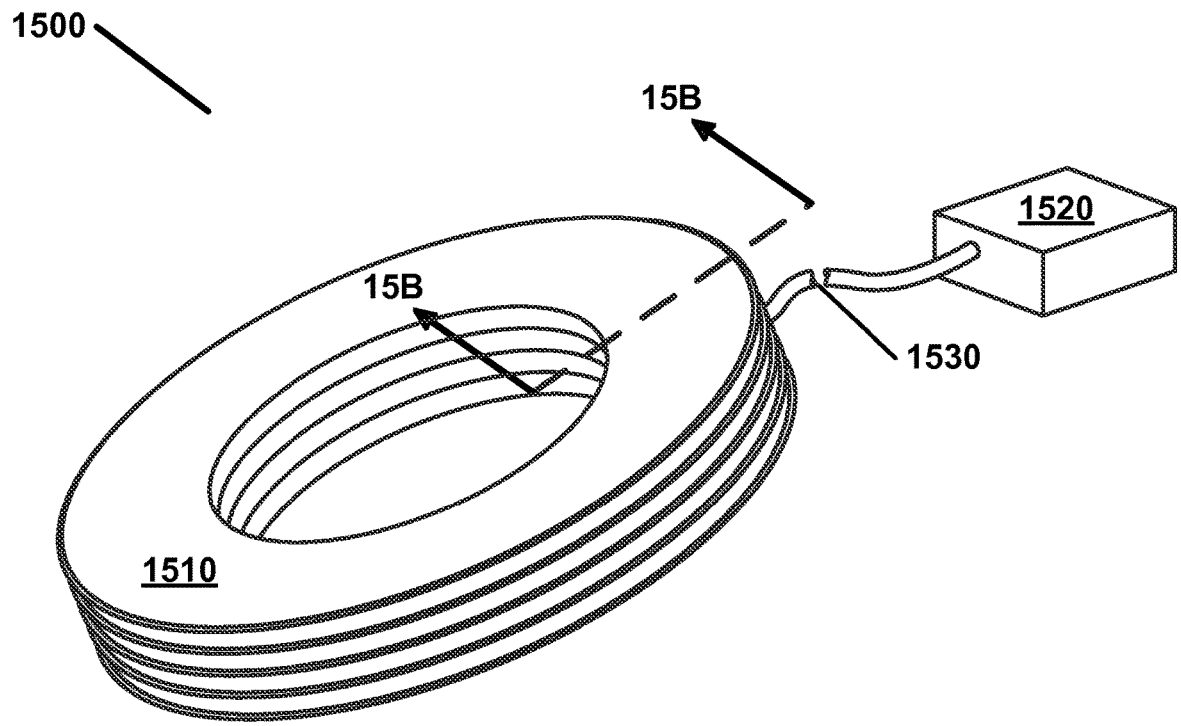
FIGS. 15A and 15B are illustrations of an example pillow height adjuster according to an aspect of various embodiments.
Figure 15B:
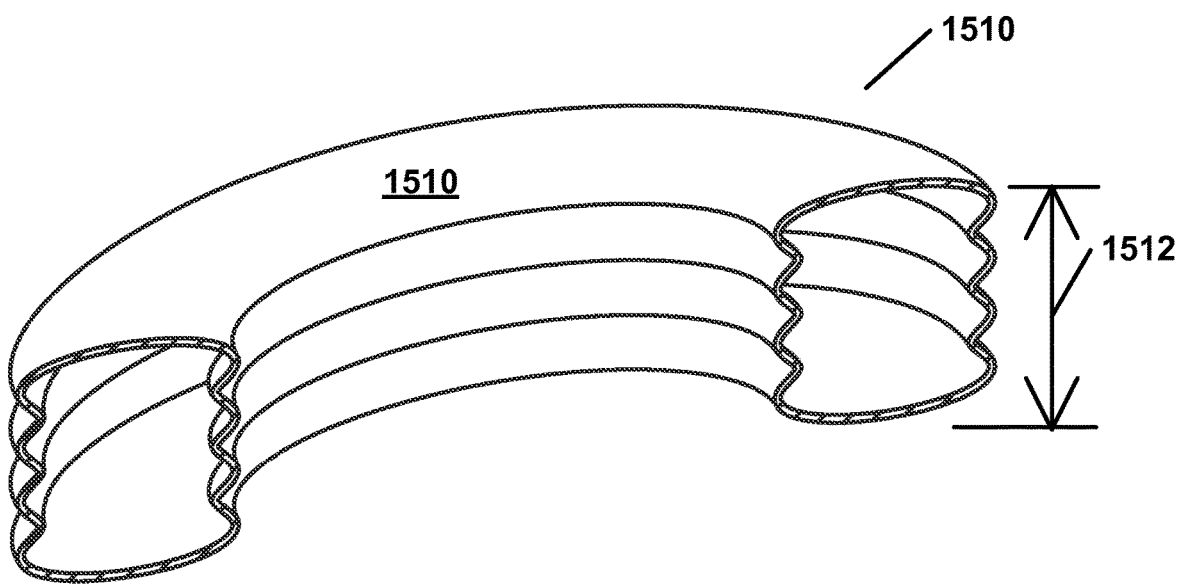

FIGS. 15A and 15B illustrate an example of a pillow height adjuster 1500 according to an aspect of various embodiments. The pillow height adjuster 1500 may comprise at least one chamber collectively comprising bellows 1510. The bellows 1510 may collectively comprise the shape of an oval ring. The at least one chamber may enable uniform height adjustment through a predetermined adjustment range 1512 across at least a portion of a top surface of a pillow. Alternatively, a plurality of chambers, each of at least some of the plurality of chambers independently coupled to at least one tube 1530, may enable independent height adjustment on the left and right sides of a pillow and/or on the top edge and bottom edge of a pillow. The at least one chamber may enable uniform height adjustment across the pillow. At least one of the at least one chamber may be coupled to at least one tube 1530 configured to comprise pressurized liquid(s), gel(s), air, and/or gas(es) from remote enclosure 1520. The liquid(s), gel(s), air, and/or gas(es) may be pressurized to raise or lower the at least one of the at least one chamber through vertical expansion or contraction within at least one vertical adjustment range 1512.

Figure 16:
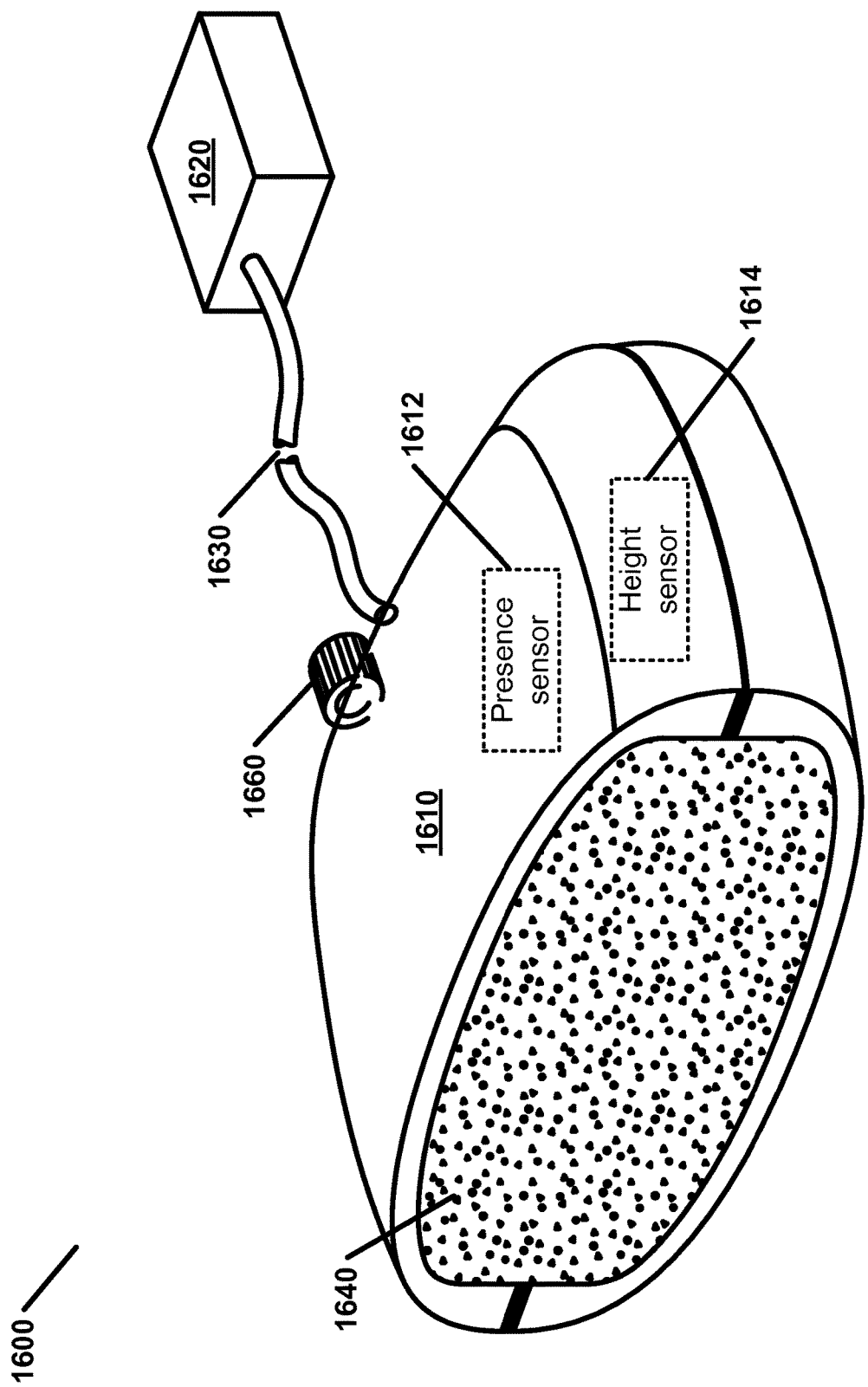
FIG. 16 is an illustration of an example pillow comprising a pillow height adjuster according to an aspect of various embodiments.

FIG. 16 illustrates an example of a pillow comprising a pillow height adjuster according to an aspect of various embodiments. The electronically controllable pillow 1600 may comprise a pillow 1610 filled with at least one material 1640. The at least one material 1640 may be configured to expand a height of pillow 1640 with additional air volume inside the pillow. Air volume may be manually added or reduced through manual air valve 1660. Air volume may be automatically added or removed via a remote enclosure 1620 when the manual air valve 1660 is closed. Remote enclosure 1620 may be coupled to pillow 1610 through at least one tube 1630 configured to transport air and/or other gas. At least one presence sensor 1612 may be employed in the automatic operation of at least one height adjuster disposed in remote enclosure 1620. The at least one presence sensor 1612 may be disposed in the pillow 1610 and/or in the remote enclosure 1620. At least one pillow height sensor 1614 may be employed in the automatic operation of at least one height adjuster disposed in remote enclosure 1620. The at least one pillow height sensor 1614 may be disposed in the pillow 1610 and/or in the remote enclosure 1620.

Figure 17:
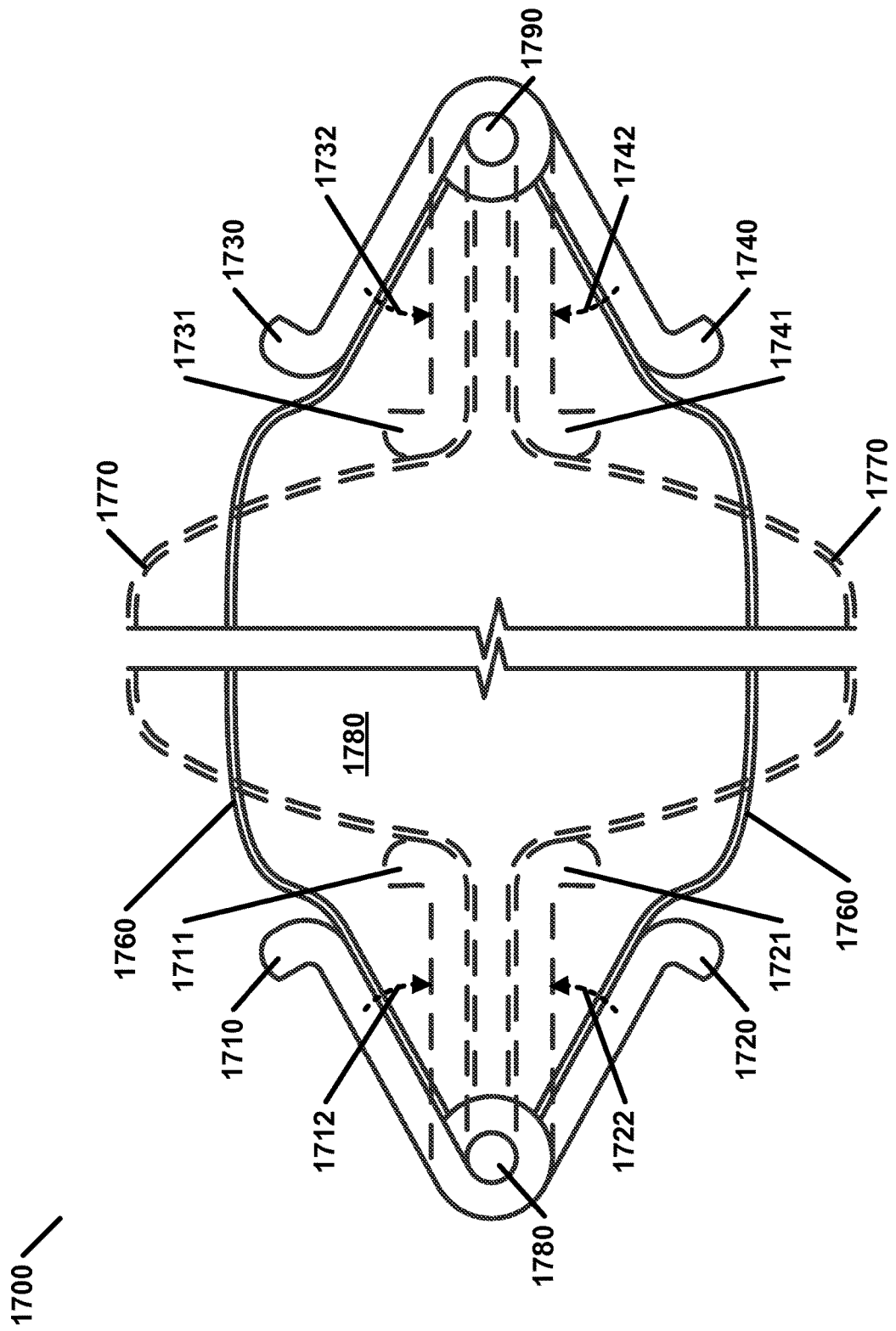
FIG. 17 is an illustration of an example pillow height adjuster according to an aspect of various embodiments.

FIG. 17 illustrates an example of a pillow height adjuster 1700 according to an aspect of various embodiments. Pillow height adjuster 1700 may comprise at least one constant volume sealed chamber 1780 at a minimum height 1760. The at least one constant volume sealed chamber 1780 may be filled with at least one non-compressible liquid or gel. At least one squeeze mechanism may comprise at least one squeeze lever at a minimum position (1710, 1720, 1730, 1740) that enables the minimum height 1760. Two of the at least one squeeze lever may be joined by at least one hinge (1780, 1790). The at least one squeeze mechanism may be activated by at least one servo. The at least one servo may be collectively powered by at least one power source. Alternatively, at least one of a plurality of servos may be powered by at least one independent power source. The at least one squeeze mechanism may be activated through a range of travel (1712, 1722, 1732, 1742). The at least one squeeze mechanism may comprise at least one squeeze lever at a maximum position (1711, 1721, 1731, 1741) that enables the maximum height 1770. Pillow height adjuster 1700 may be activated by a plurality of squeeze mechanisms and a plurality of servos. Additional squeeze mechanisms may enable a smaller footprint for each of the plurality of squeeze mechanisms. Additional servos may enable a smaller power requirement for each of the plurality of servos. Each of the plurality of servos may comprise a battery operated DC gear motor. The battery operated DC gear motor may be coupled to a gear reduction assembly.

The at least one constant volume sealed chamber 1780 may be coupled to a pressure sensor configured to provide user presence of the pillow.

Figure 18:
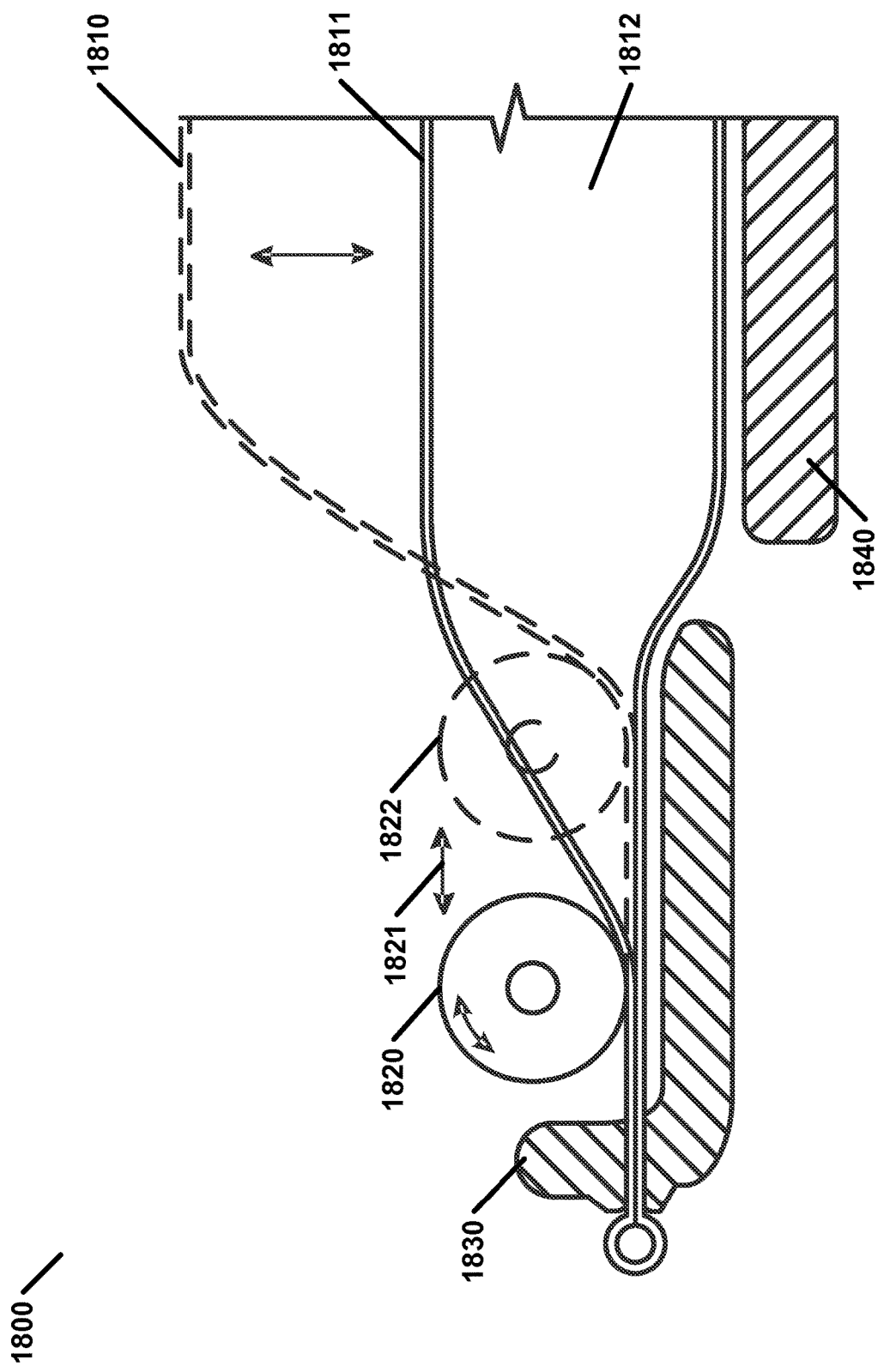
FIG. 18 is an illustration of an example pillow height adjuster according to an aspect of various embodiments.

FIG. 18 illustrates an example of a pillow height adjuster 1800 according to an aspect of various embodiments. Pillow height adjuster 1800 may comprise at least one constant volume sealed chamber 1812. The at least one constant volume sealed chamber 1812 may be secured by at least one secure mechanism 1830. The at least one secure mechanism 1830 may be further configured to support at least one squeeze mechanism. Pillow height adjuster 1800 may comprise a foundation 1840. The foundation 1840 may be independent from secure mechanism 1830. Alternatively, the at least one secure mechanism 1830 may be integrated with foundation 1840. The at least one constant volume sealed chamber 1812 may be filled with at least one non-compressible liquid or gel. The least one squeeze mechanism may comprise at least one squeeze roller at a minimum position 1820 that enables a minimum height 1811. The at least one squeeze roller may be activated by at least one servo. The at least one servo may be collectively powered by at least one power source. Alternatively, at least one of a plurality of servos may be powered by at least one independent power source. The at least one squeeze mechanism may be activated through a range of travel 1821. The at least one squeeze mechanism may comprise at least one squeeze roller at a maximum position 1822 that enables the maximum height 1810. Pillow height adjuster 1800 may be activated by a plurality of squeeze mechanisms and a plurality of servos. Additional squeeze mechanisms may enable a smaller footprint for each of the plurality of squeeze mechanisms. Additional servos may enable a smaller power requirement for each of the plurality of servos.

Figure 19:
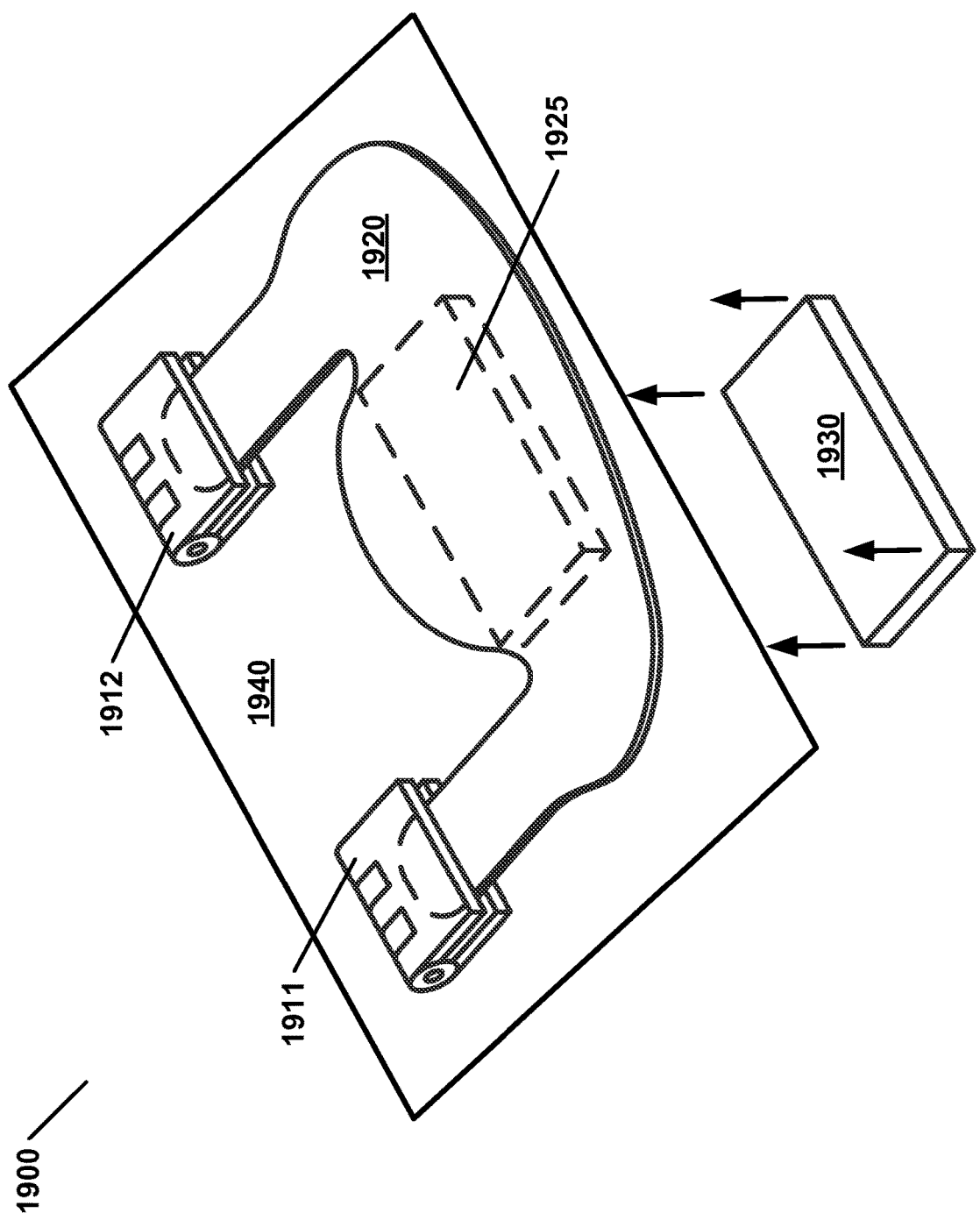
FIG. 19 is an illustration of an example pillow height adjuster according to an aspect of various embodiments.

FIG. 19 illustrates an example of a pillow height adjuster 1900 according to an aspect of various embodiments. Pillow height adjuster 1900 may comprise at least one constant volume sealed chamber 1920. Pillow height adjuster 1900 may comprise at least one foundation 1940. The at least one constant volume sealed chamber 1920 may be coupled to the at least one foundation 1940 through a plurality of squeeze mechanisms (1911, 1912). The at least one constant volume sealed chamber 1920 may be coupled to at least one thermo-electric device 1930. The at least one constant volume sealed chamber 1920 may be configured to accept at least one thermo-electric device 1930 in a location 1925, for example, configured to affect the height of the constant volume sealed chamber. The least one thermo-electric device 1930 may be disposed within the at least one constant volume sealed chamber 1920. The at least one constant volume sealed chamber 1920 may comprise a non-permeable membrane. Each of the at least one constant volume sealed chamber 1920 may be filled with at least one liquid, gel, or gas.

Some of the various embodiments may include at least one pillow height sensor (e.g. 185, 285, 385). A pillow height sensor (e.g. 185, 285, 385) may comprise a device configured to measure the height of a pillow height adjuster, a chamber comprising at least a part of a pillow height adjuster, at least a portion of a pillow (e.g. 110, 210, 310), combinations thereof, and/or the like. The pillow height sensor (e.g. 185, 285, 385) may, for example, be configured to communicate height measurements to processing unit (e.g. 150, 250, 350). According to some of the various embodiments, the pillow height sensor (e.g. 185, 285, 385) may comprise at least one encoder, at least one camera, at least one light transmitter, at least one photoelectric receiver, at least one pressure sensor, a combination thereof, and/or the like. By way of example and not limitation, the at least one encoder may comprise a linear encoder, a rotary encoder, a combination thereof, and/or the like. By way of example and not limitation, pillow height measurement communicated by a fixed camera may compare the current image with a reference image. A height difference may, for example, be determined by comparing images and counting the number of different pixels.

According to some of the various embodiments, height measurements may comprise differential height measurements, relative height measurements, absolute height measurements, a combination thereof, and/or the like. The pillow height sensor (e.g. 185, 285, 385) may, for example, communicate measurements according to a clock, at intervals required by a processing unit, at intervals required by a transceiver, at intervals specified by a remote device, at intervals specified by a second apparatus, at intervals selected by a user, a combination thereof, and/or the like. Some of the various embodiments may include a memory. The memory may, for example, be configured to store at least one of: settings for at least one user, temperature measurements, presence measurements, height measurements, a combination thereof, and/or the like.

Memory may include physical device(s) used to store programs (sequences of instructions) or data on a temporary or permanent basis for use by other elements such as processing unit 150, temperature sensor 120, presence sensor 130, thermal element 140, height adjuster 180, height sensor 185, transceiver 160, remote device 170, combinations thereof, and/or the like. Memory 3440 may comprise instruction segment(s) and/or data segment(s). Memory may include primary high speed memory (i.e. RAM, ROM, etc.), and/or secondary memory, which may include physical devices for program and data storage which are slow to access but offer higher memory capacity. The term storage may include devices such as, but not limited to: tape, magnetic disks and optical discs (CD-ROM and DVD-ROM). If needed, primary memory may be stored in secondary memory employing techniques such as "virtual memory."

Primary memory may be an addressable semiconductor memory, i.e. integrated circuits consisting of silicon-based transistors accessible to processing unit 150. Semiconductor memory may include volatile and/or non-volatile memory. Examples of non-volatile memory are flash memory (sometimes used as secondary, sometimes primary computer memory) and ROM/PROM/EPROM/EEPROM memory (used for firmware such as boot programs). Examples of volatile memory are primary memory (typically dynamic RAM, DRAM), and fast CPU cache memory (typically static RAM, SRAM, which is fast but energy-consuming and offer lower memory capacity per area unit than DRAM).

The instruction segment may include computer readable instructions configured to cause at least one processing unit 150 to, among other tasks: collect sensor data from at least one of the multitude of sensors 120, 130 and 185, combinations thereof, and/or the like and to control thermal element 140 height adjuster 180, transceiver 160, combinations thereof, and/or the like.

According to some of the various embodiments, an apparatus may include a controller. A controller may comprise a mechanism that controls or regulates, directly or indirectly, the operation of a machine and/or device. The controller may, for example, be configured to activate at least one thermal element 140. The controller may also, for example, be configured to receive temperature messages. According to some of the various embodiments, temperature messages may be received from the at least one processing unit 150, the at least one transceiver 160, the at least one remote device 170, a combination thereof, and/or the like. The temperature messages may, for example, be based at least in part on temperature measurements. The temperature messages may also, for example, be related to at least one user input. Furthermore, according to some of the various embodiments, the temperature messages may be related to at least one of the following: a desired number of hours of sleep, a desired wake time, a desired temperature, an elapsed time, a time of day, at least one identified sleep cycle phase, a recommended number of sleep cycle phases, a recommended wake time, a recommended temperature, a combination thereof, and/or the like. The temperature messages may also, for example, be related to at least one of the following: at least one sleeping session, at least one interruption event, at least one sleep cycle phase, at least one sleep cycle number, a combination thereof, and/or the like. The temperature messages and the data relied upon may, for example, be configured to minimize restlessness for a user, minimize restlessness for a user over at least one sleep cycle phase, minimize restlessness for a user over at least one sleeping session, a combination thereof, and/or the like. A temperature message may, for example, comprise a message header, a message body, at least one acknowledgement bit, at least one error correction bit, a combination thereof, and/or the like. A temperature message may, for example, comprise a SMS message, an email message, at least one digital packet configured for transmission, a combination thereof, and/or the like. A temperature message may, for example, comprise at least one digital bit, at least one digital byte, a digital bit stream, a combination thereof, and/or the like. Alternatively, a temperature message may, for example, comprise an analog voltage, a direct current, an alternating current, a combination thereof, and/or the like.

A thermal element circuit may, for example, be associated with an apparatus. By way of example and not limitation, the thermal element circuit may comprise a controller electrically coupled to at least one thermal element. Alternatively, the thermal element circuit may, for example, comprise a processing unit electrically coupled to at least one thermal element. According to some of the various embodiments, the apparatus may comprise at least one pillow.

As disclosed earlier, the apparatus may include a controller. According to some of the various embodiments, the controller may, for example, be configured to activate a pillow height adjuster 180. The controller may also, for example, be configured to receive height messages. According to some of the various embodiments, height messages may be received from the at least one processing unit 150, the transceiver 160, the remote device 170, a combination thereof, and/or the like. The height messages may, for example, be based at least in part on height measurements. The height messages may also, for example, be related to at least one user input. Furthermore, according to some of the various embodiments, the height messages may be related to at least one of the following: a desired number of hours of sleep, a desired wake time, a desired height, an elapsed time, a time of day, at least one identified sleep cycle phase, a recommended number of sleep cycle phases, a recommended wake time, a recommended height, a combination thereof, and/or the like. The height messages may also, for example, be related to at least one of the following: at least one sleeping session, at least one interruption event, at least one sleep cycle phase, at least one sleep cycle number, a combination thereof, and/or the like. The height messages and the data relied upon may, for example, be configured to minimize restlessness for a user, minimize restlessness for a user over at least one sleep cycle phase, minimize restlessness for a user over at least one sleeping session, a combination thereof, and/or the like.

Users may desire different heights at different times. For example, when a person lies on their back, they may desire one height, a person lying prone may desire a second height, and a person lying on their side may desire a third height. Additionally, there may be therapeutic reasons for a person to have their pillow adjusted to different heights at different times. For example, if a person's breathing rate is increasing due to detected shoulder blade movement, it may be advantageous for the height of the pillow to be adjusted.

According to some of the various embodiments, the at least one thermal element and/or at least one pillow height adjuster may be at least partially disposed in a remote enclosure.

Figure 20:
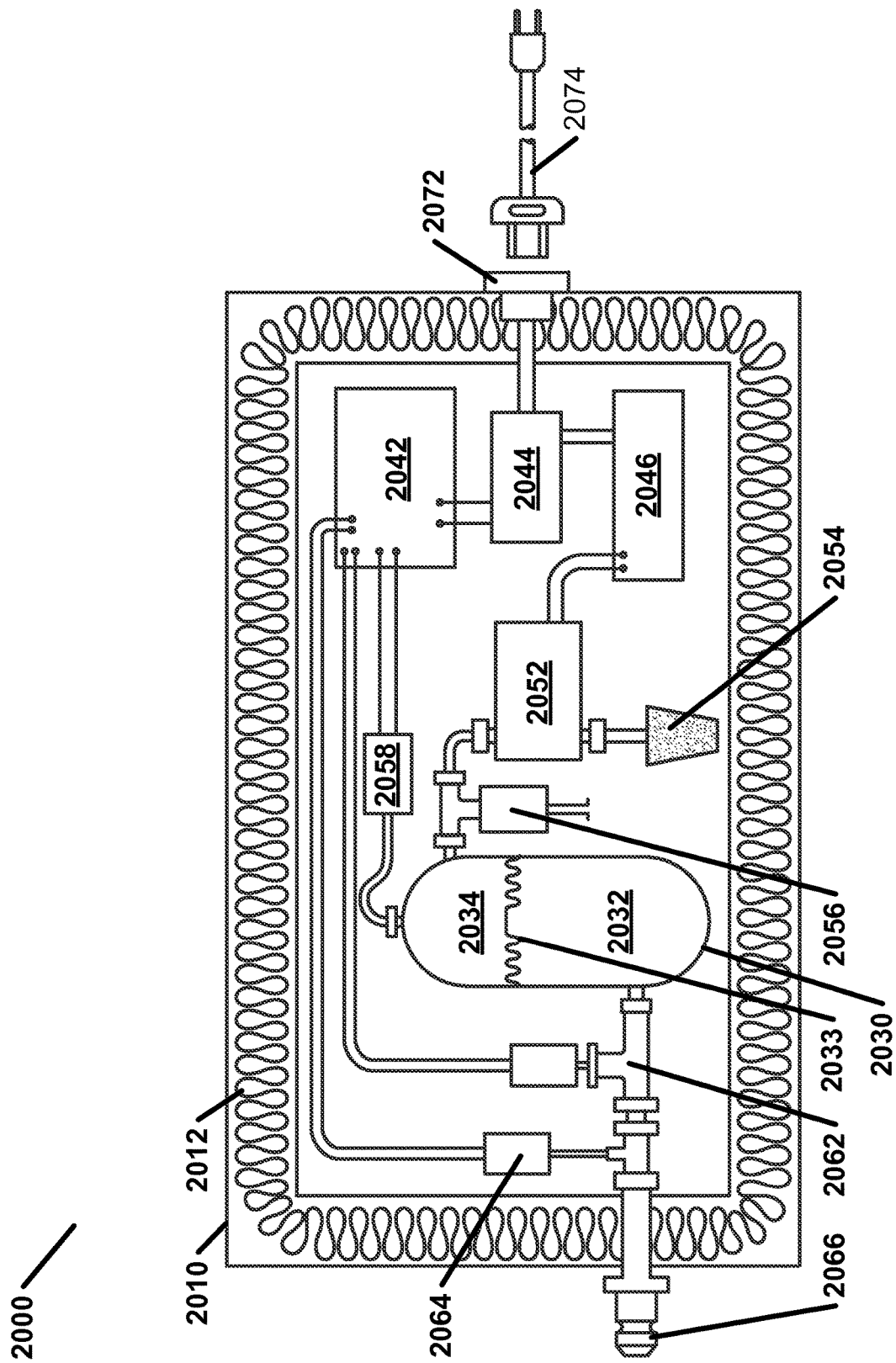
FIG. 20 is an illustration of an example remote enclosure according to an aspect of various embodiments.

FIG. 20 illustrates an example of a remote enclosure according to an aspect of various embodiments. The remote enclosure 2000 may comprise at least one sound reducing container 2010. The at least one sound reducing container may comprise at least one sound reducing material 2012. The at least one remote enclosure 2000 may comprise at least one pump (or compressor) 2052. The at least one pump 2052 may comprise at least one pump motor and at least one filtered air inlet 2054. The at least one remote enclosure 2000 may comprise at least one power source 2044. The at least one power source 2044 may comprise at least one power supply, at least one power converter, at least one fuse, at least one battery, at least one rechargeable battery, combinations thereof, and/or the like. The at least one power source 2044 may be coupled to at least one power and/or charging port 2072. The at least one power and/or charging port 2072 may be configured to accept at least one power cable 2074. The remote enclosure 2000 may comprise at least one high voltage distribution and relay device 2046. The at least one pump 2052 may be electrically coupled to the at least one high voltage distribution and relay device 2046. The remote enclosure 2000 may comprise at least one low voltage control processor and distribution device 2042. The remote enclosure 2000 may comprise at least one accumulator 2030. The at least one accumulator 2030 may comprise a working fluid section 2032 and an air section 2034. The working fluid section 2032 and the air section 2034 may be separated by a diaphragm 2033. The at least one accumulator 2030 may be coupled to the at least one pump 2052 through at least one bleed valve 2056. The at least one bleed valve 2056 may be servo controllable. The at least one bleed valve 2056 may be electrically coupled to the at least one low voltage control processor and distribution device 2042. The at least one accumulator 2062 may be coupled to at least one flow control valve 2062. The at least one flow control valve 2062 may be servo controllable. The at least one flow control valve 2062 may be electrically coupled to the at least one low voltage control processor and distribution device 2042. The at least one flow control valve 2062 may be coupled to at least one pillow side pressure sensor 2064. The at least one pillow side pressure sensor 2064 may be electrically coupled to the at least one low voltage control processor and distribution device 2042. The at least one pillow side pressure sensor 2064 may be coupled to at least one quick disconnect fitting 2066. The at least one quick disconnect fitting 2066 may be configured to accept at least one tube from the pillow (e.g. 210, 310). The air section 2034 of the at least one accumulator 2030 may be coupled to a supply side pressure sensor 2058. The supply side pressure sensor 2058 may be electrically coupled to the at least one low voltage control processor and distribution device 2042.

Figure 21:
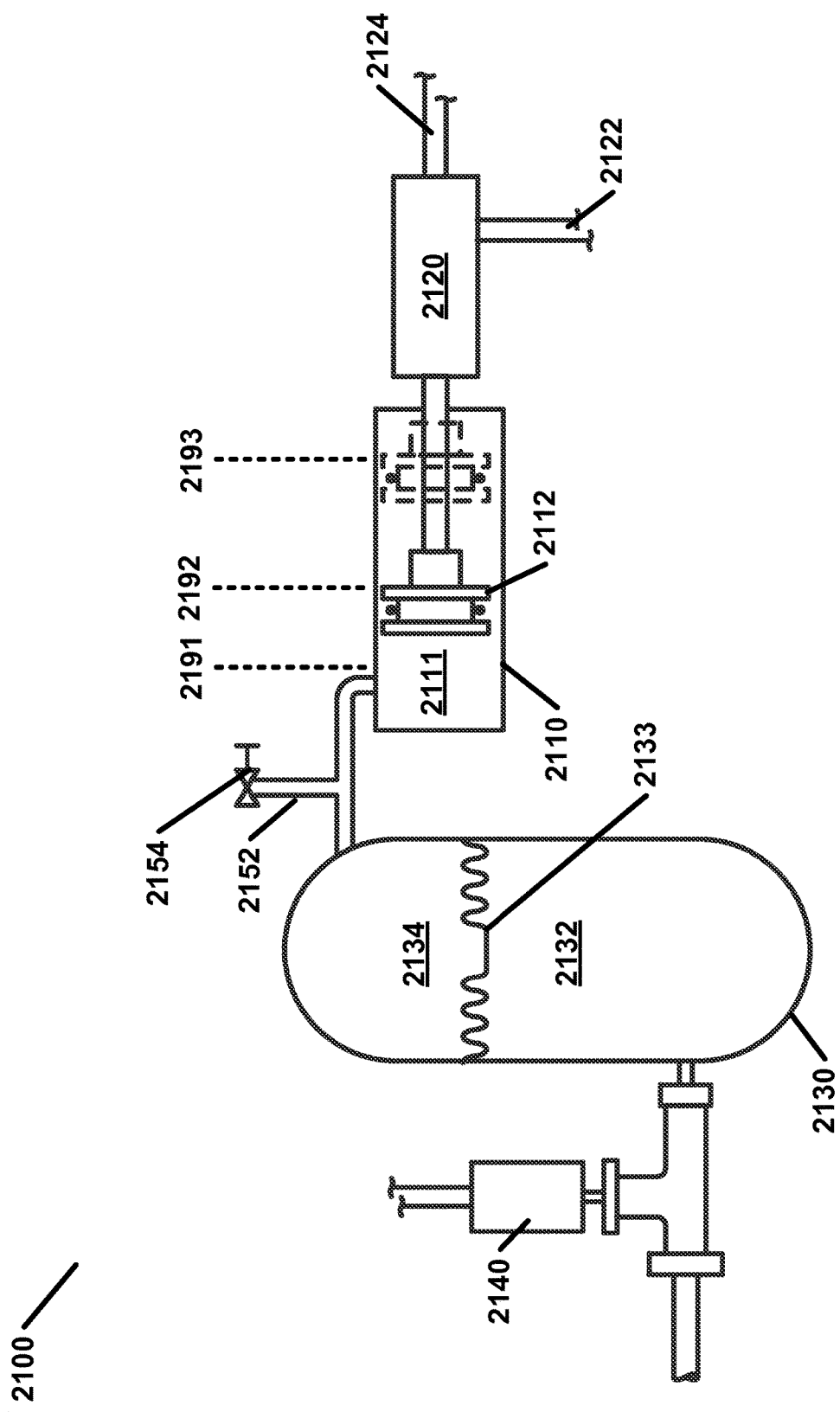
FIG. 21 is an illustration of an example pillow height adjuster disposed in a remote enclosure according to an aspect of various embodiments.

FIG. 21 illustrates an example of pillow height adjuster 2100 disposed in a remote enclosure according to an aspect of various embodiments. The pillow height adjuster 2100 may comprise a cylinder 2110. The cylinder 2110 may comprise a piston 2112. The piston 2112 may be mechanically coupled to a linear actuator 2120. The linear actuator 2120 may be electrically coupled to at least one high voltage distribution and relay device (e.g. 2046) via power cables 2122. The linear actuator 2120 may be electrically coupled to at least one low voltage control processor and distribution device (e.g. 2042) via control cables 2124. The linear actuator 2120 may be configured to actuate the piston 2112 in a range within the cylinder 2110. The range may comprise a maximum position 2191 corresponding to maximum pressure and therefore a maximum height of at least one pillow height adjuster. The range may further comprise a minimum position 2193 corresponding to minimum pressure and therefore a minimum height of at least one pillow height adjuster. The range may further comprise an intermediate position 2192 corresponding to an intermediate pressure and therefore an intermediate height of at least one pillow height adjuster 2100. The at least one cylinder 2110 may comprise a cylinder air section 2111. The at least one cylinder 2110 may be coupled to at least one accumulator 2130. The at least one accumulator 2130 may comprise a working fluid section 2132 and an air section 2134. The working fluid section 2132 and the air section 2134 may be separated by a diaphragm 2133. The at least one accumulator 2130 may be coupled to the at least one cylinder 2110 via at least one air pressure inlet 2152. The air pressure inlet 2152 may be operated by a shut off valve 2154. The shut off valve 2154 may be configured for manual operation and/or servo controllable. The at least one accumulator 2130 may be coupled to at least one flow control valve 2140. The at least one flow control valve 2140 may be servo controllable. The at least one flow control valve 2140 may be electrically coupled to the at least one low voltage control processor and distribution device (e.g. 2042).

Figure 22:
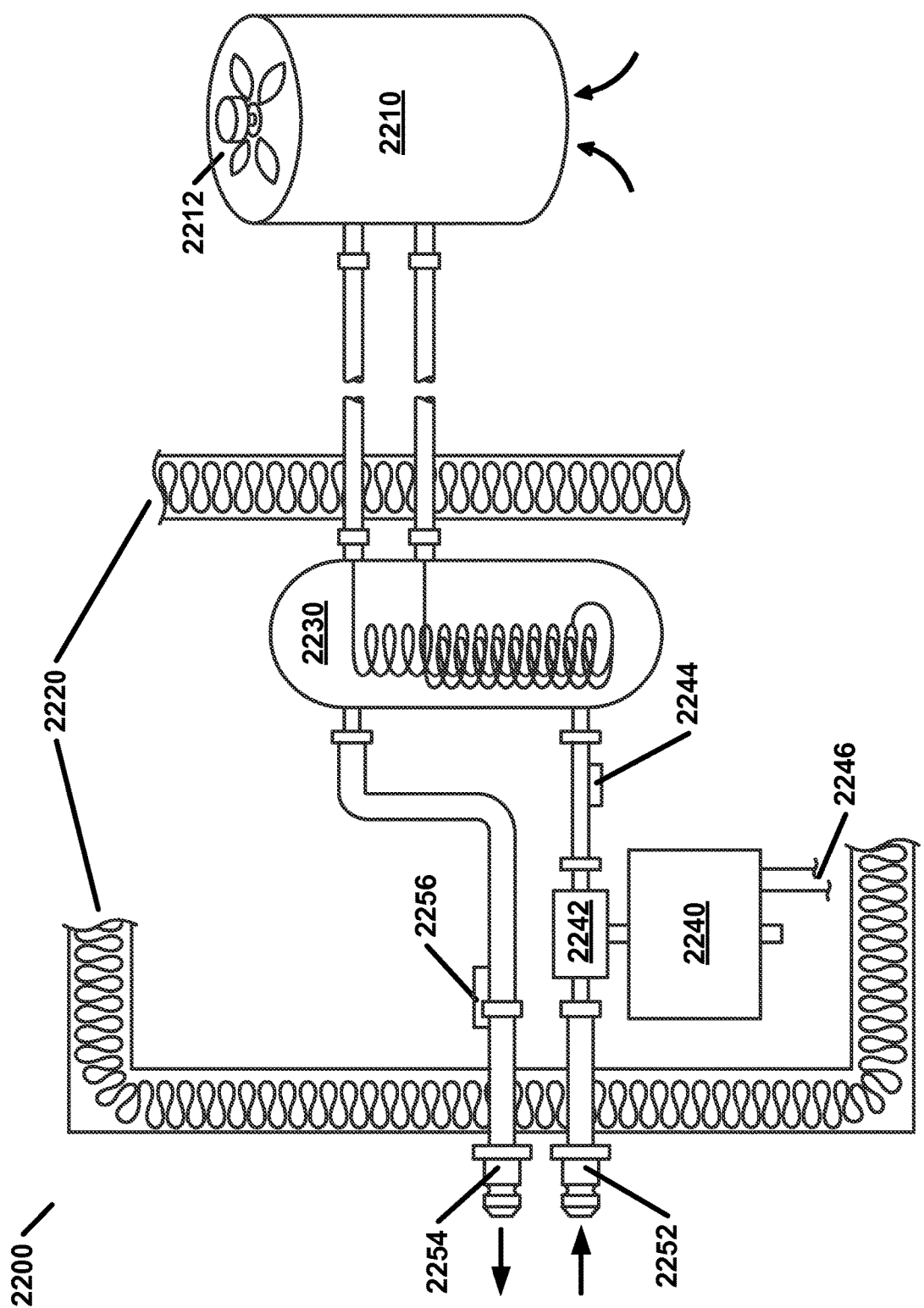
FIG. 22 is an illustration of an example remote enclosure according to an aspect of various embodiments.

FIG. 22 illustrates an example of a remote enclosure 2200 according to an aspect of various embodiments. The remote enclosure 2200 may comprise at least one sound reducing container 2220. The at least one remote enclosure 2200 may comprise at least one pump 2242. The at least one pump 2242 may comprise at least one pump servo motor 2240. The at least one pump servo motor 2240 may be configured to vary the flow rate of liquid(s), gel(s), air, and/or gas(es) incoming from or outgoing to the pillow (e.g. 210, 310). The at least one remote enclosure 2200 may comprise at least one incoming thermocouple 2244 configured to measure the temperature of liquid(s), gel(s), air, and/or gas(es) incoming from the pillow. The at least one remote enclosure 2200 may comprise at least one outgoing thermocouple 2256 configured to measure the temperature of liquid(s), gel(s), air, and/or gas(es) outgoing to at least one pillow. The at least one remote enclosure 2200 may comprise at least one heat exchanger 2230. The at least one heat exchanger 2230 may be coupled to at least one heat pump 2212. The at least one heat pump 2212 may be located remotely to the at least one heat exchanger 2230. The at least one heat pump 2212 may be housed in at least one independent remote enclosure 2210. The at least one remote enclosure 2200 may comprise at least one quick disconnect fitting (2252, 2254). Each of the at least one quick disconnect fitting (2252, 2254) may be configured to couple a tube to the pillow.

Some of the various embodiments may include at least one microphone. The at least one microphone may be configured to detect sounds, detect at least one sound frequency, measure a composite noise level, detect at least one voice command, a combination thereof, and/or the like, The at least one microphone may employ at least one filter configured to pass at least one frequency. The at least one microphone may be configured to detect snoring sounds produced by a user. The at least one microphone may, for example, employ an analog to digital converter device configured to convert a detected sound, a detected sound frequency, a detected voice command, and/or a measured composite noise level into a digital output. The digital output may be formatted in a representation that may be read by an observer or by an observer device. Alternatively, the at least one microphone may, for example, be configured to convert a detected sound, a detected sound frequency, and/or a measured composite noise level into an output voltage.

According to some of the various embodiments, the at least one microphone may be configured to communicate noise measurements. The noise measurements may be communicated according to a clock, at intervals required by a processing unit, at intervals required by a transceiver, at intervals specified by a remote device, at intervals specified by a second apparatus, at intervals selected by the user, a combination thereof, and/or the like. Alternatively, the measurements may be communicated after a sound, sound frequency, and/or noise level exceeds a threshold. The microphone may, for example, communicate noise measurements to the at least one processing unit (e.g. 150, 250, 350). According to some of the various embodiments, at least one microphone may, for example, be disposed outside the pillow. The noise measurements may comprise differential sound measurements, relative sound measurements, absolute sound measurements, a combination thereof, and/or the like. The measured composite noise level may comprise at least one decibel level.

Figure 23:
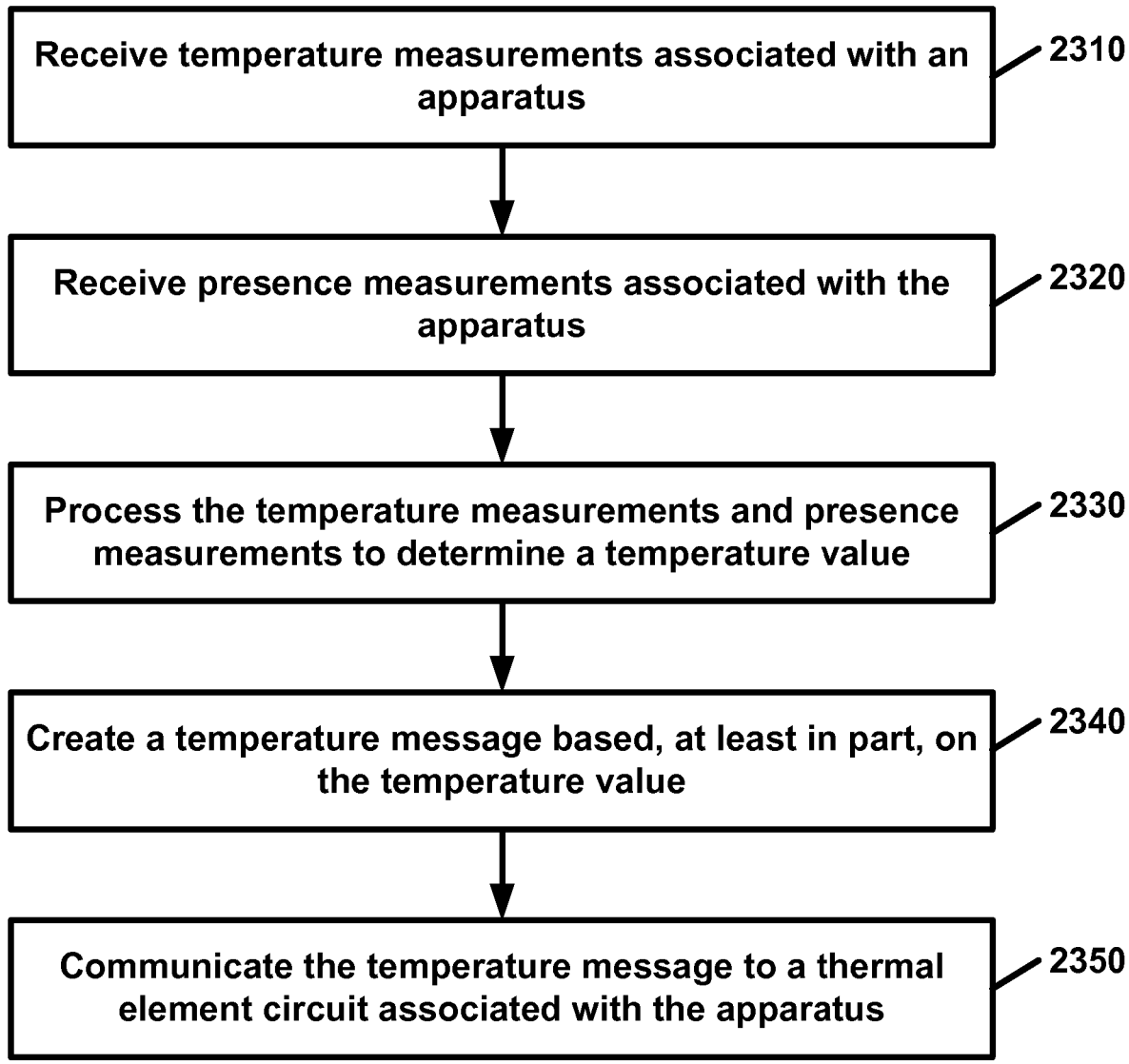
FIG. 23 is an example flow diagram of creating and communicating a temperature message as per an aspect of an embodiment.

FIG. 23 is an example flow diagram illustrating an embodiment for creating and communicating a temperature message. Temperature measurements associated with an apparatus may be received at block 2310. Presence measurements associated with an apparatus may be received at block 2320. At block 2330, the temperature measurements and presence measurements may be processed to determine a temperature value. At block 2340, a temperature message based, at least in part, on the temperature value may be created. The temperature message may be communicated to a thermal element circuit associated with the apparatus at block 2350.

Some of the various embodiments may include a non-transitory machine readable medium, at least one processor, and instructions. The non-transitory machine readable medium may, for example, be disposed in one of the following: a processing unit, another apparatus, a remote device, a combination thereof, and/or the like. The instructions may, for example, comprise receiving temperature measurements associated with an apparatus. According to some of the various embodiments, the temperature measurements may be taken using at least one temperature sensor. The instructions may also, for example, comprise receiving presence measurements associated with an apparatus. According to some of the various embodiments, the presence measurements may be taken using at least one presence sensor. The instructions may, for example, further comprise processing the temperature measurements and presence measurements to determine a temperature value. By way of example and not limitation, the temperature value may comprise a recommended temperature for at least one thermal element, a recommended temperature to achieve as measured by a temperature sensor as a result of activating at least one thermal element, the recommended temperature for at least one air chamber, a recommended temperature for at least one chamber filled with gel, a combination thereof, and/or the like. The at least one air chamber may comprise at least one gas.

According to some of the various embodiments, the instructions may further comprise receiving heart rate measurements associated with a user of an apparatus. The instructions may also, for example, comprise processing heart rate measurements. As per an aspect of various embodiments, the instructions may create a temperature message based, at least in part, on the temperature value. The instructions may, for example, further comprise communicating the temperature message to a thermal element circuit. The temperature message may, for example, comprise at least one temperature value for a specific thermal element, a single temperature value for a plurality of thermal elements, a plurality of temperature values for a plurality of thermal elements, a combination thereof, and/or the like. The temperature message may, for example, also comprise instructions for a processing unit or a controller to activate at least one thermal element. By way of example and not limitation, the temperature message may be communicated from the at least one processing unit (e.g. 150, 250, 350), a second apparatus, a remote device, a combination thereof, and/or the like.

Figure 24:
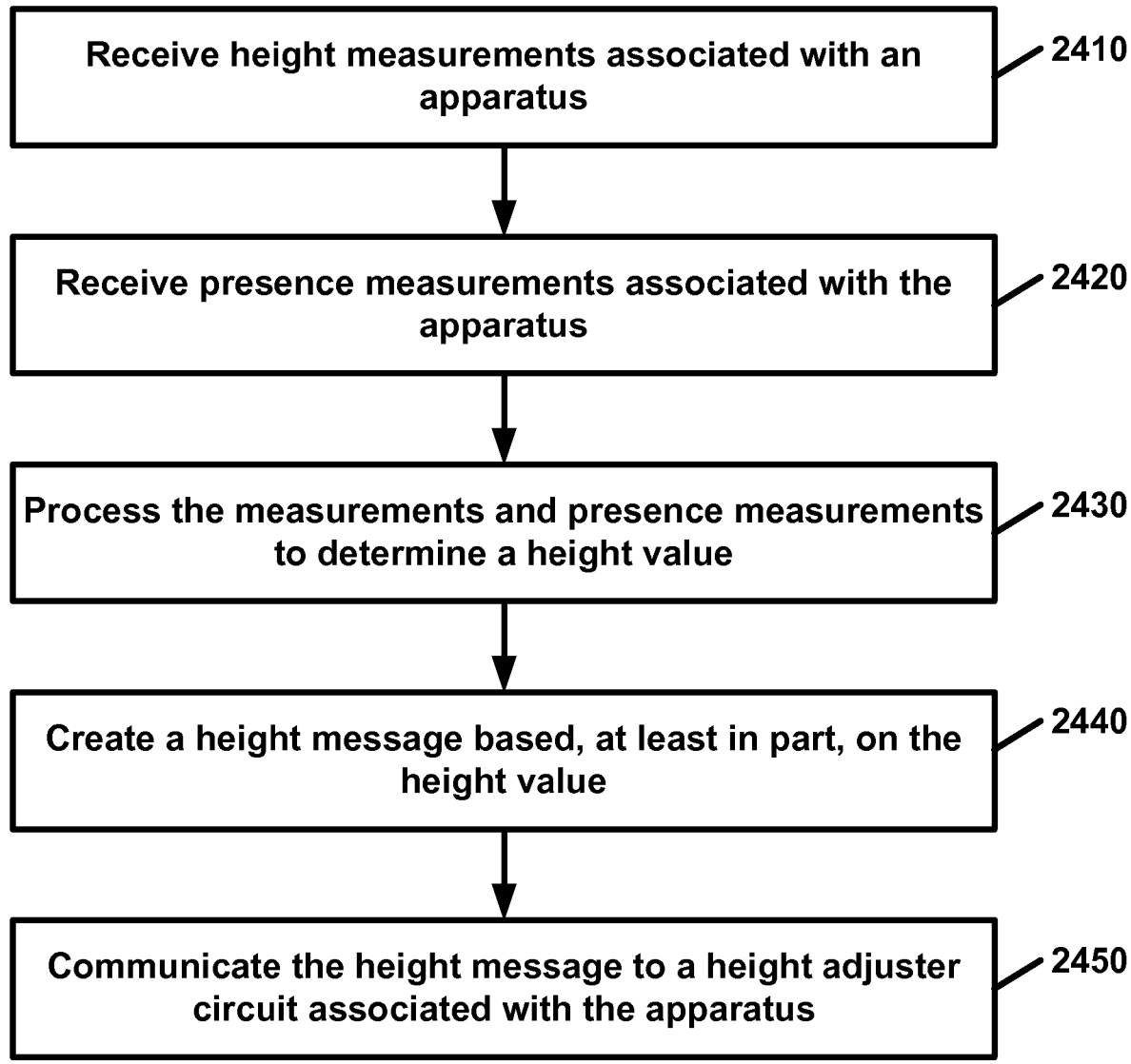
FIG. 24 is an example flow diagram of creating and communicating a height message as per an aspect of an embodiment.

FIG. 24 is an example flow diagram illustrating an embodiment for creating and communicating a height message as per an aspect of an embodiment. Height measurements associated with an apparatus may be received at block 2410. Presence measurements associated with an apparatus may be received at block 2420. At block 2430, the height measurements and presence measurements may be processed to determine a height value. At block 2440, a height message based, at least in part, on the height value may be created. The height message may be communicated to a height adjuster circuit associated with the apparatus at block 2450.

Some of the various embodiments may include a non-transitory machine readable medium, at least one processor, and instructions. The non-transitory machine readable medium may, for example, be disposed in one of the following: a processing unit (e.g. 150, 250, 350), another apparatus, a remote device, a combination thereof, and/or the like. The instructions may, for example, comprise receiving height measurements associated with an apparatus. According to some of the various embodiments, the height measurements may be taken using at least one pillow height sensor. The instructions may also, for example, comprise receiving presence measurements associated with an apparatus. According to some of the various embodiments, the presence measurements may be taken using at least one presence sensor. The instructions may, for example, further comprise processing the height measurements and presence measurements to determine a height value. By way of example and not limitation, the height value may comprise a recommended height for at least one pillow height adjuster, a recommended height to achieve as measured by a pillow height sensor as a result of activating at least one pillow height adjuster, a recommended height for at least one component of a pillow height adjuster, a combination thereof, and/or the like.

According to some of the various embodiments, the instructions may further comprise receiving heart rate measurements associated with a user of an apparatus. The instructions may also, for example, comprise processing heart rate measurements. As per an aspect of various embodiments, the instructions may create a height message based, at least in part, on the height value. The instructions may, for example, further comprise communicating the height message to a height adjuster circuit. The height message may, for example, comprise at least one height value for a specific pillow height adjuster, a single height value for a plurality of pillow height adjusters, a plurality of height values for a plurality of pillow height adjusters, a combination thereof, and/or the like. The height message may, for example, also comprise instructions for a processing unit or a controller to activate at least one pillow height adjuster. By way of example and not limitation, the height message may be communicated from the at least one processing unit (e.g. 150, 250, 350), a second apparatus, a remote device, a combination thereof, and/or the like.

The height adjuster circuit may, for example, be associated with an apparatus. By way of example and not limitation, the height adjuster circuit may comprise a controller electrically coupled to at least one pillow height adjuster. Alternatively, the height adjuster circuit may, for example, comprise a processing unit electrically coupled to at least one pillow height adjuster. According to some of the various embodiments, the apparatus may comprise at least one pillow.

According to some of the various embodiments, the activation of a thermal element may be based, at least in part, on temperature measurements and presence measurements over at least one period of time. By way of example and not limitation, a user may experience at least one sleep interruption event such as waking during sleep to turn over, sitting up, getting up to use a restroom, a combination thereof, and/or the like. Each of these example events may, for example, correlate to different presence measurements. The presence measurements may, for example, be configured to estimate the breathing patterns of the user. Breathing pattern estimations may, for example, be employed in the activation of a thermal element. Furthermore, each of these example events may, for example, require changes in the activation of a thermal element to maintain a temperature setting. The activation of a thermal element may depend upon user settings (e.g. user profile information), user inputs, derived values, a combination thereof, and/or the like. The activation of a thermal element may, for example, also depend upon heart rate measurements taken from a wearable device. So for example, if a heart rate measurement increases and/or decreases beyond a threshold, the thermal element may be configured to activate and/or deactivate. Activation may comprise adjusting a temperature of the thermal element to an active level less than a maximum level but greater than a minimum level.

According to some of the various embodiments, the activation of a pillow height adjuster may be based, at least in part, on height measurements and presence measurements over at least one period of time. The presence measurements may, for example, be configured to estimate the breathing patterns of the user. Breathing pattern estimations may, for example, be used in the activation of a pillow height adjuster. By way of example and not limitation, a user may prefer a consistent height setting for an entire sleeping session. The activation of a pillow height adjuster may, for example, depend upon user settings, user inputs, derived values, a combination thereof, and/or the like. The activation of a pillow height adjuster may, for example, also depend upon heart rate measurements taken from a wearable device.

Instructions associated with the wearable device may, for example, be configured to cause at least one processor to communicate with at least one sensor, receive input from a user, display information, communicate with an apparatus, communicate with a remote device, transmit at least one of temperature and height messages to an apparatus, or any combination thereof.

Instructions may, for example, further comprise developing and presenting a plurality of reports. For example, reports of temperature measurements, presence measurements, height measurements, a combination thereof, and/or the like, may be generated. The reports may be generated, for example, in a processing unit, a second apparatus, a remote device, a combination thereof, and/or the like. Reports may, for example, contain at least one of the following report data for at least one user: temperature measurements, height measurements, time elapsed at a given temperature, time elapsed on at least one presence sensor, time elapsed at a given height, time of day, heart rate measurements, at least one sleep cycle phase, duration of at least one sleep cycle phase, at least one sleeping session, duration of at least one sleeping session, recommended temperature, recommended height, recommended number of sleep cycle phases, recommended duration of sleeping session, a recommended wake time, user specific information, a combination thereof, and/or the like. The report data may be transmitted to a display and/or remote device via at least one report message.

Instructions may, for example, further comprise presenting information on a display. A display may, for example, be located on an apparatus, on a second apparatus, on a remote device, on a pillow, on a support structure located under the pillow, a support structure surrounding the pillow, a combination thereof, and/or the like. The information presented may, for example, comprise at least one of the following for at least one user: temperature measurements from at least one wearable device, temperature measurements from at least one apparatus, presence measurements from at least one wearable device, presence measurements from at least one apparatus, height measurements from at least one apparatus, heart rate measurements, time of day, current sleep cycle phase, elapsed time of current sleep cycle phase, elapsed time of current sleeping session, remaining time in current sleep cycle phase, remaining time in current sleeping session, remaining sleep cycle phases, recommended temperature setting, recommended height setting, recommended wake time, user specific information, a combination thereof, and/or the like. The information may be transmitted to a display via at least one display message.

Figure 25:
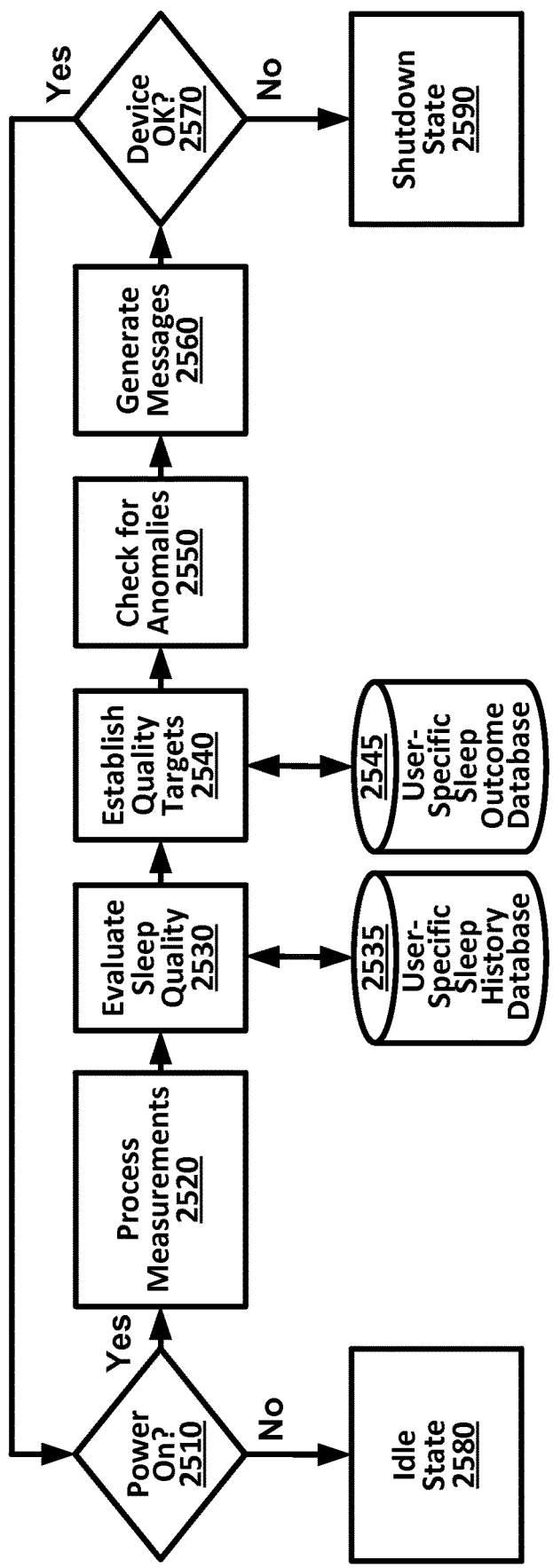
FIG. 25 is an example flow diagram of processing measurements and generating messages according to aspects of various embodiments.

FIG. 25 is an example flow diagram illustrating an embodiment of a system configured to process measurements and generate messages according to aspects of various embodiments. The system may be configured to check a power state at decision 2510. The system may be configured to power on automatically, power off automatically, accept manual power input from a user, combinations thereof, and/or the like. The system may be configured to maintain an idle state at 2580. The system may be configured to check for normal system operation at decision 2570. The system may be configured to perform a system shutdown at 2590. The system may be configured to accept and process measurements at 2520. The system may be configured to evaluate sleep quality for at least one user at 2530. Evaluation of sleep quality may employ data from a user-specific sleep history database 2535. The system may be configured to establish sleep quality targets at 2540. Establishing sleep quality targets may employ data from a user-specific sleep outcome database 2545. The system may be configured to check for anomalies at 2550. The system may be configured to generate messages at 2560.

Figure 26:
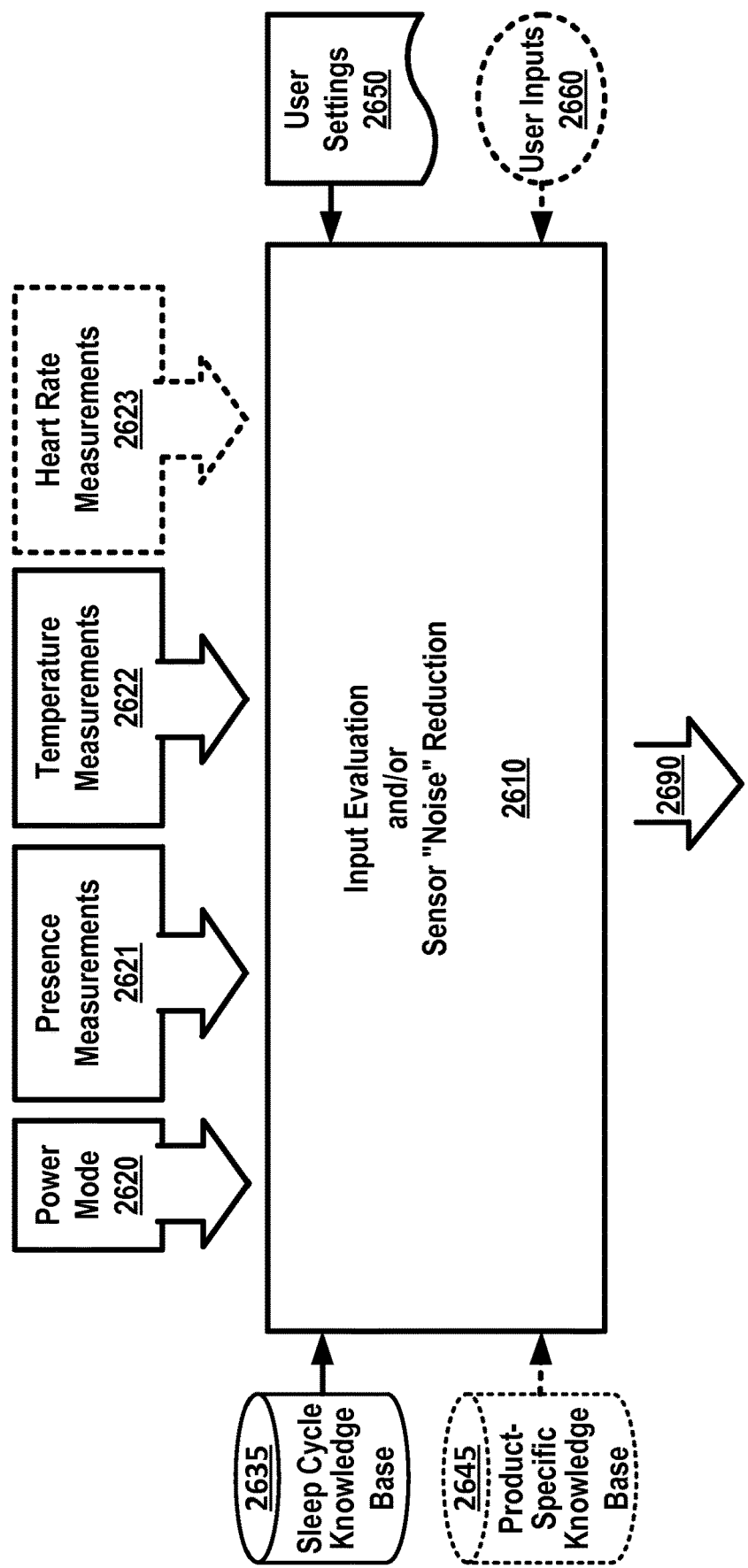
FIG. 26 is an example flow diagram of processing sensor measurements according to aspects of various embodiments.

FIG. 26 is an example flow diagram illustrating an example system configured to process sensor measurements according to aspects of various embodiments. The system may be configured to accept the following inputs: system power mode 2620, presence measurements 2621, and temperature measurements 2622. The system may be further configured to accept heart rate measurements 2623. The system may be configured to cause at least one processing unit (e.g. 150, 250, 350) to evaluate inputs at 2610. The system may be configured to employ at least one user settings 2650, sleep cycle knowledge base 2635, and/or product-specific knowledge base 2645 to evaluate inputs at 2610. The system may be configured to cause at least one processing unit (e.g. 150, 250, 350) to reduce sensor noise at 2610. The system may be configured to employ user settings 2650, sleep cycle knowledge base 2635, and/or product-specific knowledge base 2645 to reduce sensor noise at 2610. The system may be configured to produce a plurality of outputs 2690 for further processing. An example of further processing is described with respect to FIG. 27.

Input evaluation may, for example, comprise detecting the presence of a user. Sensor noise reduction may be employed, for example, to filter out presence measurements 2621 that fall above or below at least one threshold, or fall outside of at least one threshold range. Presence measurements 2621 that register as noise may, for example, comprise measurements of pets, bedding materials, a hand of a user during use of a pillow, an arm of a user during use of a pillow, combinations thereof, and/or the like. Sensor noise reduction may, for example, comprise an average of inputs over time, an elimination of extreme values, a normalized range of measurements, combinations thereof, and/or the like. Furthermore, sensor noise reduction may employ user settings 2650, sleep cycle knowledge base 2635, and/or product-specific knowledge base 2645 to set thresholds and/or threshold ranges for noise measurements.

The plurality of outputs 2690 for further processing may comprise filtered temperature measurements. Filtered temperature measurements may comprise at least a subset of temperature measurements 2622. The system may be further configured to employ user inputs 2660 to construct at least one filtered temperature measurement. For example, a user may prefer a warmer temperature than a system temperature produced without the user input. Alternatively, a user may prefer a cooler temperature than a system temperature produced without the user input. The system may be configured to accept user inputs 2660 indefinitely, during a sleeping session, during a sleeping cycle, combinations thereof, and/or the like. The system may be further configured to employ at least one product-specific data from product-specific knowledge base 2645 to estimate a body temperature of a user. For example, a temperature sensor from a known location in a pillow may be associated with a known energy coefficient. The known energy coefficient may, for example, be employed to estimate a body temperature of the user given at least a subset of temperature measurements 2622 from the temperature sensor.

The plurality of outputs 2690 for further processing may comprise filtered presence measurements. Filtered presence measurements may comprise at least a subset of the presence measurements 2621. The system may be configured to employ user settings 2650 to reduce sensor noise at 2610 from the presence measurements 2621. For example, a user height, weight, gender, user calibration information, combinations thereof, and/or the like may be employed to set at least one filter threshold and/or at least one threshold range. Similarly, the plurality of outputs 2690 for further processing may comprise filtered heart rate measurements. The filtered heart rate measurements may comprise at least a subset of the heart rate measurements 2623. The system may be configured to employ user settings 2650 to reduce sensor noise at 2610 from the heart rate measurements 2623. For example, a user weight, gender, age, combinations thereof, and/or the like may be employed to set at least one filter threshold and/or at least one threshold range. The system may be further configured to employ at least one filtered presence measurement (2621) and at least one product-specific data from product-specific knowledge base 2645 to determine at least one interruption event. The system may be further configured to employ at least one filtered presence measurement and at least one sleep cycle data from sleep cycle knowledge base 2635 to estimate at least one estimated current sleep cycle phase and/or to estimate at least one estimated current sleep cycle number. The estimated current sleep cycle phase may, for example, be based at least in part on at least one of: a time related to at least one sleep cycle, a time related to at least one sleeping session, a time of day, an estimated body temperature, expected body temperature, combinations thereof, and/or the like.

The plurality of outputs 2690 for further processing may comprise at least one estimated confidence level. The at least one estimated confidence level may, for example, be based at least in part on at least one of: at least one presence measurement, at least one temperature measurement, at least one estimated body temperature, at least one heart rate measurement, at least one interruption event, at least one estimated current sleep cycle phase, at least one estimated current sleep cycle number, at least one sleep cycle knowledge data, combinations thereof, and/or the like. For example, rapid fluctuations in sensor measurements, unusual patterns in sensor measurements, unusual patterns in estimation results, combinations thereof, and/or the like, may be employed to lower an estimated confidence level. In another example, a plurality of determined interruption events may be compared to a plurality of historical interruption events for an estimated current sleep cycle phase and/or an estimated sleep cycle number to estimate a confidence level. According to some of the various embodiments, the system may employ at least one simple average, at least one time-weighted average, at least one Bayesian network, at least one neural network, combinations thereof, and/or the like, to make estimations and/or determinations. Estimations and/or determinations corresponding to a low confidence level may, for example, be filtered, ignored, recalculated, combinations thereof, and/or the like.

Figure 27:
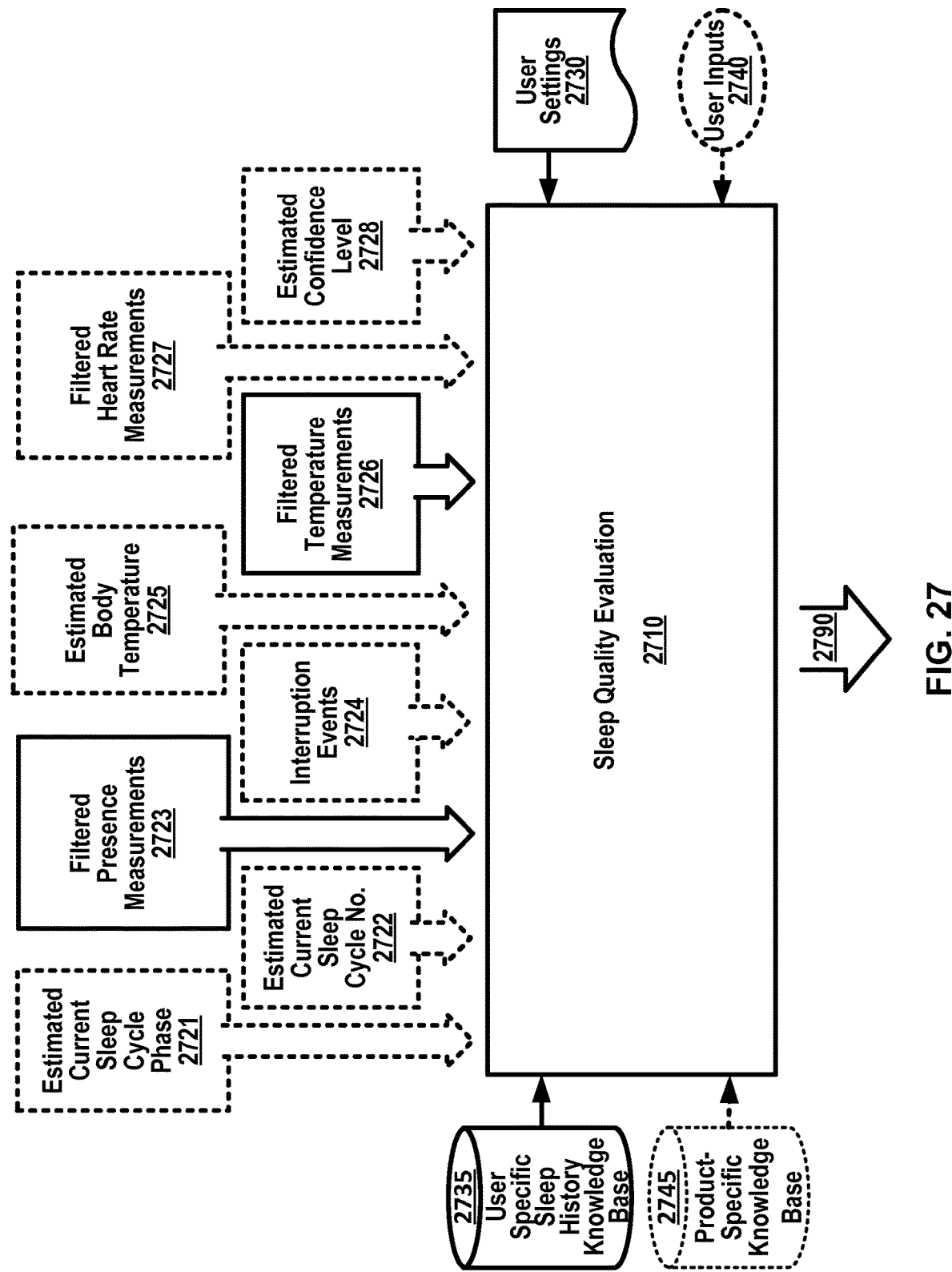
FIG. 27 is an example flow diagram of performing a sleep quality evaluation according to aspects of various embodiments.

FIG. 27 is an example flow diagram illustrating a system configured to perform a sleep quality evaluation at 2710 employing a plurality of inputs (e.g. 2721, 2722 . . . 2728) according to aspects of various embodiments. The system may be configured to accept the following inputs: filtered presence measurements 2723, and filtered temperature measurements 2726. The system may be further configured to accept at least one of: an estimated current sleep cycle phase 2721, an estimated current sleep cycle number 2722, interruption events 2724, at least one estimated body temperature 2725, filtered heart rate measurements 2727, at least one estimated confidence level 2728, a combination thereof, and/or the like. The system may be configured to cause at least one processing unit (e.g. 150, 250, 350) to evaluate sleep quality at 2710. The system may be configured to employ user settings 2730, user-specific sleep history knowledge base 2735, and/or product-specific knowledge base 2745 to evaluate sleep quality at 2710. The system may be configured to produce a plurality of outputs 2790 for further processing. An example of further processing is described with respect to FIG. 28.

Sleep quality evaluation may, for example, comprise estimating a current sleep quality. The current sleep quality may, for example, be based at least in part on filtered presence measurements 2723. Estimating current sleep quality may, for example, be based at least in part on at least one of: an estimated current sleep cycle phase 2721, an estimated current sleep cycle number 2722, interruption events 2724, filtered heart rate measurements 2727, combinations thereof, and/or the like. User-specific sleep history data from user-specific sleep history knowledge base 2735 may be employed to estimate the current sleep quality. Sleep quality evaluation may, for example, comprise estimating a cumulative sleep quality. Cumulative sleep quality may, for example, be based at least in part on user-specific sleep history data from user-specific sleep history knowledge base 2735 and the current sleep quality. Sleep quality evaluation may, for example, comprise estimating an ideal sleep quality. Ideal sleep quality may, for example, be based at least in part on at least one of: user-specific sleep history data from user-specific sleep history knowledge base 2735, product-specific data from product-specific knowledge base 2745, user settings 2730, combinations thereof, and/or the like.

The plurality of outputs 2790 for further processing may comprise a recommended temperature. Recommended temperature may, for example, be based at least in part on at least one of: the current sleep quality, an ideal sleep quality, filtered temperature measurements 2726, combinations thereof, and/or the like. Recommended temperature may, for example, be based at least in part on user input(s) 2740. By way of example and not limitation, user inputs 2740 may comprise a minimum temperature, a maximum temperature, a desired temperature, a minimum number of sleep cycles, a maximum number of sleep cycles, a desired number of sleep cycles, combinations thereof, and/or the like. The recommended temperature may, for example, be based at least in part on user-specific sleep history data from user-specific sleep history knowledge base 2735. The user-specific sleep history data may, for example, correlate to an estimated current sleep cycle phase 2721 and/or an estimated current sleep cycle number 2722. The recommended temperature may, for example, be based at least in part on an estimated confidence level 2728.

Sleep quality evaluation may, for example, comprise estimating an ideal body temperature. Ideal body temperature may, for example, be based at least in part on at least one estimated body temperature 2725. Ideal body temperature may, for example, be based at least in part on at least one of: user-specific sleep history data from user-specific sleep history knowledge base 2735, product-specific data from product-specific knowledge base 2745, user settings 2730, combinations thereof, and/or the like. The plurality of outputs 2790 for further processing may comprise a recommended body temperature. The recommended body temperature may, for example, be based at least in part on an ideal body temperature and at least one estimated body temperature 2725. The recommended body temperature may, for example, be based at least in part on an estimated confidence level 2728.

The plurality of outputs 2790 for further processing may comprise the estimated current sleep quality and the estimated cumulative sleep quality. Sleep quality evaluation may, for example, comprise determining a recommended sleep quality. Recommended sleep quality may, for example, be based at least in part on at least one of: the estimated current sleep quality, the estimated cumulative sleep quality, the ideal sleep quality, combinations thereof, and/or the like. According to some of the various embodiments, the recommended sleep quality may be based at least in part on an estimate of cumulative Rapid Eye Movement (REM) time and/or REM quality. Cumulative REM time may be determined for at least one sleep cycle phase, at least one sleep cycle number, at least one sleeping session, combinations thereof, and/or the like. REM quality may be determined for at least one sleep cycle phase, at least one sleep cycle number, at least one sleeping session, at least one interruption event, combinations thereof, and/or the like. Data related to cumulative REM time and/or REM quality may be stored in user-specific sleep history knowledge base 2735. User-specific sleep history data from user-specific sleep history knowledge base 2735 may be employed to estimate the cumulative REM time. Furthermore, user settings 2730 may be employed to estimate the cumulative REM time. The recommended sleep quality may, for example, be based at least in part on an estimated confidence level 2728.

Figure 28:
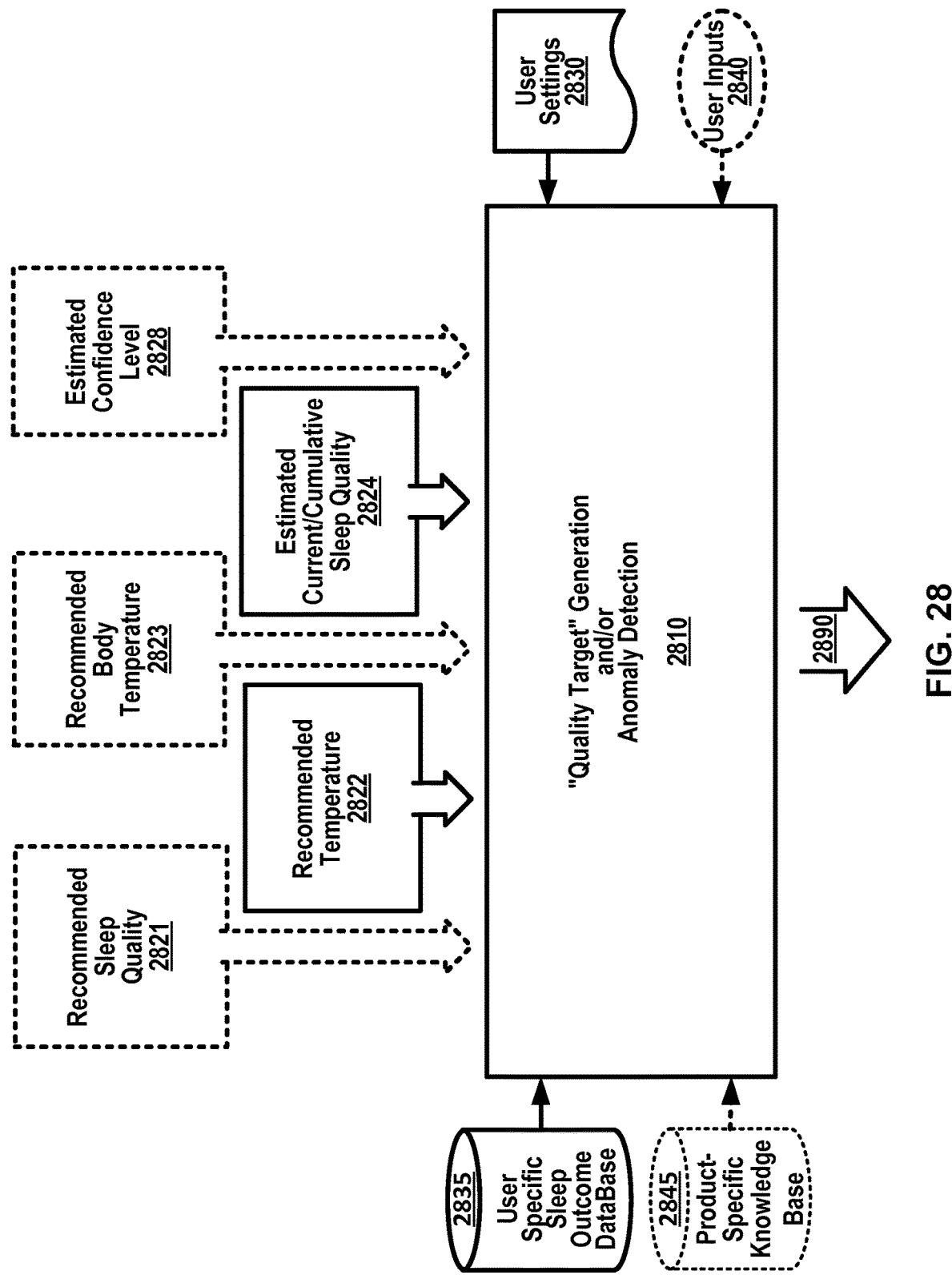
FIG. 28 is an example flow diagram of generating quality targets according to aspects of various embodiments.

FIG. 28 is an example flow diagram illustrating a system configured to generate quality targets at 2810 employing a plurality of inputs (e.g. 2821, 2822 . . . 2828) according to aspects of various embodiments. The system may be further configured to detect anomalies at 2810. The system may be configured to accept the following inputs: recommended temperature 2822 and estimated current and/or cumulative sleep quality 2824. The system may be further configured to accept at least one of: at least one recommended sleep quality 2821, at least one recommended body temperature 2823, at least one estimated confidence level 2828, a combination thereof, and/or the like. The system may be configured to cause at least one processing unit (e.g. 150, 250, 350) to perform quality target generation and anomaly detection at 2810. The system may be configured to employ user settings 2830, user-specific sleep outcome database 2835, and/or product-specific knowledge base 2845 to generate quality targets and/or detect anomalies at 2810. The system may be configured to produce a plurality of outputs 2890 for further processing. An example of further processing is described with respect to FIG. 29.

Generating quality targets may, for example, comprise employment of product-specific data from product-specific knowledge base 2845 to calculate calibration adjustments. Product-specific data may, for example, be employed to calibrate at least one recommended temperature and/or at least one recommended body temperature. The product-specific data may, for example, comprise product-specific calibration data, sensor-specific calibration data, at least one maximum rate of temperature change, at least one power utilization minimum, at least one power utilization maximum, at least one power utilization target, combinations thereof, and/or the like. Generating quality targets may, for example, comprise employment of user settings 2830. User settings 2830 may, for example, comprise user calibration data. The user calibration data may, for example, be employed to calibrate at least one recommended temperature and/or at least one recommended body temperature. Generating quality targets may, for example, comprise employment of user inputs 2840. User inputs 2840 may, for example, comprise at least one manual override. The at least one manual override may, for example, be employed to adjust at least one recommended temperature and/or at least one recommended body temperature.

Generating quality targets may, for example, comprise calculating a difference between an estimated current and/or cumulative sleep quality and a recommended sleep quality. The difference may, for example, be employed to detect anomalies at 2810. Anomalies may, for example, be filtered, ignored, recalculated, combinations thereof, and/or the like.

The plurality of outputs 2890 for further processing may, for example, comprise at least one action to achieve a recommended temperature. The action to achieve a recommended temperature may, for example, be based at least in part on a calibrated input. The action to achieve a recommended temperature may, for example, be based at least in part on product-specific data from product-specific knowledge base 2845. The product-specific data may, for example, be related to at least one thermal element (e.g. 140, 240, 340). The action to achieve a recommended temperature may, for example, be based at least in part on at least one of: at least one user input 2840. The at least one user input 2840 may, for example, comprise a minimum temperature, a maximum temperature, a desired temperature, a maximum rate of temperature change, combinations thereof, and/or the like. Similarly, the plurality of outputs 2890 for further processing may, for example, comprise at least one action to achieve a recommended body temperature.

The plurality of outputs 2890 for further processing may, for example, comprise at least one recommendation to achieve sleep quality. The at least one recommendation to achieve sleep quality may, for example, be based at least in part on at least one of: a recommended sleep quality 2821, an estimated current sleep quality 2824, an estimated cumulative sleep quality 2824, combinations thereof, and/or the like. By way of example and not limitation, the recommendation to achieve sleep quality may comprise a recommended number of sleep cycles per sleeping session, a recommended start time for a sleeping session, a recommended wake time, combinations thereof, and/or the like.

Figure 29:
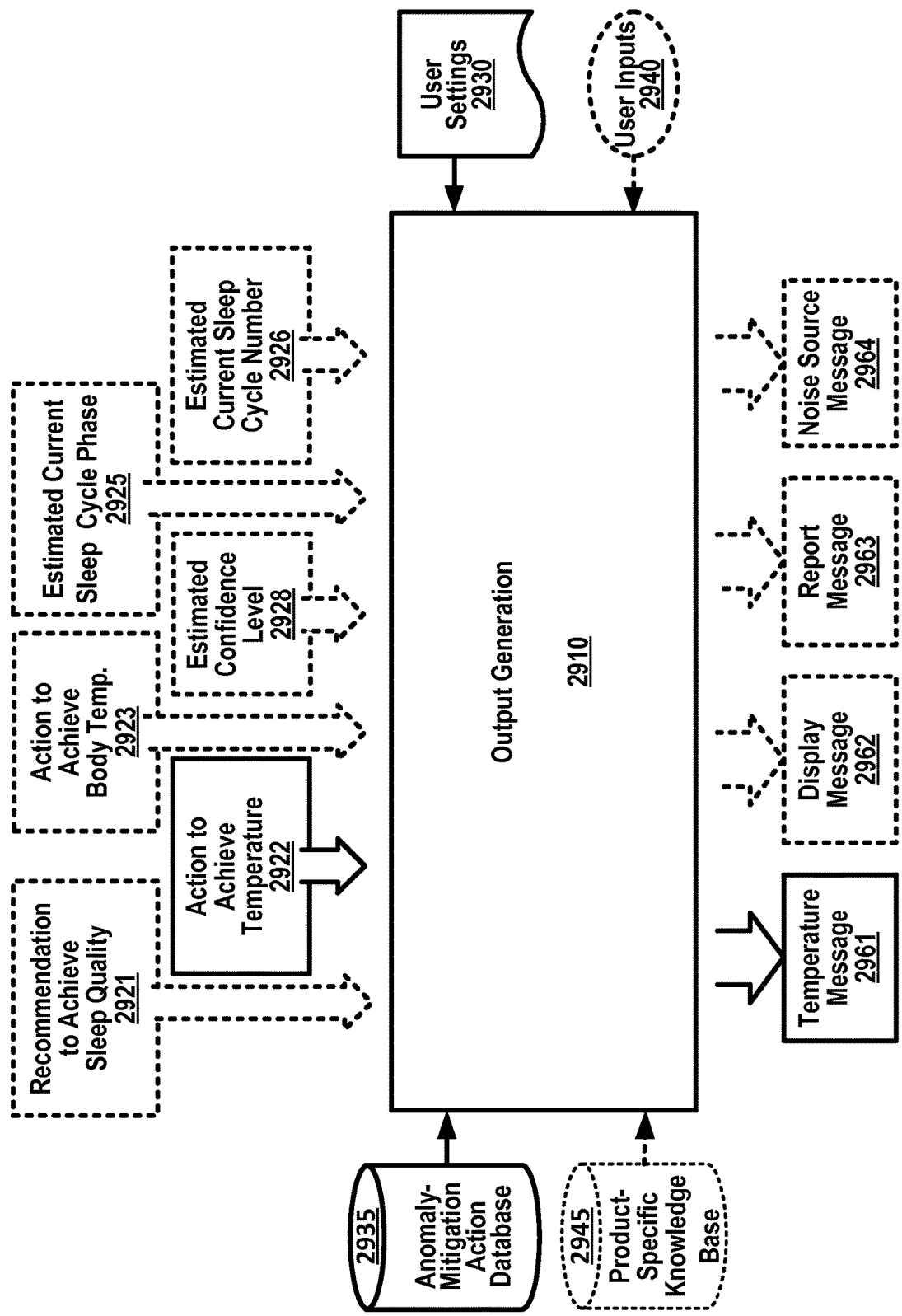
FIG. 29 is an example flow diagram of generating outputs according to aspects of various embodiments.

FIG. 29 is an example flow diagram illustrating a system configured to generate output 2910 employing a plurality of inputs (e.g. 2921, 2922 . . . 2928) according to aspects of various embodiments. The system may be configured to accept at least one action to achieve temperature 2922 as input. The system may be further configured to accept at least one of: at least one recommendation to achieve sleep quality 2921, at least one action to achieve body temperature 2923, an estimated current sleep cycle phase 2925, an estimated current sleep cycle number 2926, at least one estimated confidence level 2928, a combination thereof, and/or the like. The system may be configured to cause at least one processing unit (e.g. 150, 250, 350) to generate output at 2910. The system may be configured to employ user settings 2930, anomaly mitigation action database 2935, product-specific knowledge base 2945, and/or user inputs 2940 to generate output at 2910. The at least one user input 2940 may, for example, depend on the estimated current sleep cycle phase 2925 and/or the estimated current sleep cycle number 2926.

Output generation at 2910 may comprise generating at least one temperature message 2961. The at least one temperature message 2961 may, for example, be based at least in part on at least one action to achieve temperature 2922. The at least one temperature message 2961 may, for example, be based at least in part on at least one action to achieve body temperature 2923.

Output generation at 2910 may comprise generating at least one display message 2962. The at least one display message 2962 may, for example, be based at least in part on at least one of: at least one recommendation to achieve sleep quality 2921, at least one action to achieve temperature 2922, at least one action to achieve body temperature 2923, an estimated current sleep cycle phase 2925, an estimated current sleep cycle number 2926, combinations thereof, and/or the like.

Output generation at 2910 may comprise generating at least one report message 2963. The at least one report message 2963 may, for example, be based at least in part on at least one of: at least one recommendation to achieve sleep quality 2921, at least one action to achieve temperature 2922, at least one action to achieve body temperature 2923, an estimated current sleep cycle phase 2925, an estimated current sleep cycle number 2926, at least one user setting 2930, at least one user input 2940, combinations thereof, and/or the like.

Output generation at 2910 may comprise generating at least one noise source message 2964. The at least one noise source message 2964 may, for example, be based at least in part on at least one of: at least one recommendation to achieve sleep quality 2921, at least one estimated current sleep cycle phase 2925, at least one estimated current sleep cycle number 2926, at least one user setting 2930, at least one user input 2940, combinations thereof, and/or the like. Generation of noise source messages may be restricted during specific sleep cycle phases 2925 and/or specific sleep cycle numbers 2926. For example, noise source messages configured to instruct at least one noise source to create at least one sound may be restricted during estimated periods of REM sleep.

Figure 30:
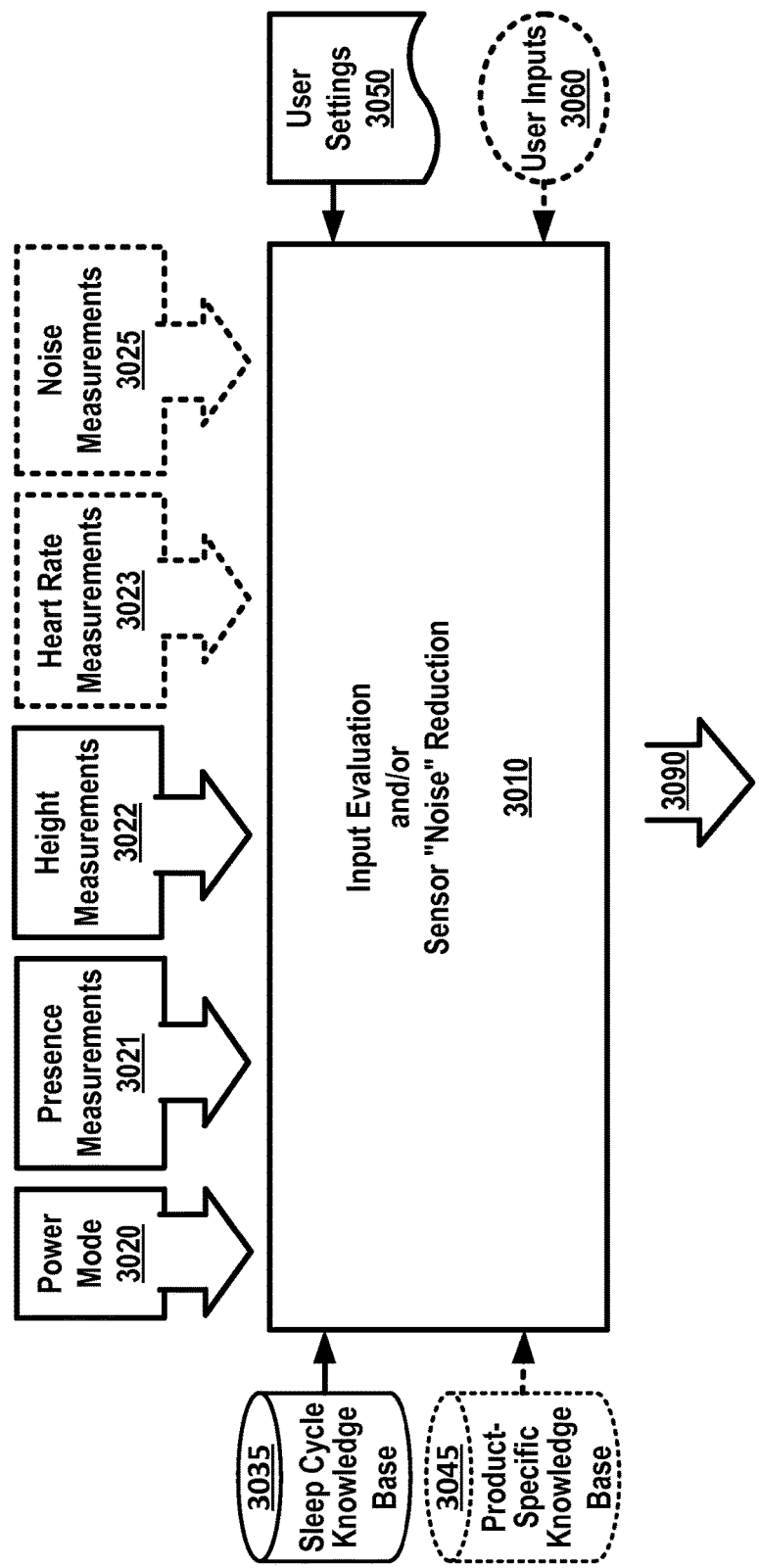
FIG. 30 is an example flow diagram of processing sensor measurements according to aspects of various embodiments.

FIG. 30 is an example flow diagram illustrating a system configured to process sensor measurements according to aspects of various embodiments. The system may be configured to accept the following inputs: system power mode 3020, presence measurements 3021, and height measurements 3022. The system may be further configured to accept heart rate measurements 3023 and/or noise measurements 3025. The system may be configured to cause at least one processing unit (e.g. 150, 250, 350) to evaluate inputs at 3010. The system may be configured to employ at least one user setting 3050, sleep cycle knowledge base 3035, and/or product-specific knowledge base 3045 to evaluate inputs at 3010. The system may be configured to cause at least one processing unit (e.g. 150, 250, 350) to reduce sensor noise at 3010. The system may be configured to employ user settings 3050, sleep cycle knowledge base 3035, and/or product-specific knowledge base 3045 to reduce sensor noise at 3010. The system may be configured to produce a plurality of outputs 3090 for further processing. An example of further processing is described with respect to FIG. 31.

Input evaluation may, for example, comprise detecting the presence of a user. Sensor noise reduction may be employed, for example, to filter out presence measurements that fall above or below at least one threshold, or fall outside of at least one threshold range. Presence measurements that register as noise may, for example, include measurements of pets, bedding materials, a hand of a user during use of a pillow, an arm of a user during use of a pillow, combinations thereof, and/or the like. Sensor noise reduction may, for example, comprise an average of inputs over time, an elimination of extreme values, a normalized range of measurements, combinations thereof, and/or the like. Furthermore, the sensor noise reduction may employ user settings 3050, sleep cycle knowledge base 3035, and/or product-specific knowledge base 3045 to set thresholds and/or threshold ranges for noise measurements.

The plurality of outputs 3090 for further processing may comprise filtered height measurements. The filtered height measurements may comprise at least a subset of the height measurements 3022. The system may be further configured to employ user inputs 3060 to construct at least one filtered height measurement. For example, a user may prefer a taller height than a system height produced without the user input. Alternatively, a user may prefer a shorter height than a system height produced without the user input. The system may be configured to accept user inputs 3060 indefinitely, during a sleeping session, during a sleeping cycle, combinations thereof, and/or the like. The system may be further configured to employ at least one product-specific data from product-specific knowledge base 3045 to estimate a position of a user. For example, presence measurements 3021 from a presence sensor configured to detect presence in a plurality of zones identified on a pillow may be received. The at least one product-specific data may, for example, comprise information related to the presence sensor, information related to the plurality of zones identified on a pillow, calibration information, combinations thereof, and/or the like. The at least one product-specific data may be employed to estimate a position of a user.

The plurality of outputs 3090 for further processing may comprise filtered presence measurements. The filtered presence measurements may comprise at least a subset of the presence measurements 3021. The system may be configured to employ user settings 3050 to reduce sensor noise 3010 from the presence measurements 3021. For example, a user height, weight, gender, user calibration information, combinations thereof, and/or the like may be employed to set at least one filter threshold and/or at least one threshold range. Similarly, the plurality of outputs 3090 for further processing may comprise filtered heart rate measurements. The filtered heart rate measurements may comprise at least a subset of the heart rate measurements 3023. The system may be configured to employ user settings 3050 to reduce sensor noise 3010 from the heart rate measurements 3023. For example, a user weight, gender, age, combinations thereof, and/or the like may be employed to set at least one filter threshold and/or at least one threshold range. The system may be further configured to employ at least one filtered presence measurement and at least one product-specific data from product-specific knowledge base 3045 to determine at least one interruption event. The system may be further configured to employ at least one filtered presence measurement and at least one sleep cycle data from sleep cycle knowledge base 3035 to estimate at least one estimated current sleep cycle phase and/or to estimate at least one estimated current sleep cycle number. The estimated current sleep cycle phase may, for example, be based at least in part on at least one of: a time related to at least one sleep cycle, a time related to at least one sleeping session, a time of day, an estimated position of a user, an expected position of a user, combinations thereof, and/or the like. The at least one estimated current sleep cycle phase and/or the at least one estimated current sleep cycle number may, for example, be employed to qualify at least one interruption event.

The plurality of outputs 3090 for further processing may comprise at least one estimated confidence level. The at least one estimated confidence level may, for example, be based at least in part on at least one of: at least one presence measurement, at least one height measurement, at least one heart rate measurement, at least one noise measurement, at least one interruption event, at least one estimated current sleep cycle phase, at least one estimated current sleep cycle number, at least one user position, at least one sleep cycle knowledge data, combinations thereof, and/or the like. For example, a plurality of determined interruption events may be compared to a plurality of historical interruption events for an estimated current sleep cycle phase and/or an estimated sleep cycle number to estimate a confidence level. According to some of the various embodiments, the system may employ at least one simple average, at least one time-weighted average, at least one Bayesian network, at least one neural network, combinations thereof, and/or the like to make estimations and/or determinations. Estimations and/or determinations corresponding to a low confidence level may, for example, be filtered, ignored, recalculated, combinations thereof, and/or the like.

Figure 31:
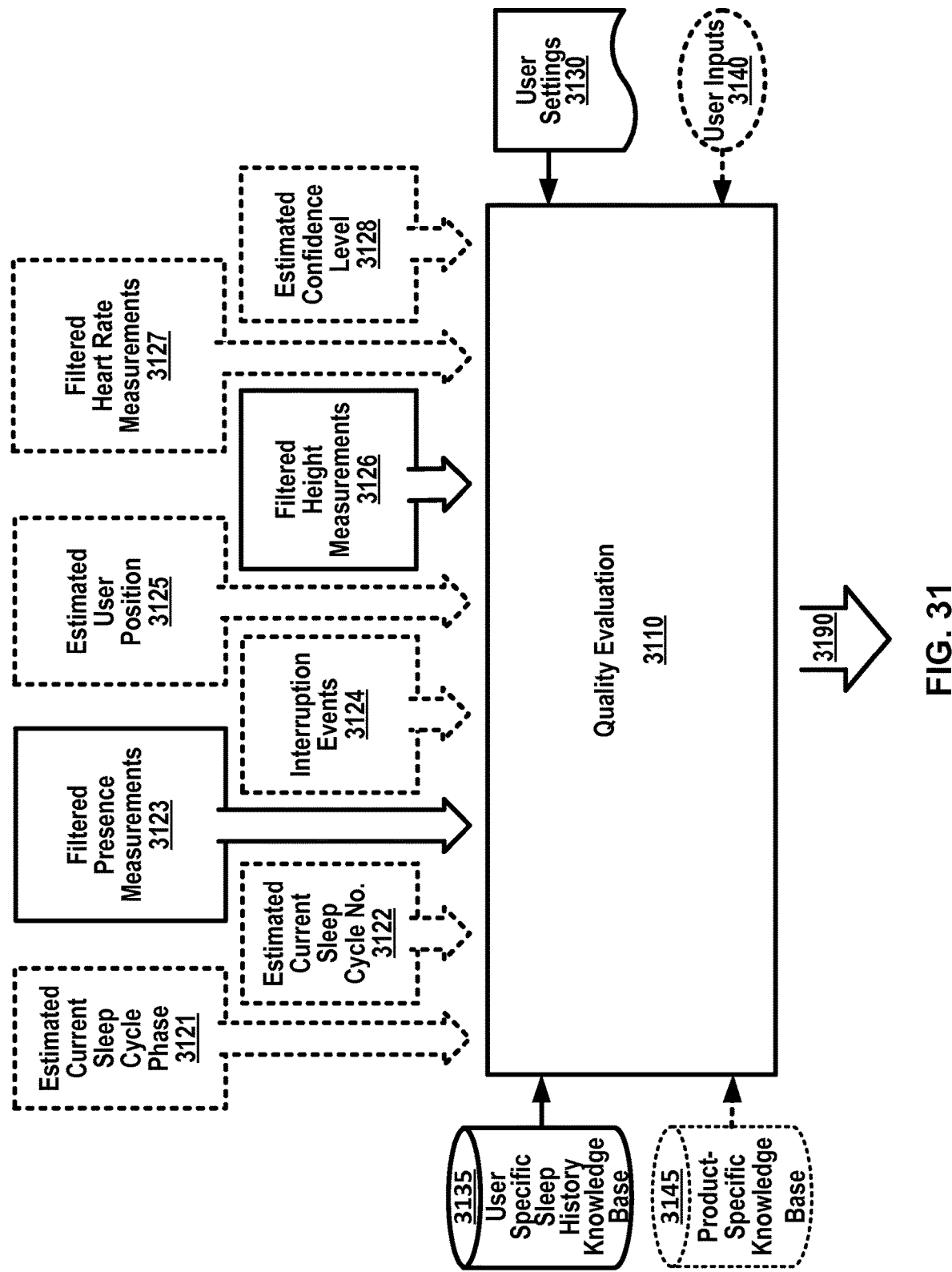
FIG. 31 is an example flow diagram of performing a sleep quality evaluation according to aspects of various embodiments.

FIG. 31 is an example flow diagram illustrating a system configured to perform an sleep quality evaluation 3110 employing a plurality of inputs (e.g. 3121, 3122 . . . 3128) according to aspects of various embodiments. The system may be configured to accept the following inputs: filtered presence measurements 3123, and filtered height measurements 3126. The system may be further configured to accept at least one of an estimated current sleep cycle phase 3121, an estimated current sleep cycle number 3122, interruption events 3124, at least one estimated position of a user 3125, filtered heart rate measurements 3127, at least one estimated confidence level 3128, a combinations thereof, and/or the like. The system may be configured to cause at least one processing unit (e.g. 150, 250, 350) to evaluate sleep quality at 3110. The system may be configured to employ user settings 3130, user-specific sleep history knowledge base 3135, and/or product-specific knowledge base 3145 to evaluate sleep quality at 3110. The system may be configured to produce a plurality of outputs 3190 for further processing. An example of further processing is described with respect to FIG. 32.

Sleep quality evaluation may, for example, comprise estimating a current sleep quality. The current sleep quality may, for example, be based at least in part on filtered presence measurements 3123. Estimating the current sleep quality may, for example, be based at least in part on at least one of: an estimated current sleep cycle phase 3121, an estimated current sleep cycle number 3122, interruption events 3124, filtered heart rate measurements 3127, combinations thereof, and/or the like. User-specific sleep history data from user-specific sleep history knowledge base 3135 may be employed to estimate the current sleep quality. Sleep quality evaluation may, for example, comprise estimating a cumulative sleep quality. The cumulative sleep quality may, for example, be based at least in part on at least one of: user-specific sleep history data from user-specific sleep history knowledge base 3135 and the current sleep quality. Sleep quality evaluation may, for example, comprise estimating an ideal sleep quality. The ideal sleep quality may, for example, be based at least in part on at least one of: user-specific sleep history data from user-specific sleep history knowledge base 3135, product-specific data from product-specific knowledge base 3145, user settings 3130, combinations thereof, and/or the like.

The plurality of outputs 3190 for further processing may comprise a recommended height. The recommended height may, for example, be based at least in part on at least one of: the current sleep quality, an ideal sleep quality, filtered height measurements 3126, combinations thereof, and/or the like. The recommended height may, for example, be based at least in part on a user input(s) 3140. By way of example and not limitation, user inputs 3140 may comprise a minimum height, a maximum height, a desired height, a minimum number of sleep cycles, a maximum number of sleep cycles, a desired number of sleep cycles, combinations thereof, and/or the like. The recommended height may, for example, be based at least in part on user-specific sleep history data from user-specific sleep history knowledge base 3135. The user-specific sleep history data may, for example, correlate to an estimated current sleep cycle phase 3121 and/or an estimated current sleep cycle number 3122. The recommended height may, for example, be based at least in part on an estimated confidence level 3128.

Sleep quality evaluation may, for example, comprise estimating an ideal position of a user. The ideal position of a user may, for example, be based at least in part on at least one estimated position of a user 3125. The ideal position of a user may, for example, be based at least in part on at least one of: user-specific sleep history data from user-specific sleep history knowledge base 3135, product-specific data from product-specific knowledge base 3145, user settings 3130, combinations thereof, and/or the like. The plurality of outputs 3190 for further processing may comprise a recommended position of a user. The recommended position of a user may, for example, be based at least in part on an ideal position of a user and at least one estimated position of a user 3125. The recommended position of a user may, for example, be based at least in part on an estimated confidence level 3128.

The plurality of outputs 3190 for further processing may comprise the estimated current sleep quality and the estimated cumulative sleep quality. Sleep quality evaluation may, for example, comprise determining a recommended sleep quality. Recommended sleep quality may, for example, be based at least in part on at least one of: the estimated current sleep quality, the estimated cumulative sleep quality, the ideal sleep quality, combinations thereof, and/or the like. According to some of the various embodiments, the recommended sleep quality may be based at least in part on an estimate of cumulative REM time. Cumulative REM time may be determined for at least one sleep cycle phase, at least one sleep cycle number, at least one sleeping session, combinations thereof, and/or the like. User-specific sleep history data from user-specific sleep history knowledge base 3135 may be employed to estimate the cumulative REM time. Furthermore, user settings 3130 may be employed to estimate the cumulative REM time. The recommended sleep quality may, for example, be based at least in part on an estimated confidence level 3128.

Figure 32:
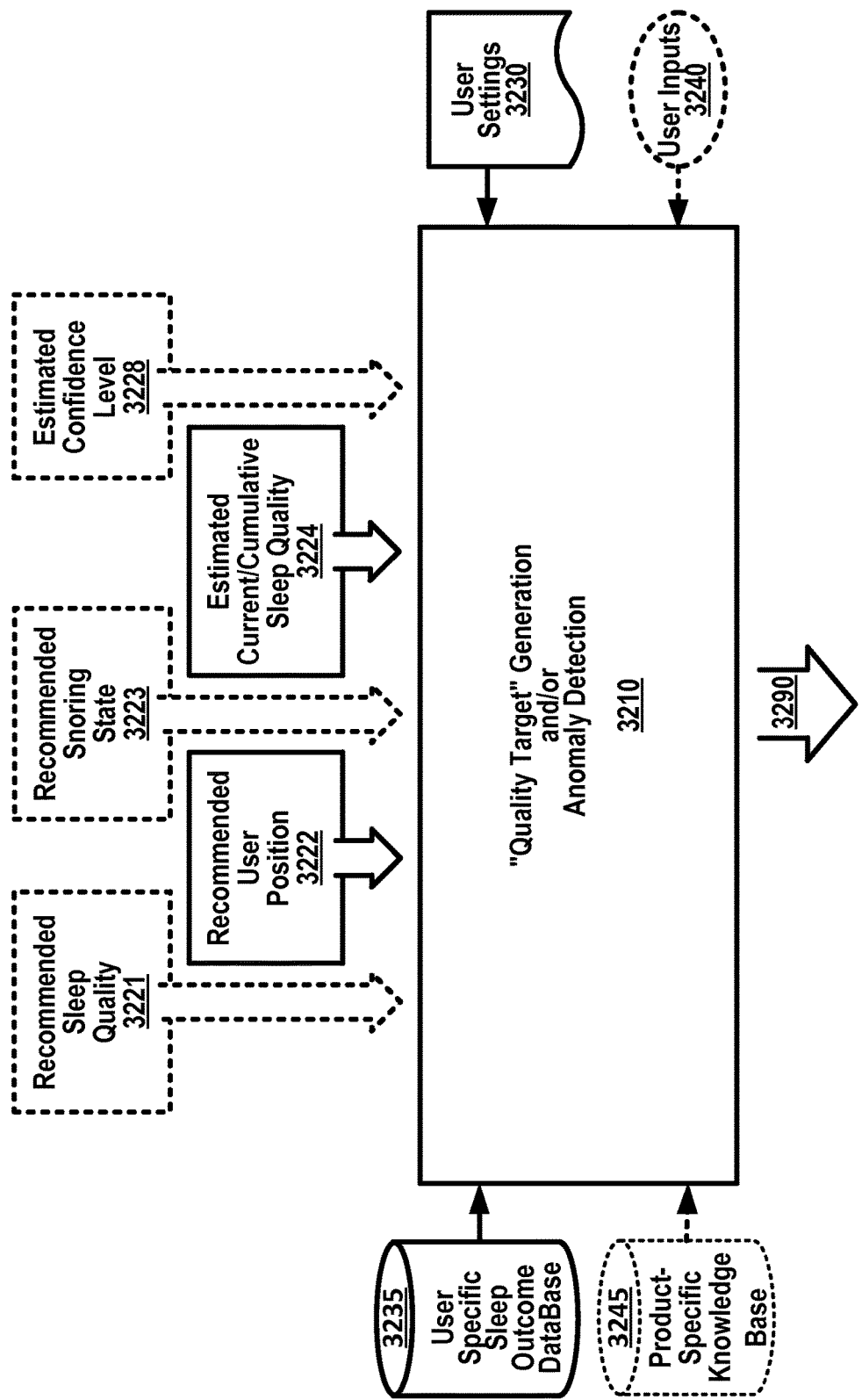
FIG. 32 is an example flow diagram of generating quality targets according to aspects of various embodiments.

FIG. 32 is an example flow diagram illustrating a system configured to generate quality targets 3210 employing a plurality of inputs (e.g. 3221, 3222 . . . 3228) according to aspects of various embodiments. The system may be further configured to detect anomalies at 3210. The system may be configured to accept the following inputs: recommended user position 3222, and estimated current and/or cumulative sleep quality 3224. The system may be further configured to accept at least one of: at least one recommended sleep quality 3221, at least one estimated confidence level 3228, a combinations thereof, and/or the like. The system may be configured to cause at least one processing unit (e.g. 150, 250, 350) to perform quality target generation and anomaly detection at 3210. The system may be configured to employ user settings 3230, user-specific sleep outcome database 3235, and/or product-specific knowledge base 3245 to generate quality targets and/or detect anomalies at 3210. The system may be configured to produce a plurality of outputs 3290 for further processing. An example of further processing is described with respect to FIG. 33.

Generating quality targets may, for example, comprise employment of product-specific data from product-specific knowledge base 3245 to calculate calibration adjustments. The product-specific data may, for example, be employed to calibrate at least one recommended user position. The product-specific data may, for example, comprise product-specific calibration data, sensor-specific calibration data, at least one maximum rate of height change, at least one power utilization minimum, at least one power utilization maximum, at least one power utilization target, combinations thereof, and/or the like. Generating quality targets may, for example, comprise employment of user settings 3230. User settings 3230 may, for example, comprise user calibration data. The user calibration data may, for example, be employed to calibrate at least one recommended user position. Generating quality targets may, for example, comprise employment of user inputs 3240. User inputs 3240 may, for example, comprise at least one manual override. The at least one manual override may, for example, be employed to adjust at least one recommended user position.

Generating quality targets may, for example, comprise calculating a difference between an estimated current and/or cumulative sleep quality and a recommended sleep quality. The difference may, for example, be employed to detect anomalies at 3210. Anomalies may, for example, be filtered, ignored, recalculated, combinations thereof, and/or the like.

The plurality of outputs 3290 for further processing may, for example, comprise at least one action to achieve a recommended user position. The action to achieve a recommended user position may, for example, be based at least in part on a calibrated input. The action to achieve a recommended user position may, for example, be based at least in part on product-specific data from product-specific knowledge base 3245. The product-specific data may, for example, be related to at least one height adjuster (e.g. 180, 280, 380). The action to achieve a recommended user position may, for example, be based at least in part on at least one user input 3240. The at least one user input 3240 may, for example, comprise a minimum height, a maximum height, a desired height, a maximum rate of height change, combinations thereof, and/or the like.

The plurality of outputs 3290 for further processing may, for example, comprise at least one recommendation to achieve sleep quality. The at least one recommendation to achieve sleep quality may, for example, be based at least in part on at least one of: a recommended sleep quality 3221, an estimated current sleep quality 3224, an estimated cumulative sleep quality 3224, combinations thereof, and/or the like. By way of example and not limitation, the recommendation to achieve sleep quality may comprise a recommended number of sleep cycles per sleeping session, a recommended start time for a sleeping session, a recommended wake time, combinations thereof, and/or the like.

Figure 33:
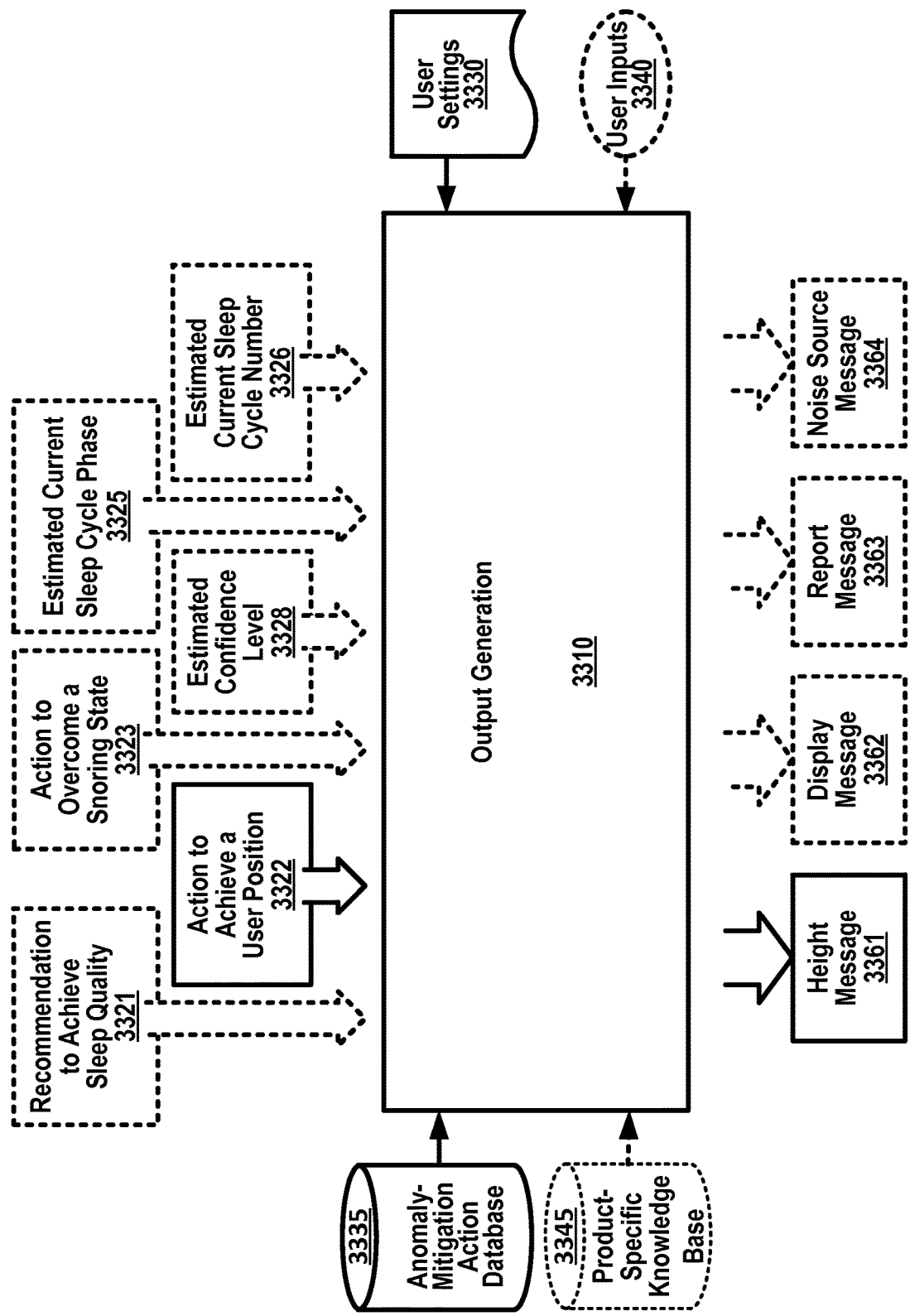
FIG. 33 is an example flow diagram of generating outputs according to aspects of various embodiments.

FIG. 33 is an example flow diagram illustrating a system configured to generate output 3310 employing a plurality of inputs (e.g. 3321, 3322 . . . 3328) according to aspects of various embodiments. The system may be configured to accept at least one action to achieve a user position 3322 as input. The system may be further configured to accept at least one of: at least one recommendation to achieve sleep quality 3321, at least one action to overcome a snoring state 3323, an estimated current sleep cycle phase 3325, an estimated current sleep cycle number 3326, at least one estimated confidence level 3328, a combination thereof, and/or the like. At least one action to overcome a snoring state 3323 may, for example, comprise an action configured to raise at least one height adjuster, an action configured to lower at least one height adjuster, an action configured to rapidly change the height of at least one height adjuster, an action configured to play at least one sound, combinations thereof, and/or the like. The system may be configured to cause at least one processing unit (e.g. 150, 250, 350) to generate output at 3310. The system may be configured to employ user settings 3330, anomaly mitigation action database 3335, product-specific knowledge base 3345, and/or user inputs 3340 to generate output at 3310. The at least one user input 3340 may, for example, depend on the estimated current sleep cycle phase 3325 and/or the estimated current sleep cycle number 3326.

Output generation at 3310 may comprise generating at least one height message 3361. The at least one height message 3361 may, for example, be based at least in part on at least one action to achieve a user position 3322. The at least one height message 3361 may, for example, be based at least in part on at least one action to overcome a snoring state 3323.

Output generation at 3310 may comprise generating at least one display message 3362. The at least one display message 3362 may, for example, be based at least in part on at least one of: at least one recommendation to achieve sleep quality 3321, at least one action to achieve a user position 3322, at least one action to overcome a snoring state 3323, an estimated current sleep cycle phase 3325, an estimated current sleep cycle number 3326, combinations thereof, and/or the like.

Output generation at 3310 may comprise generating at least one report message 3363. The at least one report message 3363 may, for example, be based at least in part on at least one of: at least one recommendation to achieve sleep quality 3321, at least one action to achieve a user position 3322, at least one action to overcome a snoring state 3323, an estimated current sleep cycle phase 3325, an estimated current sleep cycle number 3326, at least one user setting 3330, at least one user input 3340, combinations thereof, and/or the like.

Output generation at 3310 may comprise generating at least one noise source message 3364. The at least one noise source message 3364 may, for example, be based at least in part on at least one of: at least one recommendation to achieve sleep quality 3321, at least one user setting 3330, at least one user input 3340, combinations thereof, and/or the like.

Figure 34:
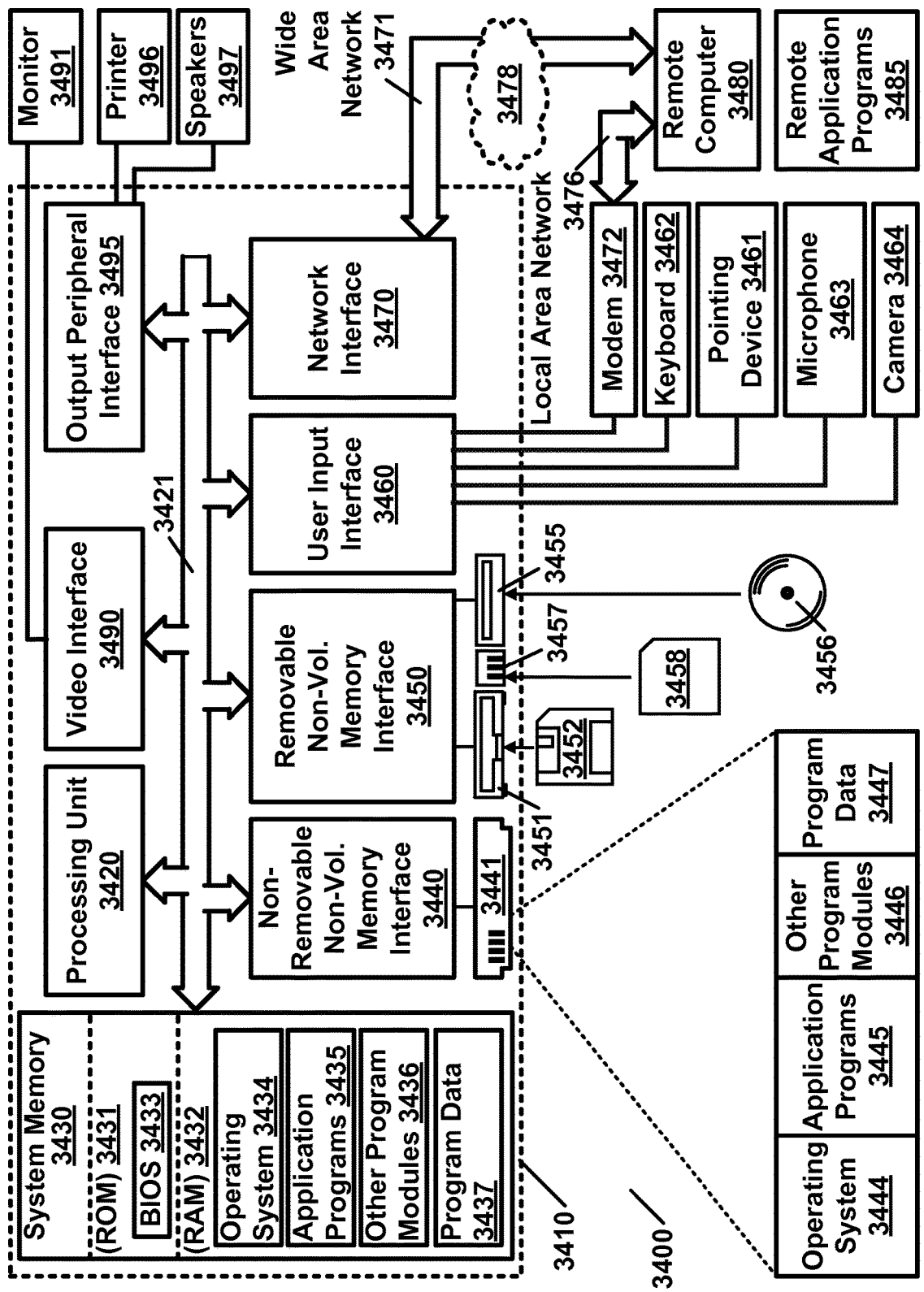
FIG. 34 is a block diagram of a computing environment in which aspects of embodiments of the present invention may be practiced.

FIG. 34 illustrates an example of a suitable computing system environment 3400 on which aspects of some embodiments may be implemented. The computing system environment 3400 is only one example of a suitable computing environment and is not intended to suggest any limitation as to the scope of use or functionality of the claimed subject matter. Neither should the computing environment 3400 be interpreted as having any dependency or requirement relating to any one or combination of components illustrated in the exemplary operating environment 3400.

Embodiments are operational with numerous other general purpose or special purpose computing system environments or configurations. Examples of well-known computing systems, environments, and/or configurations that may be suitable for use with various embodiments include, but are not limited to, embedded computing systems, personal computers, server computers, hand-held or laptop devices, multiprocessor systems, microprocessor-based systems, set top boxes, programmable consumer electronics, network PCs, minicomputers, mainframe computers, telephony systems, distributed computing environments that include any of the above systems or devices, and the like.

Embodiments may be described in the general context of computer-executable instructions, such as program modules, being executed by a computer. Generally, program modules include routines, programs, objects, components, data structures, etc. that perform particular tasks or implement particular abstract data types. Some embodiments are designed to be practiced in distributed computing environments where tasks are performed by remote processing devices that are linked through a communications network. In a distributed computing environment, program modules are located in both local and remote computer storage media including memory storage devices.

With reference to FIG. 34, an example system for implementing some embodiments includes a general-purpose computing device in the form of a computer 3410. Components of computer 3410 may include, but are not limited to, a processing unit 3420, a system memory 3430, and a system bus 3421 that couples various system components including the system memory to the processing unit 3420.

Computer 3410 typically includes a variety of computer readable media. Computer readable media can be any available media that can be accessed by computer 3410 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, random access memory (RAM), read-only memory (ROM), electrically erasable programmable read-only memory (EEPROM), flash memory or other memory technology, compact disc read-only memory (CD-ROM), digital versatile disks (DVD) or other optical disk storage, magnetic cassettes, magnetic tape, magnetic disk storage or other magnetic storage devices, or any other medium which can be used to store the desired information and which can be accessed by computer 3410. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer readable media.

The system memory 3430 includes computer storage media in the form of volatile and/or nonvolatile memory such as ROM 3431 and RAM 3432. A basic input/output system 3433 (BIOS), containing the basic routines that help to transfer information between elements within computer 3410, such as during start-up, is typically stored in ROM 3431. RAM 3432 typically contains data and/or program modules that are immediately accessible to and/or presently being operated on by processing unit 3420. By way of example, and not limitation, FIG. 34 illustrates operating system 3434, application programs 3435, other program modules 3436, and program data 3437.

The computer 3410 may also include other removable/non-removable volatile/nonvolatile computer storage media. By way of example only, FIG. 34 illustrates a hard disk drive 3441 that reads from or writes to non-removable, nonvolatile magnetic media, a magnetic disk drive 3451 that reads from or writes to a removable, nonvolatile magnetic disk 3452, a flash drive reader 3457 that reads flash drive 3458, and an optical disk drive 3455 that reads from or writes to a removable, nonvolatile optical disk 3456 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 3441 is typically connected to the system bus 3421 through a non-removable memory interface such as interface 3440, and magnetic disk drive 3451 and optical disk drive 3455 are typically connected to the system bus 3421 by a removable memory interface, such as interface 3450.

The drives and their associated computer storage media discussed above and illustrated in FIG. 34, provide storage of computer readable instructions, data structures, program modules and other data for the computer 3410. In FIG. 34, for example, hard disk drive 3441 is illustrated as storing operating system 3444, application programs 3445, program data 3447, and other program modules 3446. Additionally, for example, non-volatile memory may include instructions for reading and processing sensors 120, 130, 185, combinations thereof, and/or the like. Similarly, non-volatile memory may include instructions for controlling elements 140, 180, 160, combinations thereof, and/or the like.

A user may enter commands and information into the computer 3410 through input devices such as a keyboard 3462, a microphone 3463, a camera 3464, and a pointing device 3461, such as a mouse, trackball or touch pad. These and other input devices are often connected to the processing unit 3420 through a user input interface 3460 that is coupled to the system bus, but may be connected by other interface and bus structures, such as a parallel port, game port or a universal serial bus (USB). A monitor 3491 or other type of display device may also connected to the system bus 3421 via an interface, such as a video interface 3490. Other devices, such as, for example, speakers 3497 and printer 3496 may be connected to the system via peripheral interface 3495.

The computer 3410 is operated in a networked environment using logical connections to one or more remote computers, such as a remote computer 3480. The remote computer 3480 may be a personal computer, a hand-held device, a server, a router, a network PC, a peer device or other common network node, and typically includes many or all of the elements described above relative to the computer 3410. The logical connections depicted in FIG. 34 include a local area network (LAN) 3471 and a wide area network (WAN) 3473, but may also include other networks. Such networking environments are commonplace in offices, enterprise-wide computer networks, intranets and the Internet.

When used in a LAN networking environment, the computer 3410 is connected to the LAN 3471 through a network interface or adapter 3470. When used in a WAN networking environment, the computer 3410 typically includes a modem 3472 or other means for establishing communications over the WAN 3473, such as the Internet. The modem 3472, which may be internal or external, may be connected to the system bus 3421 via the user input interface 3460, or other appropriate mechanism. The modem 3472 may be wired or wireless. Examples of wireless devices may comprise, but are limited to: Wi-Fi and Bluetooth. In a networked environment, program modules depicted relative to the computer 3410, or portions thereof, may be stored in the remote memory storage device. By way of example, and not limitation, FIG. 34 illustrates remote application programs 3485 as residing on remote computer 3480. It will be appreciated that the network connections shown are exemplary and other means of establishing a communications link between the computers may be used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

In this specification, "a" and "an" and similar phrases are to be interpreted as "at least one" and "one or more." References to "an" embodiment in this disclosure are not necessarily to the same embodiment.

Many of the elements described in the disclosed embodiments may be implemented as modules. A module is defined here as an isolatable element that performs a defined function and has a defined interface to other elements. The modules described in this disclosure may be implemented in hardware, a combination of hardware and software, firmware, wetware (i.e. hardware with a biological element) or a combination thereof, all of which are behaviorally equivalent. For example, modules may be implemented using computer hardware in combination with software routine(s) written in a computer language (Java, HTML, XML, PHP, Python, ActionScript, JavaScript, Ruby, Prolog, SQL, VBScript, Visual Basic, Perl, C, C++, Objective-C or the like). Additionally, it may be possible to implement modules using physical hardware that incorporates discrete or programmable analog, digital and/or quantum hardware. Examples of programmable hardware include: computers, microcontrollers, microprocessors, application-specific integrated circuits (ASICs), field programmable gate arrays (FPGAs), and complex programmable logic devices (CPLDs). Computers, microcontrollers and microprocessors are programmed using languages such as assembly, C, C++ or the like. FPGAs, ASICs and CPLDs are often programmed using hardware description languages (HDL) such as VHSIC hardware description language (VHDL) or Verilog that configure connections between internal hardware modules with lesser functionality on a programmable device. Finally, it needs to be emphasized that the above mentioned technologies may be used in combination to achieve the result of a functional module.

Some embodiments may employ processing hardware. Processing hardware may include one or more processors, computer equipment, embedded system, machines a combination thereof, and/or the like. The processing hardware may be configured to execute instructions. The instructions may be stored on a machine-readable medium. According to some embodiments, the machine-readable medium (e.g. automated data medium) may be a medium configured to store data in a machine-readable format that may be accessed by an automated sensing device. Examples of machine-readable media include: magnetic disks, cards, tapes, and drums, flash memory, memory cards, electrically erasable programmable read-only memory (EEPROM), solid state drives, optical disks, barcodes, magnetic ink characters, a combination thereof, and/or the like.

While various embodiments have been described above, it should be understood that they have been presented by way of example, and not limitation. It will be apparent to persons skilled in the relevant art(s) that various changes in form and detail can be made therein without departing from the spirit and scope. For example and without limitation, figure elements in dashes reflect optional elements that may be employed by themselves or in combination with other elements as alternative embodiments. In fact, after reading the above description, it will be apparent to one skilled in the relevant art(s) how to implement alternative embodiments. Thus, the present embodiments should not be limited by any of the above described exemplary embodiments. In particular, it should be noted that, for example purposes, the presently described embodiments are discussed with respect to a pillow controllable to assist sleeping. However, one skilled in the art will recognize that embodiments may be employed to other objects such as mattresses, chairs, table tops, camping mats, combinations thereof, and/or the like.

In addition, it should be understood that any figures that highlight any functionality and/or advantages, are presented for example purposes only. The disclosed architecture is sufficiently flexible and configurable, such that it may be utilized in ways other than that shown. For example, the steps listed in any flowchart may be re-ordered or only optionally used in some embodiments.

Further, the purpose of the Abstract of the Disclosure is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The Abstract of the Disclosure is not intended to be limiting as to the scope in any way.

Finally, it is the applicant's intent that only claims that include the express language "means for" or "step for" be interpreted under 35 U.S.C. 112. Claims that do not expressly include the phrase "means for" or "step for" are not to be interpreted under 35 U.S.C. 112.

What is claimed is:

1. A reconfigurable pillow system for adjustably supporting a head of a user adaptive to the user's condition, comprising:
   a pillow defining a support surface for the user's head, said pillow including:
      a temperature regulation portion actuating to selectively applying thermal energy to said support surface; and,
      a height regulation portion actuating to selectively alter at least a part of said support surface in position;
   at least one presence sensing portion configured to acquire at least a positional state of the user with respect to said pillow; and,
   said controller executing on a processor to control actuation of said temperature and height regulation portions of said pillow with the user's head disposed in situ resting on said support surface thereof, said controller executing to actuate at least one of said temperature and height regulation portions responsive to a corresponding temperature measurement or height measurement, a user presence measurement, and biofeedback of the user's condition.

2. The reconfigurable pillow system as recited in claim 1, wherein said controller is programmably implemented on the processor to actuate said temperature and height regulation portions in selectively programmed manner.

3. The reconfigurable pillow system as recited in claim 2, wherein said controller is remotely disposed outside said pillow and coupled thereto by a predetermined communications link.

4. The reconfigurable pillow system as recited in claim 1, wherein said presence sensing portion includes at least one device selected from the group consisting of: a pressure sensor, a motion sensor, a location sensor, a weight sensor, a temperature sensor, an inductive proximity sensor, a capacitive proximity sensor, a piezoelectric element, a strain gauge, and an optical fiber.

5. The reconfigurable pillow system as recited in claim 1, wherein said height regulation portion includes:
   at least one height sensor configured to acquire the height measurement for the pillow for communication to said controller; and,
   at least one height adjuster configured to selectively raise and lower at least a part of said support surface in position responsive to said controller.

6. The reconfigurable pillow system as recited in claim 1, wherein said controller actuates at least one of said temperature and height regulation portions responsive at least in part to a sensor coupled to the user's body.

7. The reconfigurable pillow system as recited in claim 6, wherein said sensor includes a wearable device worn by the user for acquiring at least part of the biofeedback of the user's condition.

8. The reconfigurable pillow system as recited in claim 6, wherein said sensor measures at least parameter selected from the group consisting of: heart rate, heart rate variability, sympathetic tone, movement, location, and airflow.

9. The reconfigurable pillow system as recited in claim 1, wherein the biofeedback of the user's condition includes at least one of a breathing rate and a heart rate measurement of the user.

10. The reconfigurable pillow system as recited in claim 1, wherein said temperature regulation portion includes
   at least one temperature sensor configured to acquire the temperature measurement for the pillow for communication to said controller; and,
   at least one thermal element configured to generate thermal energy for said support surface responsive to said controller.

11. The reconfigurable pillow system as recited in claim 10, wherein said pillow defines at least one chamber; and, said thermal element applies thermal energy within said chamber through at least one medium selected from the group consisting of: direct heat, heated gas, heated liquid, heated gel, cooled liquid, cooled gel, and cooled gas.

12. The reconfigurable pillow system as recited in claim 10, wherein said thermal element includes at least one device selected from the group consisting of: a coil configured to circulate liquid, a coil configured to circulate gas, a tube configured to circulate liquid, a tube configured to circulate gas, a chemical cell, a metal wire element configured to electrically conduct current, a metal sheet configured to electrically conduct current, and a metal rod configured to electrically conduct current.

13. A reconfigurable pillow system for adjustably supporting a head of a user adaptive to the user's condition, comprising:
   a pillow defining a support surface for the user's head;
   at least one sensor configured to acquire biofeedback of the user's condition;
   a temperature regulation portion coupled to said pillow, said temperature regulation portion actuating to selectively heat or cool said support surface of said pillow, said temperature regulation portion having at least one thermal element configured to generate thermal energy for said support surface responsive to said controller;
   a height regulation portion coupled to said pillow, said height regulation portion actuating to selectively alter at least a part of said support surface in position, said height regulation portion having at least one height adjuster configured to selectively raise and lower at least a part of said support surface in position responsive to said controller;
   at least one presence sensing portion configured to acquire at least a positional state of the user with respect to said pillow; and,
   said controller executing on a processor to control actuation of said temperature and height regulation portions with the user's head disposed in situ resting on said support surface of said pillow, said controller executing to actuate at least one of said temperature and height regulation portions responsive to a corresponding temperature measurement or height measurement, a user presence measurement, and the biofeedback of the user's condition.

14. The reconfigurable pillow system as recited in claim 13, wherein the biofeedback of the user's condition includes at least one of a breathing rate and a heart rate measurement of the user.

15. The reconfigurable pillow system as recited in claim 13, wherein said controller is programmably implemented on the processor to actuate said temperature and height regulation portions in selectively programmed manner, said controller activating said thermal element responsive to said sensor and said presence sensing portion, and said controller activating said height adjuster responsive to said sensor and said presence sensing portion.

16. The reconfigurable pillow system as recited in claim 15, wherein said sensor is coupled to the user's body, said sensor including a wearable device worn by the user for acquiring at least part of the biofeedback of the user's condition.

17. The reconfigurable pillow system as recited in claim 13, wherein said sensor measures at least parameter selected from the group consisting of: heart rate, heart rate variability, sympathetic tone, movement, location, and airflow.

18. The reconfigurable pillow system as recited in claim 17, wherein said temperature regulation portion includes at least one temperature sensor configured to acquire the temperature measurement for the pillow for communication to said controller; and, said height regulation portion includes at least one height sensor configured to acquire the height measurement for the pillow for communication to said controller.

19. A reconfigurable pillow system for adjustably supporting a head of a user adaptive to the user's condition, comprising:
   a pillow defining a support surface for the user's head, said pillow including:
      a temperature regulation portion actuating to selectively applying thermal energy to said support surface; and,
      a height regulation portion actuating to selectively alter at least a part of said support surface in position;
   at least one presence sensing portion configured to acquire a presence measurement of the user with respect to said pillow; and,
   said controller executing on a processor to control actuation of said temperature and height regulation portions of said pillow with the user's head disposed in situ resting on said support surface thereof, said controller actuating at least one of said temperature and height regulation portions responsive to a corresponding temperature measurement or height measurement, a user presence measurement, and biofeedback of the user's condition.

20. The reconfigurable pillow system as recited in claim 19, wherein the biofeedback of the user's condition includes at least one of a breathing rate and a heart rate measurement of the user.

* * * * *